(12) United States Patent
Ramakrishnan

(10) Patent No.: US 8,592,149 B2
(45) Date of Patent: Nov. 26, 2013

(54) METHODS AND COMPOSITIONS FOR ANTIBODY THERAPY

(75) Inventor: Vijay Ramakrishnan, Palo Alto, CA (US)

(73) Assignee: PIKAMAB, Inc., Palo Alto, CA (US)

( * ) Notice: Subject to any disclaimer, the term of this patent is extended or adjusted under 35 U.S.C. 154(b) by 847 days.

(21) Appl. No.: 12/298,661

(22) PCT Filed: Apr. 27, 2007

(86) PCT No.: PCT/US2007/067663
§ 371 (c)(1),
(2), (4) Date: Jan. 8, 2010

(87) PCT Pub. No.: WO2007/127936
PCT Pub. Date: Nov. 8, 2007

(65) Prior Publication Data
US 2010/0291549 A1    Nov. 18, 2010

Related U.S. Application Data

(60) Provisional application No. 60/795,957, filed on Apr. 27, 2006.

(51) Int. Cl.
C12Q 1/68    (2006.01)
G01N 33/50    (2006.01)

(52) U.S. Cl.
USPC ............................ 435/6.1; 702/19; 702/20

(58) Field of Classification Search
None
See application file for complete search history.

(56) References Cited

U.S. PATENT DOCUMENTS

2005/0064417 A1    3/2005    Watier et al.
2006/0008825 A1    1/2006    Levy et al.

OTHER PUBLICATIONS

Farag, Sherif S. et al. FCGR3A and FCGR2A polymorphisms do not predict response to rituximab in B-cell chronic lymphocytic leukemia. Blood Feb. 15, 2004 Vol103 No. 4 pp. 1472-1474.*
Kastbom, Alf et al. FCG receptor type 3A genotype and response to tumor necrosis factor alpha-blocking agents in patients with rheumatoid arthritis. Arthritis and Rheumatism Feb. 2007 vol. 56 No. 2 pp. 448-452.*
Louis, Edouard Jet al. Polymorphism in IgG FC receptor gene FCGR3A and response to infliximab in Chron's disease: a subanalysis of the ACCENT I study. Pharmacogenetics and Genomics 2006 Vol16 pp. 911-914.*
Lin, Thomas S eta. FCGR3A and FCGR2A polymorphisms may not correlated with response to alemtuzumab in chronic lymphocytic leukemia. Blood 2005 Vol105 pp. 289-291.*
Cartron et al., "Therapeutic activity of humanized anti-CD20 monoclonal antibody and polymorphism in IgG Fc receptor FcγRIIIa gene," Blood, vol. 99, No. 3, pp. 754-758 (2002).
Weng et al., "Two Immunoglobulin G Fragment C Receptor Polymorphisms Independently Predict Response to Rituximab in Patients With Follicular Lymphoma," Journal of Clinical Oncology, vol. 21, No. 21, pp. 3940-3947 (2003).
Weng et al., "Genetic polymorphism of the inhibitory IgG Fc receptor FcγRIIb is not associated with clinical outcome in patients with follicular lymphoma treated with rituximab," Leukemia & Lymphoma, vol. 50, No. 5, pp. 723-727 (2009).

* cited by examiner

*Primary Examiner* — James Martinell
(74) *Attorney, Agent, or Firm* — Bozicevic, Field & Francis LLP; Elizabeth A. Alcamo; Bret E. Field

(57) ABSTRACT

Methods and materials are provided for determining the responsiveness of a subject to a therapy, such as an antibody therapy and for selecting and/or for treating a subject based on a FcγRIIA polymorphism, or a FcγRIIIA polymorphism, or both an FcγRIIA polymorphism and a FcγRIIIA polymorphism, including where the treatment is an therapy, such as rituximab. Methods and materials are also provided for designing, making, screening, testing and/or administering antibodies as well as for optimizing antibody therapies based upon a subject's FcγRIIA polymorphism, or FcγRIIIA polymorphism, or both the FcγRIIA polymorphism and the FcγRIIIA polymorphism.

40 Claims, 19 Drawing Sheets

Fig. 5

TABLE 1. CHARACTERISTICS OF THE PATIENTS ACCORDING TO
THEIR RESPONSE TO RITUXIMAB TREATMENT

| CHARACTERISTICS | NON RESPONSE (N=15) | PARTIAL RESPONSE (N=16) | COMPLETE RESPONSE (N=12) | ALL PATIENTS (N=43) |
|---|---|---|---|---|
| Sex (M/F) | 11/4 | 9/7 | 7/5 | 27/16 |
| Age (yr) | 49 ±8.8[#] | 56 ±14.9 | 52 ±7.5 | 52 ±11.5 |
| Pathology | | | | |
| FSC* | 10 | 6 | 6 | 22 |
| FM | 5 | 8 | 5 | 18 |
| FLC | 0 | 2 | 1 | 3 |
| Number of Prior Chemotherapy | 1 - 3[‡] (2.0) | 0 - 6 (2.0) | 0 - 5 (1.0) | 0 - 6 (2.0) |
| Prior Transplant Therapy | 2 | 3 | 2 | 7 |
| Bulky Disease | 10 | 5 | 5 | 20 |
| Stage   III | 2 | 4 | 4 | 10 |
|            IV | 13 | 12 | 8 | 33 |
| ≥ 2 Extranodal | 3 | 3 | 2 | 8 |
| Time between Diagnosis and Treatment (Mo) | 56 ±35 | 69 ±40 | 65 ±42 | 63 ±38 |
| Estimated Tumor Cells[†] in Biopsied Samples (%) | 76 - 98[‡] (95) | 70 - 98 (92) | 72 - 98 (80) | |

* FSC, follicular small cleaved
  FM, follicular mixed
  FLC, follicular large cell
[#] Plus-minus values are means ±SD
[‡] Range, values in parentheses are medians
[†] Calculation described in Method

Fig. 6

TABLE 2. CHARACTERISTICS OF THE PATIENTS ACCORDING TO
THEIR Fcγ RECEPTOR POLYMORPHISM

| CHARACTERISTICS | FcγR IIIa Polymorphism | | | ALL PATIENTS (N=87) | FcγR IIa Polymorphism | | |
|---|---|---|---|---|---|---|---|
| | V/V (N=13) | V/F (N=40) | F/F (N=34) | | H/H (N=20) | H/R (N=43) | R/R (N=24) |
| Sex (M/F) | 9/4 | 23/17 | 16/18 | 48/39 | 10/10 | 27/16 | 11/13 |
| Age (yr) | 56 ±14.5[#] | 52 ±13.0 | 49 ±9.1 | 51 ±12.0 | 50 ±10.4 | 53 ±12.4 | 49 ±12.1 |
| Pathology | | | | | | | |
|   FSC* | 9 | 20 | 18 | 47 | 10 | 23 | 14 |
|   FM | 2 | 18 | 15 | 35 | 8 | 17 | 10 |
|   FLC | 2 | 2 | 1 | 5 | 2 | 3 | 0 |
| Number of Prior Chemotherapy | 0 - 5[†] (1.0) | 0 - 4 (1.0) | 0 - 6 (1.0) | 0 - 6 (1.0) | 0 - 5 (1.0) | 0 - 6 (1.0) | 0 - 6 (1.0) |
| Prior Transplant Therapy | 1 | 4 | 5 | 10 | 1 | 8 | 1 |
| Bulky Disease | 6 | 22 | 18 | 46 | 9 | 21 | 15 |
| Stage   III | 1 | 9 | 6 | 16 | 5 | 9 | 2 |
|        IV | 12 | 31 | 28 | 61 | 15 | 34 | 22 |
| ≥ 2 Extranodal | 3 | 7 | 2 | 12 | 5 | 6 | 1 |
| Time between Diagnosis & Treatment (Mo) | 57 ±34 | 68 ±51 | 55 ±38 | 61 ±44 | 70 ±41 | 54 ±47 | 67 ±40 |

\* FSC, follicular small cleaved
  FM, follicular mixed
  FLC, follicular large cell
[#] Plus-minus values are means ±SD
[†] Range, values in parentheses are medians

Fig. 7

TABLE 3. CLINICAL RESPONSE TO RITUXIMAB THERAPY ACCORDING TO THEIR FCγ RECEPTOR IIIa POLYMORPHISM

|  | V/V | V/F | F/F | F Carrier[#] |  |
|---|---|---|---|---|---|
| 1-3 Months |  |  |  |  | $p^‡$ |
| Objective Response* | 12/13 (92%) | 21/40 (53%) | 23/34 (68%) | 44/74 (59%) | 0.027 |
| 6 Months |  |  |  |  |  |
| Objective Response | 11/13 (85%) | 15/38 (39%) | 15/29 (52%) | 30/67 (45%) | 0.013 |
| 9 Months |  |  |  |  |  |
| Objective Response | 9/12 (75%) | 12/36 (33%) | 11/28 (39%) | 23/64 (36%) | 0.023 |
| 12 Months |  |  |  |  |  |
| Objective Response | 9/12 (75%) | 8/35 (23%) | 8/27 (30%) | 16/62 (26%) | 0.002 |

* Objective Response includes PR, partial response and CR/CRu, complete response/complete response unconfirmed
[#] F Carrier, combination of V/F and F/F genotypes
‡ All P values are two-sided Fisher's exact test, comparing V/V to F Carrier

Fig. 8

TABLE 4. CLINICAL RESPONSE TO RITUXIMAB THERAPY ACCORDING TO
THEIR FCγ RECEPTOR IIa POLYMORPHISM

|  | H/H | H/R | R/R | R Carrier[#] | $p$[‡] |
|---|---|---|---|---|---|
| 1-3 Months |  |  |  |  |  |
| Objective Response* | 16/20 (80%) | 27/43 (63%) | 13/24 (54%) | 40/67 (60%) | 0.116 |
| 6 Months |  |  |  |  |  |
| Objective Response | 16/20 (80%) | 19/42 (45%) | 7/19 (37%) | 26/61 (43%) | 0.005 |
| 9 Months |  |  |  |  |  |
| Objective Response | 14/20 (70%) | 13/39 (33%) | 5/17 (29%) | 18/56 (32%) | 0.004 |
| 12 Months |  |  |  |  |  |
| Objective Response | 11/20 (55%) | 10/37 (27%) | 4/17 (24%) | 14/54 (26%) | 0.027 |

* Objective Response includes PR, partial response and CR/CRu, complete response/complete response unconfirmed
[#] R Carrier, combination of H/R and R/R genotypes
[‡] All P values are two-sided Fisher's exact test, comparing H/H to R Carrier

Fig. 9

TABLE 5. ANALYSIS OF Fcγ RECEPTOR IIa
AND Fcγ RECEPTOR IIIa POLYMORPHISM

| FcγR IIa | FcγR IIIa | | |
|---|---|---|---|
| H/H (N=20) | V/V | F Carrier | (V/F, F/F) |
|  | 3 (15%) | 17 (85%) | (14,3) |
| H/R (N=43) | V/V | F Carrier | (V/F, F/F) |
|  | 8 (19%) | 35 (81%) | (16, 19) |
| R/R (N=24) | V/V | F Carrier | (V/F, F/F) |
|  | 2 (8%) | 22 (92%) | (10,12) |

Fig. 10

TABLE 6. CLINICAL RESPONSE TO RITUXIMAB THERAPY ACCORDING TO
THEIR FCγ RECEPTOR IIa AND IIIa POLYMORPHISM

| 1-3 Months | Both 158 V/V and 131 H/H (N=3) | Either 158 V/V or 131 H/H (N=27) | Others (N=57) | p‡ |
|---|---|---|---|---|
| Objective Response* | 3/3 (100%) | 22/27 (81%) | 31/57 (54%) | *0.009* |
| 6 Months | | | | |
| Objective Response | 3/3 (100%) | 21/27 (78%) | 17/50 (34%) | *0.0001* |
| 9 Months | | | | |
| Objective Response | 3/3 (100%) | 17/26 (65%) | 12/47 (26%) | *0.0003* |
| 12 Months | | | | |
| Objective Response | 3/3 (100%) | 14/26 (54%) | 8/45 (18%) | *0.0004* |

\* Objective Response includes PR, partial response and CR/CRu, complete response/complete response unconfirmed
‡ All P values are two-sided Fisher's exact test, comparing 158 V/V and/or 131 H/H to Others

Fig. 11

TABLE 7. PROGNOSTIC FACTORS FOR CLINICAL RESPONSE: LOGISTIC REGRESSION ANALYSIS

|  | 1-3 Month | 6 Month | 9 Month | 12 Month |
|---|---|---|---|---|
| 158 V/V | 12.25 *<br>(1.35-111.16)<br>*0.026* # | 8.48<br>(1.54-46.60)<br>*0.014* | 7.94<br>(1.59-39.76)<br>*0.012* | 17.14<br>(2.94-100.18)<br>*0.002* |
| 131 H/H | 2.96<br>(0.85-10.35)<br>*0.090* | 8.03<br>(2.13-30.21)<br>*0.002* | 6.26<br>(1.86-21.06)<br>*0.003* | 7.25<br>(1.89-27.84)<br>*0.004* |
| Stage III vs IV | 0.66<br>(0.19-2.22)<br>*0.498* | 1.01<br>(0.28-3.62)<br>*0.984* | 0.62<br>(0.16-2.40)<br>*0.486* | 0.78<br>(0.16-3.85)<br>*0.759* |
| Age $\geq$ 60 | 3.08<br>(0.57-16.76)<br>*0.193* | 2.62<br>(0.57-12.12)<br>*0.217* | 1.73<br>(0.35-8.53)<br>*0.500* | 4.22<br>(0.73-24.25)<br>*0.107* |
| Prior Transplant Therapy | 0.86<br>(0.30-2.43)<br>*0.772* | 0.55<br>(0.17-1.73)<br>*0.304* | 1.24<br>(0.39-3.95)<br>*0.717* | 2.18<br>(0.56-8.45)<br>*0.261* |
| Bulky Disease | 1.81<br>(0.54-6.05)<br>*0.336* | 0.62<br>(0.17-2.27)<br>*0.470* | 0.68<br>(0.18-2.53)<br>*0.563* | 0.47<br>(0.11-2.14)<br>*0.333* |
| $\geq$ 2 Extranodal | 1.22<br>(0.30-4.89)<br>*0.784* | 0.32<br>(0.06-1.69)<br>*0.181* | 0.57<br>(0.11-2.84)<br>*0.489* | 0.23<br>(0.03-1.87)<br>*0.170* |

\* Odds ratio: relative odds of response to rituximab treatment, values in parentheses are 95% confidence intervals
All P values are two-sided and considered to be statistically significant for $P<0.05$

Figure 12-A

```
        83        90          100         110         120         130         140
        VHIGWLLL  QAPRWVFKEE  DPIHLRCHSW  KNTALHKVTY  LQNGKDRKYF  HHNSDFHIPK        FcγRIIIA
        |   ||| | |     | |        ||||||| |    |||    |||| |     |    | ||
        VLSEWLVL  QTPHLEFQEG  ETIMLRCHSW  KDKPLVKVTF  FQNGKSQKFS  RLDPTFSIPQ        FcγRIIA 150           160         170
        ATLKDSGSYF  CRGLVGSKNV  SSETVNITIT   FcγRIIIA  (SEQ ID NO: 26)
        |    ||| |   | | |        ||  | ||
        ANHSHSGDYH  CTGNIGYTLF  SSKPVTITVQ   FcγRIIA   (SEQ ID: NO 27)
```

Figure 12-B

```
           240         250         260         270         280         290         300
        CP APELLGGPSV  FLFPPKPKDT  LMISRTPEVT  CVVVDVSHED  PQVKFNWYVD  GVQVHNAKTK  PREQQYNSTY 310         320         330         340         350         360         370
        RVVSVLTVLH  QNWLDGKEYK  CKVSNKALPA  PIEKTISKAK  GQPREPQVYT  LPPSREEMTK  NQVSLTCLVK 380         390         400         410         420         430         440
        GFYPSDIAVE  WESNGQPENN  YKTTPPVLDS  DGSFFLYSKL  TVDKSRWQQG  NVFSCSVMHE  ALHNHYTQKS

444
        LSLS  (SEQ ID NO: 34)
```

Figure 12-C

|  | D1/D2 connector | B/C loop | C → | C' → | C'/E loop | F/G loop |
|---|---|---|---|---|---|---|
|  | 85 | 110 | 119 | 126 | 132 | 155  158 |
| FcγRI | RGW | WKDKLVYNVL | | AFKFFHW | | MGKH |
| FcγRIIa-HR | SEW | WKDKPLVKVT | | SQKFSRL | | IGYT |
| FcγRIIa-LR | SEW | WKDKPLVKVT | | SQKFSHL | | IGYT |
| FcγRIIb | SEW | WKDKPLVKVT | | SKKFSRS | | IGYT |
| FcεRIα | SDW | WRNWDVYKVI | | ALKYWYE | | VWQL |
| FcγRIII-V | IGW | WKNTALHKVT | | DRKYFHH | | VGSK |
| FcγRIII-F | IGW | WKNTALHKVT | | DRKYFHH | | FGSK |

|  |  |  |  |  |  |
|---|---|---|---|---|---|
| IgG1 | LLGGPS | DVSHE | NST | ALPAPI | |
| IgG2 | PVAGPS | DVSHE | NST | GLPAPI | |
| IgG3 | LLGGPS | DVSHE | NST | ALPAPI | |
| IgG4 | FLGGPS | DVSQE | NST | GLPSSI | |
| IgE | NPRGVS | DLAPS | NGT | HLPRAL | |
|  | 234  239 | 265  269 | 297 | 327  332 | |
|  | lower hinge | B/C loop | C'/E loop | F/G loop | |

Figure 12-D

Lower Hinge     ◄—— CPAPEL$^{234}$LGGPSVFLFPP$^{245}$ ——▶   (SEQ ID NO: 30)

B/C Loop        ◄—— EVTCVVVD$^{265}$VSHEDPQVKFNWYV$^{279}$ ——▶   (SEQ ID NO: 31)

C'/E Loop       ◄—— PREQQYN$^{297}$STYRVVSVLTV$^{308}$ ——▶   (SEQ ID NO: 32)

F/G Loop        ◄—— KEYKCKVSNKA$^{327}$LPAPIEKTISKAK$^{340}$ ——▶   (SEQ ID NO: 33)

| FcγRIIA | No. of Patients | FcγRIIIA | | | | | | |
|---|---|---|---|---|---|---|---|---|
| | | V/V | | V/F | | F/F | | F Carrier (V/F + F/F) |
| | | No. of Patients | % | No. of Patients | | No. of Patients | | No. of Patients | % |
| H/H | 20 | 3 | 15 | 14 | | 3 | | 17 | 85 |
| H/R | 43 | 8 | 19 | 16 | | 19 | | 35 | 81 |
| R/R | 24 | 2 | 8 | 10 | | 12 | | 22 | 92 |
| | 87 | 13 | | 40 | | 34 | | 74 | |

|  |  | FcγRIIIA VF[158] → | | | |
|---|---|---|---|---|---|
|  |  | VV | VF | FF | Total (%) |
| FcγRIIA HR[131] | HH | 3.4 | 16.1 | 3 | 23.0 |
|  | HR | 9.2 | 18.4 | 19 | 49.4 |
|  | RR | 2.3 | 11.5 | 12 | 27.6 |
|  | Total[1] (%) | 14.9 | 46.0 | 34 | 100.0 |
|  | HH | 6.1 | 13.3 | 21 | 31.1 |
|  | HR | 3.9 | 17.8 | 42 | 45.0 |
|  | RR | 0.6 | 8.3 | 27 | 23.9 |
|  | Total[2] (%) | 10.6 | 39.4 | 90 | 100.0 |
|  | HH | 4.0 | 12.0 | 16 | 26.7 |
|  | HR | 3.3 | 23.3 | 24 | 42.7 |
|  | RR | 0.7 | 14.7 | 23 | 30.7 |
|  | Total[2] (%) | 8.0 | 50.0 | 63 | 100.0 |
|  | HH | 6.7 | 7.4 | 17 | 20.4 |
|  | HR | 4.1 | 20.4 | 61 | 47.0 |
|  | RR | 3.0 | 9.6 | 54 | 32.6 |
|  | Total[3] (%) | 13.7 | 37.4 | 132 | 100.0 | n = 87 (first block)
n = 180 (second block)
n = 150 (third block)
n = 270 (fourth block)

1. Weng and Levy, *J. Clin. Oncol.* 21:3940, 2003
2. Lehrnbecher et al. *Blood* 94:4220, 1999
3. Torkildsen et al. *Immunology* 115:416, 2005

Fig. 15

```
Rituxin_Fc_portion    PELLGGPSVFLFPPKPKDTLMISRTPEVTCVVVDVSHEDPEVKFNWYVDGVEVHNAKTKP 60
Remicade_Fc_portion   PELLGGPSVFLFPPKPKDTLMISRTPEVTCVVVDVSHEDPEVKFNWYVDGVEVHNAKTKP 60
Erbitux_Fc_portion    PELLGGPSVFLFPPKPKDTLMISRTPEVTCVVVDVSHEDPEVKFNWYVDGVEVHNAKTKP 60
Campath_Fc_portion    PELLGGPSVFLFPPKPKDTLMISRTPEVTCVVVDVSHEDPEVKFNMYVDGVEVHNAKTKP 60
Herceptin_Fc_portion  PELLGGPSVFLFPPKPKDTLMISRTPEVTCVVVDVSHEDPEVKFNWYVDGVEVHNAKTKP 60
                      ************************************************ ***********

Rituxin_Fc_portion    REEQYNSTYRVVSVLTVLHQDWLNGKEYKCKVSNKALPAPIEKTISKAKGQPREPQVYTL 120
Remicade_Fc_portion   REEQYNSTYRVVSVLTVLHQDWLNGKEYKCKVSNKALPAPIEKTISKAKGQPREPQVYTL 120
Erbitux_Fc_portion    REEQYNSTYRVVSVLTVLHQDWLNGKEYKCKVSNKALPAPIEKTISKAKGQPREPQVYTL 120
Campath_Fc_portion    REEQYNSTYRVVSVLTVLHQDWLNGKEYKCKVSNKALPAPIEKTISKAKGQPREPQVYTL 120
Herceptin_Fc_portion  REEQYNSTYRVVSVLTVLHQDWLNGKEYKCKVSNKALPAPIEKTISKAKGQPREPQVYTL 120
                      ************************************************************

Rituxin_Fc_portion    PPSRDELTKNQVSLTCLVKGFYPSDIAVEWESNGQPENNYKTTPPVLDSDGSFFLYSKLT 180
Remicade_Fc_portion   PPSRDELTKNQVSLTCLVKGFYPSDIAVEWESNGQPENNYKTTPPVLDSDGSFFLYSKLT 180
Erbitux_Fc_portion    PPSRDELTKNQVSLTCLVKGFYPSDIAVEWESNGQPENNYKTTPPVLDSDGSFFLYSKLT 180
Campath_Fc_portion    PPSRDELTKNQVSLTCLVKGFYPSDIAVEWESNGQPENNYKTTPPVLDSDGSFFLYSKLT 180
Herceptin_Fc_portion  PPSRDELTKNQVSLTCLVKGFYPSDIAVEWESNGQPENNYKTTPPVLDSDGSFFLYSKLT 180
                      ************************************************************

Rituxin_Fc_portion    VDKSRWQQGNVFSCSVMHEALHNHYTQKSLSLSPGK 216    (SEQ ID NO: 1)
Remicade_Fc_portion   VDKSRWQQGNVFSCSVMHEALHNHYTQKSLSLSPGK 216    (SEQ ID NO: 12)
Erbitux_Fc_portion    VDKSRWQQGNVFSCSVMHEALHNHYTQKSLSLSPGK 216    (SEQ ID NO: 13)
Campath_Fc_portion    VDKSRWQQGNVFSCSVMHEALHNHYTQKSLSLSPGK 216    (SEQ ID NO: 14)
Herceptin_Fc_portion  VDKSRWQQGNVFSCSVMHEALHNHYTQKSLSLSPGK 216    (SEQ ID NO: 15)
                      ***********************************
```

SSM in Rituximab V_L CDR2 region

| APSNLAS | APSNLAS | APSNLAS | APSNLAS | APSNLAS | APSNLAS | APSNLAS |
|---------|---------|---------|---------|---------|---------|---------|
| C----- | -A---- | --A--- | ---A-- | ----A- | -----A- | ------A |
| D----- | -C---- | --C--- | ---C-- | ----C- | -----C- | ------C |
| E----- | -D---- | --D--- | ---D-- | ----D- | -----D- | ------D |
| F----- | -E---- | --E--- | ---E-- | ----E- | -----E- | ------E |
| G----- | -F---- | --F--- | ---F-- | ----F- | -----F- | ------F |
| H----- | -G---- | --G--- | ---G-- | ----G- | -----G- | ------G |
| I----- | -H---- | --H--- | ---H-- | ----H- | -----H- | ------H |
| K----- | -I---- | --I--- | ---I-- | ----I- | -----I- | ------I |
| L----- | -K---- | --K--- | ---K-- | ----K- | -----K- | ------K |
| M----- | -L---- | --L--- | ---L-- | ----M- | -----M- | ------L |
| N----- | -M---- | --M--- | ---M-- | ----N- | -----N- | ------M |
| P----- | -N---- | --N--- | ---N-- | ----P- | -----P- | ------N |
| Q----- | -P---- | --P--- | ---P-- | ----Q- | -----Q- | ------P |
| R----- | -Q---- | --Q--- | ---Q-- | ----R- | -----R- | ------Q |
| S----- | -R---- | --R--- | ---R-- | ----S- | -----S- | ------R |
| T----- | -S---- | --S--- | ---S-- | ----T- | -----T- | ------T |
| V----- | -T---- | --T--- | ---T-- | ----V- | -----V- | ------V |
| W----- | -V---- | --V--- | ---V-- | ----W- | -----W- | ------W |
| Y----- | -W---- | --W--- | ---W-- | ----Y- | -----Y- | ------Y |
| A----- | -Y---- | --Y--- | ---Y-- | ----L- | -----A- | ------S |
|        | -P---- | --S--- | ---N-- |        |         |         |

| | |
|---|---|
| γ3 | VDLKTPLGDTTHTCPRCP |
| γ1 | V----------------- |
| | 215 |
| γ3 | EPKSCDTPPPCPRCP |
| γ1 | --------------- |
| γ3 | EPKSCDTPPPCPRCP |
| γ1 | --------------- |
| γ3 | EPKSCDTPPPCPRCP |
| γ1 | EPKSCDKTHTCPPCP |
| | 216 |
| γ3 | APELLGGPSVFLFPP |
| γ1 | APELLGGPSVFLFPP |
| γ3 | KPKDTLMIS[254] |
| γ1 | KPKDTLMIS[254] |

SEQUENCE LISTING

```
<160> NUMBER OF SEQ ID NOS: 71

<210> SEQ ID NO 1
<211> LENGTH: 216
<212> TYPE: PRT
<213> ORGANISM: Artificial Sequence
<220> FEATURE:
<223> OTHER INFORMATION: synthetic polypeptide--Rituximab Fc-amino acid
      residues
<220> FEATURE:
<221> NAME/KEY: misc_feature
<223> OTHER INFORMATION: Rituximab Fc-amino acid residues

<400> SEQUENCE: 1

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205
```

```
Ser Leu Ser Leu Ser Pro Gly Lys
    210             215

<210> SEQ ID NO 2
<211> LENGTH: 210
<212> TYPE: PRT
<213> ORGANISM: Artificial Sequence
<220> FEATURE:
<223> OTHER INFORMATION: synthetic polypeptide--Rituximab light chain
<220> FEATURE:
<221> NAME/KEY: misc_feature
<223> OTHER INFORMATION: Rituximab light chain

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 3
<211> LENGTH: 447
<212> TYPE: PRT
<213> ORGANISM: Artificial Sequence
<220> FEATURE:
<223> OTHER INFORMATION: synthetic polypeptide--Rituximab Heavy chain
<220> FEATURE:
<221> NAME/KEY: misc_feature
<223> OTHER INFORMATION: Rituximab Heavy chain

<400> SEQUENCE: 3

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45
```

Gly Ala Ile Tyr Pro Gly Asn Gly Asp Thr Ser Tyr Asn Gln Lys Phe
 50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
             100                 105                 110

Gly Thr Gly Thr Thr Val Thr Val Ser Gly Pro Ser Val Phe Pro Leu
         115                 120                 125

Ala Pro Ser Ser Lys Ser Thr Gly Gly Thr Ala Ala Leu Gly Cys
     130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Lys Ala Glu Pro Lys Ser Cys Asp Lys Thr His
     210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
         435                 440                 445

<210> SEQ ID NO 4
<211> LENGTH: 211
<212> TYPE: PRT
<213> ORGANISM: Artificial Sequence

```
<220> FEATURE:
<223> OTHER INFORMATION: synthetic polypeptide--Remicade Mouse-human
      chimeric chain 1
<220> FEATURE:
<221> NAME/KEY: misc_feature
<223> OTHER INFORMATION: Remicade Mouse-human chimeric chain 1

<400> SEQUENCE: 4

Ser Ile Val Met Thr Gln Thr Pro Lys Phe Leu Leu Val Ser Ala Gly
1               5                   10                  15

Asp Arg Val Thr Ile Thr Cys Thr Ala Ser Gln Ser Val Ser Asn Asp
            20                  25                  30

Val Val Trp Tyr Gln Gln Lys Pro Gly Gln Ser Pro Lys Met Leu Met
        35                  40                  45

Tyr Ser Ala Phe Asn Arg Tyr Thr Gly Val Pro Asp Arg Phe Thr Gly
    50                  55                  60

Arg Gly Tyr Gly Thr Asp Phe Thr Phe Thr Ile Ser Ser Val Gln Ala
65                  70                  75                  80

Glu Asp Leu Ala Val Tyr Phe Cys Gln Gln Asp Tyr Asn Ser Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 5
<211> LENGTH: 443
<212> TYPE: PRT
<213> ORGANISM: Artificial Sequence
<220> FEATURE:
<223> OTHER INFORMATION: synthetic polypeptide--Remicade mouse-human
      chimeric chain 1
<220> FEATURE:
<221> NAME/KEY: misc_feature
<223> OTHER INFORMATION: Remicade mouse-human chimeric chain 1

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Glu His Phe Ala Phe Ser Leu Glu Thr Ser Ala Ser Thr Val Phe
65                  70                  75                  80
```

-continued

```
Leu Gln Ile Asn Asn Leu Lys Asn Glu Asp Thr Ala Thr Tyr Phe Cys
            85                  90                  95

Ala Arg Glu Arg Gly Asp Ala Met Asp Tyr Trp Gly Gln Gly Thr Ser
            100                 105                 110

Val Thr Val Ser Ser Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Ala Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 6
<211> LENGTH: 213
<212> TYPE: PRT
<213> ORGANISM: Artificial Sequence
<220> FEATURE:
<223> OTHER INFORMATION: synthetic polypeptide--Erbitux light chain 1
<220> FEATURE:
<221> NAME/KEY: misc_feature
<223> OTHER INFORMATION: Erbitux light chain 1
```

```
<400> SEQUENCE: 6

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
        210

<210> SEQ ID NO 7
<211> LENGTH: 452
<212> TYPE: PRT
<213> ORGANISM: Artificial Sequence
<220> FEATURE:
<223> OTHER INFORMATION: synthetic polypeptide--Erbitux heavy chain 1
<220> FEATURE:
<221> NAME/KEY: misc_feature
<223> OTHER INFORMATION: Erbitux heavy chain 1

<400> SEQUENCE: 7

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 8
<211> LENGTH: 214
<212> TYPE: PRT
<213> ORGANISM: Artificial Sequence
<220> FEATURE:
<223> OTHER INFORMATION: synthetic polypeptide--Herceptin light chain 1
<220> FEATURE:
<221> NAME/KEY: misc_feature
<223> OTHER INFORMATION: Herceptin light chain 1

<400> SEQUENCE: 8

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 451
<212> TYPE: PRT
<213> ORGANISM: Artificial Sequence
<220> FEATURE:
<223> OTHER INFORMATION: synthetic polypeptide--Herceptin heavy chain 1
<220> FEATURE:
<221> NAME/KEY: misc_feature
<223> OTHER INFORMATION: Herceptin heavy chain 1

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 211
<212> TYPE: PRT
<213> ORGANISM: Artificial Sequence
<220> FEATURE:
<223> OTHER INFORMATION: synthetic polypeptide--Campath light chain
<220> FEATURE:
<221> NAME/KEY: misc_feature
<223> OTHER INFORMATION: Campath light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45
```

```
Tyr Asn Thr Asn Asn Leu Gln Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 11
<211> LENGTH: 451
<212> TYPE: PRT
<213> ORGANISM: Artificial Sequence
<220> FEATURE:
<223> OTHER INFORMATION: synthetic polypeptide--Campath heavy chain
<220> FEATURE:
<221> NAME/KEY: misc_feature
<223> OTHER INFORMATION: Campath heavy chain

<400> SEQUENCE: 11

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
     50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 12
<211> LENGTH: 216
<212> TYPE: PRT
<213> ORGANISM: Artificial Sequence
<220> FEATURE:
<223> OTHER INFORMATION: synthetic polypeptide--Remicade Fc Region
<220> FEATURE:
<221> NAME/KEY: misc_feature
<223> OTHER INFORMATION: Remicade Fc Region

<400> SEQUENCE: 12

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Lys Phe Asn Trp Tyr Val
            35                  40                  45

Asp Gly Val Glu Val His Asn Ala Lys Thr Lys Pro Arg Glu Glu Gln
        50                  55                  60

Tyr Asn Ser Thr Tyr Arg Val Val Ser Val Leu Thr Val Leu His Gln
```

```
                65                  70                  75                  80
Asp Trp Leu Asn Gly Lys Glu Tyr Lys Cys Lys Val Ser Asn Lys Ala
                    85                  90                  95
Leu Pro Ala Pro Ile Glu Lys Thr Ile Ser Lys Ala Lys Gly Gln Pro
                    100                 105                 110
Arg Glu Pro Gln Val Tyr Thr Leu Pro Pro Ser Arg Asp Glu Leu Thr
                    115                 120                 125
Lys Asn Gln Val Ser Leu Thr Cys Leu Val Lys Gly Phe Tyr Pro Ser
                    130                 135                 140
Asp Ile Ala Val Glu Trp Glu Ser Asn Gly Gln Pro Glu Asn Asn Tyr
145                 150                 155                 160
Lys Thr Thr Pro Pro Val Leu Asp Ser Asp Gly Ser Phe Phe Leu Tyr
                    165                 170                 175
Ser Lys Leu Thr Val Asp Lys Ser Arg Trp Gln Gln Gly Asn Val Phe
                    180                 185                 190
Ser Cys Ser Val Met His Glu Ala Leu His Asn His Tyr Thr Gln Lys
                    195                 200                 205
Ser Leu Ser Leu Ser Pro Gly Lys
                    210                 215

<210> SEQ ID NO 13
<211> LENGTH: 216
<212> TYPE: PRT
<213> ORGANISM: Artificial Sequence
<220> FEATURE:
<223> OTHER INFORMATION: synthetic polypeptide--Erbitux Fc Region
<220> FEATURE:
<221> NAME/KEY: misc_feature
<223> OTHER INFORMATION: Erbitux Fc Region

<400> SEQUENCE: 13

Pro Glu Leu Leu Gly Gly Pro Ser Val Phe Leu Phe Pro Pro Lys Pro
1               5                   10                  15
Lys Asp Thr Leu Met Ile Ser Arg Thr Pro Glu Val Thr Cys Val Val
                    20                  25                  30
Val Asp Val Ser His Glu Asp Pro Glu Val Lys Phe Asn Trp Tyr Val
                    35                  40                  45
Asp Gly Val Glu Val His Asn Ala Lys Thr Lys Pro Arg Glu Glu Gln
    50                  55                  60
Tyr Asn Ser Thr Tyr Arg Val Val Ser Val Leu Thr Val Leu His Gln
65                  70                  75                  80
Asp Trp Leu Asn Gly Lys Glu Tyr Lys Cys Lys Val Ser Asn Lys Ala
                    85                  90                  95
Leu Pro Ala Pro Ile Glu Lys Thr Ile Ser Lys Ala Lys Gly Gln Pro
                    100                 105                 110
Arg Glu Pro Gln Val Tyr Thr Leu Pro Pro Ser Arg Asp Glu Leu Thr
                    115                 120                 125
Lys Asn Gln Val Ser Leu Thr Cys Leu Val Lys Gly Phe Tyr Pro Ser
                    130                 135                 140
Asp Ile Ala Val Glu Trp Glu Ser Asn Gly Gln Pro Glu Asn Asn Tyr
145                 150                 155                 160
Lys Thr Thr Pro Pro Val Leu Asp Ser Asp Gly Ser Phe Phe Leu Tyr
                    165                 170                 175
Ser Lys Leu Thr Val Asp Lys Ser Arg Trp Gln Gln Gly Asn Val Phe
                    180                 185                 190
Ser Cys Ser Val Met His Glu Ala Leu His Asn His Tyr Thr Gln Lys
                    195                 200                 205
```

Ser Leu Ser Leu Ser Pro Gly Lys
    210                 215

<210> SEQ ID NO 14
<211> LENGTH: 216
<212> TYPE: PRT
<213> ORGANISM: Artificial Sequence
<220> FEATURE:
<223> OTHER INFORMATION: synthetic polypeptide--Campath Fc Region
<220> FEATURE:
<221> NAME/KEY: misc_feature
<223> OTHER INFORMATION: Campath Fc Region

<400> SEQUENCE: 14

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 15
<211> LENGTH: 216
<212> TYPE: PRT
<213> ORGANISM: Artificial Sequence
<220> FEATURE:
<223> OTHER INFORMATION: synthetic polypeptide--Herceptin Fc Region
<220> FEATURE:
<221> NAME/KEY: misc_feature
<223> OTHER INFORMATION: Herceptin Fc Region

<400> SEQUENCE: 15

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

```
Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 16
<211> LENGTH: 10
<212> TYPE: PRT
<213> ORGANISM: Artificial Sequence
<220> FEATURE:
<223> OTHER INFORMATION: synthetic peptide--Rituximab CDR1 Variable
      Light Chain (VL)
<220> FEATURE:
<221> NAME/KEY: misc_feature
<223> OTHER INFORMATION: Rituximab CDR1 Variable Light Chain (VL)

<400> SEQUENCE: 16

Arg Ala Ser Ser Ser Val Ser Tyr Met His
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic peptide--Rituximab CDR1 Variable
      Heavy Chain (VH)
<220> FEATURE:
<221> NAME/KEY: misc_feature
<223> OTHER INFORMATION: Rituximab CDR1 Variable Heavy Chain (VH)

<400> SEQUENCE: 17

Gly Tyr Thr Phe Thr Ser Tyr Asn Met His
1               5                   10

<210> SEQ ID NO 18
<211> LENGTH: 7
<212> TYPE: PRT
<213> ORGANISM: Artificial Sequence
<220> FEATURE:
<223> OTHER INFORMATION: synthetic peptide--Rituximab CDR2 Variable
      Light Chain (VL)
<220> FEATURE:
<221> NAME/KEY: misc_feature
<223> OTHER INFORMATION: Rituximab CDR2 Variable Light Chain (VL)
```

```
<400> SEQUENCE: 18

Ala Pro Ser Asn Leu Ala Ser
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide--Rituximab CDR3 Variable
      Light Chain (VL)
<220> FEATURE:
<221> NAME/KEY: misc_feature
<223> OTHER INFORMATION: Rituximab CDR3 Variable Light Chain (VL)

<400> SEQUENCE: 19

Gln Gln Trp Ser Phe Asn Pro Pro Thr
1               5

<210> SEQ ID NO 20
<211> LENGTH: 13
<212> TYPE: PRT
<213> ORGANISM: Artificial Sequence
<220> FEATURE:
<223> OTHER INFORMATION: synthetic peptide--Rituximab CDR3 Variable
      Heavy Chain (VH)
<220> FEATURE:
<221> NAME/KEY: misc_feature
<223> OTHER INFORMATION: Rituximab CDR3 Variable Heavy Chain (VH)

<400> SEQUENCE: 20

Val Val Tyr Tyr Ser Asn Ser Tyr Trp Tyr Phe Asp Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic peptide--Rituximab CDR1 Variable
      Light Chain (VL)
<220> FEATURE:
<221> NAME/KEY: misc_feature
<223> OTHER INFORMATION: Rituximab CDR1 Variable Light Chain (VL)

<400> SEQUENCE: 21

Arg Ala Ser Ser Ser Val Ser Tyr Met His
1               5                   10

<210> SEQ ID NO 22
<211> LENGTH: 9
<212> TYPE: PRT
<213> ORGANISM: Artificial Sequence
<220> FEATURE:
<223> OTHER INFORMATION: synthetic peptide--Rituximab CDR3 Variable
      Heavy Chain (VH)
<220> FEATURE:
<221> NAME/KEY: misc_feature
<223> OTHER INFORMATION: Rituximab CDR3 Variable Heavy Chain (VH)

<400> SEQUENCE: 22

Gln Gln Trp Ser Phe Asn Pro Pro Thr
1               5

<210> SEQ ID NO 23
<211> LENGTH: 13
<212> TYPE: PRT
<213> ORGANISM: Artificial Sequence
<220> FEATURE:
<223> OTHER INFORMATION: synthetic peptide--Rituximab CDR3 Variable
```

```
                    Heavy Chain (VH)
<220> FEATURE:
<221> NAME/KEY: misc_feature
<223> OTHER INFORMATION: Rituximab CDR3 Variable Heavy Chain (VH)

<400> SEQUENCE: 23

Val Val Tyr Tyr Ser Asn Ser Tyr Trp Tyr Phe Asp Val
1               5                   10

<210> SEQ ID NO 24
<211> LENGTH: 86
<212> TYPE: PRT
<213> ORGANISM: Homo sapiens
<220> FEATURE:
<221> NAME/KEY: misc_feature
<223> OTHER INFORMATION: Hinge Region of IgG3

<400> SEQUENCE: 24

Val Asp Leu Lys Thr Pro Leu Gly Asp Thr Thr His Thr Cys Pro Arg
1               5                   10                  15

Cys Pro Glu Pro Lys Ser Cys Asp Thr Pro Pro Pro Cys Pro Arg Cys
            20                  25                  30

Pro Glu Pro Lys Ser Cys Asp Thr Pro Pro Pro Cys Pro Arg Cys Pro
        35                  40                  45

Glu Pro Lys Ser Cys Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser
                85

<210> SEQ ID NO 25
<211> LENGTH: 40
<212> TYPE: PRT
<213> ORGANISM: Homo sapiens
<220> FEATURE:
<221> NAME/KEY: misc_feature
<223> OTHER INFORMATION: Hinge region of IgG1

<400> SEQUENCE: 25

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser
        35                  40

<210> SEQ ID NO 26
<211> LENGTH: 88
<212> TYPE: PRT
<213> ORGANISM: Homo sapiens
<220> FEATURE:
<221> NAME/KEY: misc_feature
<223> OTHER INFORMATION: Fc RIIIa

<400> SEQUENCE: 26

Val His Ile Gly Trp Leu Leu Leu Gln Ala Pro Arg Trp Val Phe Lys
1               5                   10                  15

Glu Glu Asp Pro Ile His Leu Arg Cys His Ser Trp Lys Asn Thr Ala
            20                  25                  30

Leu His Lys Val Thr Tyr Leu Gln Asn Gly Lys Asp Arg Lys Tyr Phe
        35                  40                  45

His His Asn Ser Asp Phe His Ile Pro Lys Ala Thr Leu Lys Asp Ser
```

-continued

```
                50                  55                  60

Gly Ser Tyr Phe Cys Arg Gly Leu Val Gly Ser Lys Asn Val Ser Ser
 65                  70                  75                  80

Glu Thr Val Asn Ile Thr Ile Thr
                 85

<210> SEQ ID NO 27
<211> LENGTH: 88
<212> TYPE: PRT
<213> ORGANISM: Homo sapiens
<220> FEATURE:
<221> NAME/KEY: misc_feature
<223> OTHER INFORMATION: Fc RIIa

<400> SEQUENCE: 27

Val Leu Ser Glu Trp Leu Val Leu Gln Thr Pro His Leu Glu Phe Gln
  1               5                  10                  15

Glu Gly Glu Thr Ile Met Leu Arg Cys His Ser Trp Lys Asp Lys Pro
                 20                  25                  30

Leu Val Lys Val Thr Phe Phe Gln Asn Gly Lys Ser Gln Lys Phe Ser
             35                  40                  45

Arg Leu Asp Pro Thr Phe Ser Ile Pro Gln Ala Asn His Ser His Ser
 50                  55                  60

Gly Asp Tyr His Cys Thr Gly Asn Ile Gly Tyr Thr Leu Phe Ser Ser
 65                  70                  75                  80

Lys Pro Val Thr Ile Thr Val Gln
                 85

<210> SEQ ID NO 28
<211> LENGTH: 107
<212> TYPE: PRT
<213> ORGANISM: Homo sapiens
<220> FEATURE:
<221> NAME/KEY: misc_feature
<223> OTHER INFORMATION: 12b-1

<400> SEQUENCE: 28

Cys Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val Thr
                 20                  25                  30

Cys Val Val Val Asp Val Ser His Glu Asp Pro Gln Val Lys Phe Asn
             35                  40                  45

Trp Tyr Val Asp Gly Val Gln Val His Asn Ala Lys Thr Lys Pro Arg
 50                  55                  60

Glu Gln Gln Tyr Asn Ser Thr Tyr Arg Val Val Ser Val Leu Thr Val
 65                  70                  75                  80

Leu His Gln Asn Trp Leu Asp Gly Lys Glu Tyr Lys Cys Lys Val Ser
                 85                  90                  95

Asn Lys Ala Leu Pro Ala Pro Ile Glu Lys Thr
                100                 105

<210> SEQ ID NO 29
<211> LENGTH: 109
<212> TYPE: PRT
<213> ORGANISM: Homo sapiens
<220> FEATURE:
<221> NAME/KEY: misc_feature
<223> OTHER INFORMATION: 12b-2

<400> SEQUENCE: 29
```

```
Ile Ser Lys Ala Lys Gly Gln Pro Arg Glu Pro Gln Val Tyr Thr Leu
1               5                   10                  15

Pro Pro Ser Arg Glu Glu Met Thr Lys Asn Gln Val Ser Leu Thr Cys
            20                  25                  30

Leu Val Lys Gly Phe Tyr Pro Ser Asp Ile Ala Val Glu Trp Glu Ser
                35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Asp Lys Ser
65                  70                  75                  80

Arg Trp Gln Gln Gly Asn Val Phe Ser Cys Ser Val Met His Glu Ala
                85                  90                  95

Leu His Asn His Tyr Thr Gln Lys Ser Leu Ser Leu Ser
            100                 105
```

<210> SEQ ID NO 30
<211> LENGTH: 17
<212> TYPE: PRT
<213> ORGANISM: Homo sapiens
<220> FEATURE:
<221> NAME/KEY: misc_feature
<223> OTHER INFORMATION: Fc lower hinge region

<400> SEQUENCE: 30

```
Cys Pro Ala Pro Glu Leu Leu Gly Gly Pro Ser Val Phe Leu Phe Pro
1               5                   10                  15

Pro
```

<210> SEQ ID NO 31
<211> LENGTH: 22
<212> TYPE: PRT
<213> ORGANISM: Homo sapiens
<220> FEATURE:
<221> NAME/KEY: misc_feature
<223> OTHER INFORMATION: Fc BC Loop Region

<400> SEQUENCE: 31

```
Glu Val Thr Cys Val Val Val Asp Val Ser His Glu Asp Pro Gln Val
1               5                   10                  15

Lys Phe Asn Trp Tyr Val
                20
```

<210> SEQ ID NO 32
<211> LENGTH: 18
<212> TYPE: PRT
<213> ORGANISM: Homo sapiens
<220> FEATURE:
<221> NAME/KEY: misc_feature
<223> OTHER INFORMATION: Fc CE Loop Region

<400> SEQUENCE: 32

```
Pro Arg Glu Gln Gln Tyr Asn Ser Thr Tyr Arg Val Val Ser Val Leu
1               5                   10                  15

Thr Val
```

<210> SEQ ID NO 33
<211> LENGTH: 24
<212> TYPE: PRT
<213> ORGANISM: Homo sapiens
<220> FEATURE:
<221> NAME/KEY: MISC_FEATURE
<223> OTHER INFORMATION: Fc FG loop Region

<400> SEQUENCE: 33

```
Lys Glu Tyr Lys Cys Lys Val Ser Asn Lys Ala Leu Pro Ala Pro Ile
1               5                   10                  15

Glu Lys Thr Ile Ser Lys Ala Lys
                20
```

<210> SEQ ID NO 34
<211> LENGTH: 216
<212> TYPE: PRT
<213> ORGANISM: Homo sapiens
<220> FEATURE:
<221> NAME/KEY: misc_feature
<223> OTHER INFORMATION: hIgG1 from residues 229-444 (Figure 12B)

<400> SEQUENCE: 34

```
Cys Pro Ala Pro Glu Leu Leu Gly Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Asp Pro Gln Val Lys Phe Asn
            35                  40                  45

Trp Tyr Val Asp Gly Val Gln Val His Asn Ala Lys Thr Lys Pro Arg
    50                  55                  60

Glu Gln Gln Tyr Asn Ser Thr Tyr Arg Val Val Ser Val Leu Thr Val
65                  70                  75                  80

Leu His Gln Asn Trp Leu Asp Gly Lys Glu Tyr Lys Cys Lys Val Ser
                85                  90                  95

Asn Lys Ala Leu Pro Ala Pro Ile Glu Lys Thr Ile Ser Lys Ala Lys
                100                 105                 110

Gly Gln Pro Arg Glu Pro Gln Val Tyr Thr Leu Pro Pro Ser Arg Glu
            115                 120                 125

Glu Met Thr Lys Asn Gln Val Ser Leu Thr Cys Leu Val Lys Gly Phe
    130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Lys Leu Thr Val Asp Lys Ser Arg Trp Gln Gln Gly
                180                 185                 190

Asn Val Phe Ser Cys Ser Val Met His Glu Ala Leu His Asn His Tyr
            195                 200                 205

Thr Gln Lys Ser Leu Ser Leu Ser
    210                 215
```

<210> SEQ ID NO 35
<211> LENGTH: 17
<212> TYPE: PRT
<213> ORGANISM: Homo sapiens
<220> FEATURE:
<221> NAME/KEY: misc_feature
<223> OTHER INFORMATION: CDR2 VH

<400> SEQUENCE: 35

```
Ala Ile Tyr Pro Gly Asn Gly Asp Thr Ser Tyr Asn Gln Lys Phe Lys
1               5                   10                  15

Gly
```

<210> SEQ ID NO 36
<211> LENGTH: 10
<212> TYPE: PRT

```
<213> ORGANISM: Artificial sequence
<220> FEATURE:
<223> OTHER INFORMATION: synthetic peptide--FcGammaR1 B/C loop
<220> FEATURE:
<221> NAME/KEY: misc_feature
<223> OTHER INFORMATION: FcGammaR1 B/C loop

<400> SEQUENCE: 36

Trp Lys Asp Lys Leu Val Tyr Asn Val Leu
1               5                   10

<210> SEQ ID NO 37
<211> LENGTH: 7
<212> TYPE: PRT
<213> ORGANISM: Artificial sequence
<220> FEATURE:
<223> OTHER INFORMATION: synthetic peptide--FcGammaR1 C/E loop
<220> FEATURE:
<221> NAME/KEY: misc_feature
<223> OTHER INFORMATION: FcGammaR1 C/E loop

<400> SEQUENCE: 37

Ala Phe Lys Phe Phe His Trp
1               5

<210> SEQ ID NO 38
<211> LENGTH: 4
<212> TYPE: PRT
<213> ORGANISM: Artificial sequence
<220> FEATURE:
<223> OTHER INFORMATION: synthetic peptide--FcGammaR1 F/G loop
<220> FEATURE:
<221> NAME/KEY: misc_feature
<223> OTHER INFORMATION: FcGammaR1 F/G loop

<400> SEQUENCE: 38

Met Gly Lys His
1

<210> SEQ ID NO 39
<211> LENGTH: 10
<212> TYPE: PRT
<213> ORGANISM: Artificial sequence
<220> FEATURE:
<223> OTHER INFORMATION: synthetic peptide--FcGammaRIIa-HR B/C loop
<220> FEATURE:
<221> NAME/KEY: misc_feature
<223> OTHER INFORMATION: FcGammaRIIa-HR B/C loop

<400> SEQUENCE: 39

Trp Lys Asp Lys Pro Leu Val Lys Val Thr
1               5                   10

<210> SEQ ID NO 40
<211> LENGTH: 7
<212> TYPE: PRT
<213> ORGANISM: Artificial sequence
<220> FEATURE:
<223> OTHER INFORMATION: synthetic peptide--FcGammaRIIa-HR C/E loop
<220> FEATURE:
<221> NAME/KEY: misc_feature
<223> OTHER INFORMATION: FcGammaRIIa-HR C/E loop

<400> SEQUENCE: 40

Ser Gln Lys Phe Ser Arg Leu
1               5

<210> SEQ ID NO 41
<211> LENGTH: 4
<212> TYPE: PRT
```

```
<213> ORGANISM: Artificial sequence
<220> FEATURE:
<223> OTHER INFORMATION: synthetic peptide--FcGammaRIIa-HR F/G loop
<220> FEATURE:
<221> NAME/KEY: misc_feature
<223> OTHER INFORMATION: FcGammaRIIa-HR F/G loop

<400> SEQUENCE: 41

Ile Gly Tyr Thr
1

<210> SEQ ID NO 42
<211> LENGTH: 10
<212> TYPE: PRT
<213> ORGANISM: Artificial sequence
<220> FEATURE:
<223> OTHER INFORMATION: synthetic peptide--FcGammaRIIa-LR B/C loop
<220> FEATURE:
<221> NAME/KEY: misc_feature
<223> OTHER INFORMATION: FcGammaRIIa-LR B/C loop

<400> SEQUENCE: 42

Trp Lys Asp Lys Pro Leu Val Lys Val Thr
1               5                   10

<210> SEQ ID NO 43
<211> LENGTH: 7
<212> TYPE: PRT
<213> ORGANISM: Artificial sequence
<220> FEATURE:
<223> OTHER INFORMATION: synthetic peptide--FcGammaRIIa-LR C/E loop
<220> FEATURE:
<221> NAME/KEY: misc_feature
<223> OTHER INFORMATION: FcGammaRIIa-LR C/E loop

<400> SEQUENCE: 43

Ser Gln Lys Phe Ser His Leu
1               5

<210> SEQ ID NO 44
<211> LENGTH: 4
<212> TYPE: PRT
<213> ORGANISM: Artificial sequence
<220> FEATURE:
<223> OTHER INFORMATION: synthetic peptide--FcGammaRIIa-LR F/G loop
<220> FEATURE:
<221> NAME/KEY: misc_feature
<223> OTHER INFORMATION: FcGammaRIIa-LR F/G loop

<400> SEQUENCE: 44

Ile Gly Tyr Thr
1

<210> SEQ ID NO 45
<211> LENGTH: 10
<212> TYPE: PRT
<213> ORGANISM: Artificial sequence
<220> FEATURE:
<223> OTHER INFORMATION: synthetic peptide--FcGammaRIIb B/C loop
<220> FEATURE:
<221> NAME/KEY: misc_feature
<223> OTHER INFORMATION: FcGammaRIIb B/C loop

<400> SEQUENCE: 45

Trp Lys Asp Lys Pro Leu Val Lys Val Thr
1               5                   10

<210> SEQ ID NO 46
<211> LENGTH: 7
<212> TYPE: PRT
```

```
<213> ORGANISM: Artificial sequence
<220> FEATURE:
<223> OTHER INFORMATION: synthetic peptide--FcGammaRIIb C/E loop
<220> FEATURE:
<221> NAME/KEY: misc_feature
<223> OTHER INFORMATION: FcGammaRIIb C/E loop

<400> SEQUENCE: 46

Ser Lys Lys Phe Ser Arg Ser
1               5

<210> SEQ ID NO 47
<211> LENGTH: 4
<212> TYPE: PRT
<213> ORGANISM: Artificial sequence
<220> FEATURE:
<223> OTHER INFORMATION: synthetic peptide--FcGammaRIIb F/G loop

<400> SEQUENCE: 47

Ile Gly Tyr Thr
1

<210> SEQ ID NO 48
<211> LENGTH: 10
<212> TYPE: PRT
<213> ORGANISM: Artificial sequence
<220> FEATURE:
<223> OTHER INFORMATION: synthetic peptide--FcEpsilonR1alpha  B/C loop
<220> FEATURE:
<221> NAME/KEY: misc_feature
<223> OTHER INFORMATION: FcEpsilonR1alpha  B/C loop

<400> SEQUENCE: 48

Trp Arg Asn Trp Asp Val Tyr Lys Val Ile
1               5                   10

<210> SEQ ID NO 49
<211> LENGTH: 7
<212> TYPE: PRT
<213> ORGANISM: Artificial sequence
<220> FEATURE:
<223> OTHER INFORMATION: synthetic peptide--FcEpsilonR1alpha C/E loop
<220> FEATURE:
<221> NAME/KEY: misc_feature
<223> OTHER INFORMATION: FcEpsilonR1alpha C/E loop

<400> SEQUENCE: 49

Ala Leu Lys Tyr Trp Tyr Glu
1               5

<210> SEQ ID NO 50
<211> LENGTH: 4
<212> TYPE: PRT
<213> ORGANISM: Artificial sequence
<220> FEATURE:
<223> OTHER INFORMATION: synthetic peptide--FcEpsilonR1alpha F/G loop
<220> FEATURE:
<221> NAME/KEY: misc_feature
<223> OTHER INFORMATION: FcEpsilonR1alpha F/G loop

<400> SEQUENCE: 50

Val Trp Gln Leu
1

<210> SEQ ID NO 51
<211> LENGTH: 10
<212> TYPE: PRT
<213> ORGANISM: Artificial sequence
<220> FEATURE:
<223> OTHER INFORMATION: synthetic peptide--FcGammaRIII-V B/C loop
```

```
<220> FEATURE:
<221> NAME/KEY: misc_feature
<223> OTHER INFORMATION: FcGammaRIII-V B/C loop

<400> SEQUENCE: 51

Trp Lys Asn Thr Ala Leu His Lys Val Thr
1               5                   10

<210> SEQ ID NO 52
<211> LENGTH: 7
<212> TYPE: PRT
<213> ORGANISM: Artificial sequence
<220> FEATURE:
<223> OTHER INFORMATION: synthetic peptide--FcGammaRIII-V C/E loop
<220> FEATURE:
<221> NAME/KEY: misc_feature
<223> OTHER INFORMATION: FcGammaRIII-V C/E loop

<400> SEQUENCE: 52

Asp Arg Lys Tyr Phe His His
1               5

<210> SEQ ID NO 53
<211> LENGTH: 4
<212> TYPE: PRT
<213> ORGANISM: Artificial sequence
<220> FEATURE:
<223> OTHER INFORMATION: synthetic peptide--FcGammaRIII-V F/G loop
<220> FEATURE:
<221> NAME/KEY: misc_feature
<223> OTHER INFORMATION: FcGammaRIII-V F/G loop

<400> SEQUENCE: 53

Val Gly Ser Lys
1

<210> SEQ ID NO 54
<211> LENGTH: 10
<212> TYPE: PRT
<213> ORGANISM: Artificial sequence
<220> FEATURE:
<223> OTHER INFORMATION: synthetic peptide--FcGammaRIII-F B/C loop
<220> FEATURE:
<221> NAME/KEY: misc_feature
<223> OTHER INFORMATION: FcGammaRIII-F B/C loop

<400> SEQUENCE: 54

Trp Lys Asn Thr Ala Leu His Lys Val Thr
1               5                   10

<210> SEQ ID NO 55
<211> LENGTH: 7
<212> TYPE: PRT
<213> ORGANISM: Artificial sequence
<220> FEATURE:
<223> OTHER INFORMATION: synthetic peptide--FcGammaRIII-F C/E loop
<220> FEATURE:
<221> NAME/KEY: misc_feature
<223> OTHER INFORMATION: FcGammaRIII-F C/E loop

<400> SEQUENCE: 55

Asp Arg Lys Tyr Phe His His
1               5

<210> SEQ ID NO 56
<211> LENGTH: 4
<212> TYPE: PRT
<213> ORGANISM: Artificial sequence
<220> FEATURE:
<223> OTHER INFORMATION: synthetic peptide--FcGammaRIII-F F/G loop
```

```
<220> FEATURE:
<221> NAME/KEY: misc_feature
<223> OTHER INFORMATION: FcGammaRIII-F F/G loop

<400> SEQUENCE: 56

Phe Gly Ser Lys
1

<210> SEQ ID NO 57
<211> LENGTH: 6
<212> TYPE: PRT
<213> ORGANISM: Artificial sequence
<220> FEATURE:
<223> OTHER INFORMATION: synthetic peptide--IgG1 lower hinge
<220> FEATURE:
<221> NAME/KEY: misc_feature
<223> OTHER INFORMATION: IgG1 lower hinge

<400> SEQUENCE: 57

Leu Leu Gly Gly Pro Ser
1               5

<210> SEQ ID NO 58
<211> LENGTH: 5
<212> TYPE: PRT
<213> ORGANISM: Artificial sequence
<220> FEATURE:
<223> OTHER INFORMATION: synthetic peptide--IgG1 B/C loop
<220> FEATURE:
<221> NAME/KEY: misc_feature
<223> OTHER INFORMATION: IgG1 B/C loop

<400> SEQUENCE: 58

Asp Val Ser His Glu
1               5

<210> SEQ ID NO 59
<211> LENGTH: 6
<212> TYPE: PRT
<213> ORGANISM: Artificial sequence
<220> FEATURE:
<223> OTHER INFORMATION: synthetic peptide--IgG1 F/G loop
<220> FEATURE:
<221> NAME/KEY: misc_feature
<223> OTHER INFORMATION: IgG1 F/G loop

<400> SEQUENCE: 59

Ala Leu Pro Ala Pro Ile
1               5

<210> SEQ ID NO 60
<211> LENGTH: 6
<212> TYPE: PRT
<213> ORGANISM: Artificial sequence
<220> FEATURE:
<223> OTHER INFORMATION: synthetic peptide--IgG2 lower hinge
<220> FEATURE:
<221> NAME/KEY: misc_feature
<223> OTHER INFORMATION: IgG2 lower hinge

<400> SEQUENCE: 60

Pro Val Ala Gly Pro Ser
1               5

<210> SEQ ID NO 61
<211> LENGTH: 5
<212> TYPE: PRT
<213> ORGANISM: Artificial sequence
<220> FEATURE:
<223> OTHER INFORMATION: synthetic peptide--IgG21 B/C loop
```

```
<220> FEATURE:
<221> NAME/KEY: misc_feature
<223> OTHER INFORMATION: IgG21 B/C loop

<400> SEQUENCE: 61

Asp Val Ser His Glu
1               5

<210> SEQ ID NO 62
<211> LENGTH: 6
<212> TYPE: PRT
<213> ORGANISM: Artificial sequence
<220> FEATURE:
<223> OTHER INFORMATION: synthetic peptide--IgG2 F/G loop
<220> FEATURE:
<221> NAME/KEY: misc_feature
<223> OTHER INFORMATION: IgG2 F/G loop

<400> SEQUENCE: 62

Gly Leu Pro Ala Pro Ile
1               5

<210> SEQ ID NO 63
<211> LENGTH: 6
<212> TYPE: PRT
<213> ORGANISM: Artificial sequence
<220> FEATURE:
<223> OTHER INFORMATION: synthetic peptide--IgG3 lower hinge
<220> FEATURE:
<221> NAME/KEY: misc_feature
<223> OTHER INFORMATION: IgG3 lower hinge

<400> SEQUENCE: 63

Leu Leu Gly Gly Pro Ser
1               5

<210> SEQ ID NO 64
<211> LENGTH: 5
<212> TYPE: PRT
<213> ORGANISM: Artificial sequence
<220> FEATURE:
<223> OTHER INFORMATION: synthetic peptide--IgG3 B/C loop
<220> FEATURE:
<221> NAME/KEY: misc_feature
<223> OTHER INFORMATION: IgG3 B/C loop

<400> SEQUENCE: 64

Asp Val Ser His Glu
1               5

<210> SEQ ID NO 65
<211> LENGTH: 6
<212> TYPE: PRT
<213> ORGANISM: Artificial sequence
<220> FEATURE:
<223> OTHER INFORMATION: synthetic peptide--IgG3 F/G loop
<220> FEATURE:
<221> NAME/KEY: misc_feature
<223> OTHER INFORMATION: IgG3 F/G loop

<400> SEQUENCE: 65

Ala Leu Pro Ala Pro Ile
1               5

<210> SEQ ID NO 66
<211> LENGTH: 6
<212> TYPE: PRT
<213> ORGANISM: Artificial sequence
<220> FEATURE:
<223> OTHER INFORMATION: synthetic peptide--IgG4 lower hinge
```

```
<400> SEQUENCE: 66

Phe Leu Gly Gly Pro Ser
1               5

<210> SEQ ID NO 67
<211> LENGTH: 5
<212> TYPE: PRT
<213> ORGANISM: Artificial sequence
<220> FEATURE:
<223> OTHER INFORMATION: synthetic peptide--IgG4 B/C loop
<220> FEATURE:
<221> NAME/KEY: misc_feature
<223> OTHER INFORMATION: IgG4 B/C loop

<400> SEQUENCE: 67

Asp Val Ser Gln Glu
1               5

<210> SEQ ID NO 68
<211> LENGTH: 6
<212> TYPE: PRT
<213> ORGANISM: Artificial sequence
<220> FEATURE:
<223> OTHER INFORMATION: synthetic peptide--IgG4 F/G loop
<220> FEATURE:
<221> NAME/KEY: misc_feature
<223> OTHER INFORMATION: IgG4 F/G loop

<400> SEQUENCE: 68

Gly Leu Pro Ser Ser Ile
1               5

<210> SEQ ID NO 69
<211> LENGTH: 6
<212> TYPE: PRT
<213> ORGANISM: Artificial sequence
<220> FEATURE:
<223> OTHER INFORMATION: synthetic peptide--IgGE lower hinge
<220> FEATURE:
<221> NAME/KEY: misc_feature
<223> OTHER INFORMATION: IgGE lower hinge

<400> SEQUENCE: 69

Asn Pro Arg Gly Val Ser
1               5

<210> SEQ ID NO 70
<211> LENGTH: 5
<212> TYPE: PRT
<213> ORGANISM: Artificial sequence
<220> FEATURE:
<223> OTHER INFORMATION: synthetic peptide--IgGE B/C loop
<220> FEATURE:
<221> NAME/KEY: misc_feature
<223> OTHER INFORMATION: IgGE B/C loop

<400> SEQUENCE: 70

Asp Leu Ala Pro Ser
1               5

<210> SEQ ID NO 71
<211> LENGTH: 6
<212> TYPE: PRT
<213> ORGANISM: Artificial sequence
<220> FEATURE:
<223> OTHER INFORMATION: synthetic peptide--IgGE F/G loop
<220> FEATURE:
<221> NAME/KEY: misc_feature
<223> OTHER INFORMATION: IgGE F/G loop
```

```
<400> SEQUENCE: 71

His Leu Pro Arg Ala Leu
1               5
```

US 8,592,149 B2

METHODS AND COMPOSITIONS FOR ANTIBODY THERAPY

CROSS REFERENCE TO RELATED APPLICATIONS

This application is a National Stage of International Application No. PCT/US2007/067663, filed Apr. 27, 2007, which claims the benefit under 35 U.S.C. §119(e) of U.S. provisional application No. 60/795,957, filed Apr. 27, 2006, each of which is incorporated by reference in its entirety.

BACKGROUND

A number of antibodies have been developed, including for their use in therapies for a variety of diseases, disorders or conditions. For example, in the fall of 1997, the anti-CD20 monoclonal antibody, rituximab (currently sold under the brand name RITUXAN®), was approved for the treatment of refractory or relapsed low-grade B-cell non-Hodgkin's lymphoma (NHL). Rituximab has since become a mainstay of treatment for low-grade NHL and over 400,000 patients worldwide have been treated with rituximab. Despite this extensive clinical experience, the mechanism of action of rituximab remains unclear, as does the nature of resistance.

Rituximab is a chimeric antibody consisting of a murine CD20-binding variable region linked to human IgG1 constant region. CD20 is a cell surface protein expressed on B-lymphocytes. CD20 has four transmembrane domains and has been proposed to act as an ion channel; however, the function of CD20 remains poorly understood. Phase II trials of rituximab in people with refractory or relapsed low grade or follicular NHL demonstrated a 50% response rate. While the nature of de novo resistance to rituximab is unclear, such resistance is very rarely due to loss of the CD20 antigen, which cannot be shed or internalized and is rarely down-regulated. Despite these properties of CD20, acquired resistance to rituximab is common in that only half of patients previously responding to rituximab will respond to a second course of treatment.

An effective and practical diagnostic protocol which could provide information as to whether a patient is or is not responsive to a therapy, including an antibody therapy such as rituximab therapy, would be desirable for a number of reasons, including avoidance of delays in alternative treatments, elimination of exposure to adverse effects of the therapy and reduction of unnecessary expense. As such, there is interest in the development of protocols that can accurately predict whether or not a patient is responsive to such therapies. There is also an interest in the development of antibodies and antibody therapies that would be effective or more effective in patients that were non-responsive or poorly responsive to a particular therapy.

SUMMARY

Methods and materials are provided for determining the responsiveness of a subject to a therapy, such as an antibody therapy and for selecting and/or for treating a subject based on a FcγRIIA polymorphism, or a FcγRIIIA polymorphism, or both an FcγRIIA polymorphism and a FcγRIIIA polymorphism, including where the treatment is an therapy, such as rituximab. Methods and materials are also provided for designing, making, screening, testing and/or administering antibodies as well as for optimizing antibody therapies based upon a subject's FcγRIIA polymorphism, or FcγRIIIA polymorphism, or both the FcγRIIA polymorphism and the FcγRIIIA polymorphism.

Methods and compositions are provided for determining whether a subject suffering from a neoplastic condition is responsive to an antineoplastic therapy, such as antibody therapy, e.g., rituximab therapy. In practicing the subject methods, the subject is genotyped to determine whether the subject has at least one favorable FcγR polymorphism, e.g., the $H/H^{131}$ genotype in FcγRIIA or the $V/V^{158}$ genotype in FcγRIIIA. In addition, reagents, devices and kits thereof, that find use in practicing the subject methods are provided.

Methods are provided for determining the degree of responsiveness that a subject having an ADCC-treatable disease or disorder will have to an antibody therapy for the disease or disorder by genotyping the subject for an FcγRIIA polymorphism to obtain a first result, genotyping the subject for an FcγRIIIA polymorphism to obtain a second result, assigning the subject to one of more than three categories of treatment response and/or employing the first and second results to determine the degree of the responsiveness of the subject to the antibody therapy.

Methods are provided for selecting a specific Fc variant antibody therapy from a set of two or more Fc variant antibody therapies for use in treating subjects having an ADCC-treatable disease by genotyping the subjects for an FcγRIIA polymorphism to classify patient population into three groups (e.g., $H/H^{131}$, $H/R^{131}$, $R/R^{131}$), genotyping the subjects for an FcγRIIIA polymorphism to classify patient population into three groups (e.g., $V/V^{158}$, $V/F^{158}$, $F/F^{158}$), classifying the subjects into nine patient groups I-IX based on the first and second results, and employing the first and second results to select a specific Fc variant antibody therapy for the patient group such that the degree of treatment response to antibody therapy in the patient group is improved. Subjects may be classified into nine groups based on their genotype, including: $V/V^{158}$, $H/H^{131}$ (Group-I); $V/F^{158}$, $H/H^{131}$ (Group-II); $F/F^{158}$, $H/H^{131}$ (Group-III); $V/V^{158}$, $H/R^{131}$ (Group-IV); $V/F^{158}$, $H/R^{131}$ (Group-V); $F/F^{158}$, $H/R^{131}$ (Group-VI); $V/V^{158}$ $R/R^{131}$ (Group-VII); $V/F^{158}$, $R/R^{131}$ (Group-VIII); and $F/F^{158}$, $R/R^{131}$ (Group-IX).

Methods are also provided for making a set of related antibodies by modifying the amino acid sequence of at least one Fc region amino acid residue in a parent antibody, such that the modified Fc region exhibits enhanced binding affinity to at least one Fc receptor encoded by an Fc receptor gene of a first genotype, compared to the Fc binding affinity of the parent antibody, to generate a first Fc variant antibody; and/or modifying at least one Fc region amino acid residue in a parent antibody, such that the modified constant region exhibits enhanced binding affinity to at least one Fc receptor encoded by an Fc receptor gene of a second genotype, compared to the Fc binding affinity of the parent antibody, to generate a second Fc variant antibody, wherein the first and second Fc variant antibodies have the same antigen specificity.

Also provided are kits for use in determining responsiveness to an antibody therapy in a patient which include an element for genotyping a sample to identify a FcγRIIA polymorphism, an element for genotyping the sample to identify a FcγRIIIA polymorphism, or an element for genotyping the sample to identify a FcγRIIIA polymorphism and an FcγRIIA, and a reference that correlates a genotype with predicted therapeutic response to a therapeutic antibody.

Methods are provided for of treating an ADCC-treatable disease or disorder in an individual by determining a category of therapeutic responsiveness to an antibody therapy by genotyping the individual for an FcγRIIA polymorphism and an FcγRIIIA polymorphism, wherein the FcγRIIA polymorphism and the FcγRIIIA polymorphism together indicate a degree of therapeutic responsiveness; selecting an antibody from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function; and administering an effective amount of the antibody to the individual.

Methods are provided for determining the degree of responsiveness to an antibody-dependent cell-mediated cytotoxicity antibody therapy by genotyping the subject for two or more Fcγ receptor polymorphisms and employing the first and second Fcγ receptor polymorphisms to determine the degree of the responsiveness of the subject to the antibody therapy.

Methods are also provided for generating a set of Fc variant antibodies by amplifying a nucleic acid comprising a nucleotide sequence encoding an Fc region of an antibody, wherein the amplifying is carried out with a set of primers that encode all nineteen amino acid variants at a single residue of the Fc region, to generate a set of variant nucleic acids encoding nineteen amino acid substitution variants at the single residue of the Fc region; transcribing and translating each of the variant nucleic acids in vitro, to generate a set of Fc variants; and/or c) selecting from the set an Fc variant having altered FcR binding activity compared to a reference Fc, generating a set of selected Fc variants.

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the H/H$^{131}$ genotype, or both the V/V$^{158}$ genotype, the H/H$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the H/H$^{131}$ genotype, or both the V/F$^{158}$ genotype, the H/H$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the H/H$^{131}$ genotype, or both the F/F$^{158}$ genotype, the H/H$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the H/R$^{131}$ genotype, or both the V/V$^{158}$ genotype, the H/R$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the H/R$^{131}$ genotype, or both the V/F$^{158}$ genotype, the H/R$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the H/R$^{131}$ genotype, or both the F/F$^{158}$ genotype, the H/R$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the R/R$^{131}$ genotype, or both the V/V$^{158}$ genotype, the R/R$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the R/R$^{131}$ genotype, or both the V/F$^{158}$ genotype, the R/R$^{131}$ genotype for treatment with the antibody based on the genotype determination of steps (i), (ii) or (iii); and (c) administering the antibody to the patient selected in step (b).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the R/R$^{131}$ genotype, or both the F/F$^{158}$ genotype, the R/R$^{131}$ genotype for treatment with the antibody based on the genotype determination of steps (i), (ii) or (iii); and (c) administering the antibody to the patient selected in step (b).

Methods are provided for treating a patient with an antibody by (a) selecting a patient with an FcγRIIIa V/V$^{158}$ genotype, a FcγRIIa H/H$^{131}$ genotype; or both a FcγRIIIa V/V$^{158}$ genotype and a FcγRIIa H/H$^{131}$ genotype and (b) administering the antibody to the patient selected in step (a).

Methods are provided for treating a patient with an antibody by (a) selecting a patient with an FcγRIIIA V/F$^{158}$ genotype, an FcγRIIA H/H$^{131}$ genotype; or both a FcγRIIIA V/F$^{158}$ genotype and an FcγRIIA H/H$^{131}$ genotype and (b) administering the antibody to the patient selected in step (a).

Methods are provided for treating a patient with an antibody by (a) selecting a patient with an FcγRIIIA F/F$^{158}$ genotype, or a FcγRIIA H/H$^{131}$ genotype; or both a FcγRIIIA F/F$^{158}$ genotype and a FcγRIIA H/H$^{131}$ genotype and (b) administering the antibody to the patient selected in step (a).

Methods are provided for treating a patient with an antibody by (a) selecting a patient with an FcγRIIIA V/V$^{158}$ genotype, an FcγRIIA H/R$^{131}$ genotype; or both an FcγRIIIA V/V$^{158}$ genotype and an FcγRIIA H/R$^{131}$ genotype and (b) administering the antibody to the patient selected in step (a).

Methods are also provided for treating a patient with an antibody by (a) selecting a patient with an FcγRIIIA V/F$^{158}$ genotype, an FcγRIIA H/R$^{131}$ genotype, or both an FcγRIIIA V/F$^{158}$ genotype and an FcγRIIA H/R$^{131}$ genotype and (b) administering the antibody to the patient selected in step (a).

Methods are provided for treating a patient with an antibody by (a) selecting a patient with an FcγRIIIA F/F$^{158}$ genotype, an FcγRIIA H/R$^{131}$ genotype, or both an FcγRIIIA F/F$^{158}$ genotype and an FcγRIIA H/R$^{131}$ genotype and (b) administering the antibody to the patient selected in step (a).

Methods are provided for treating a patient with an antibody by (a) selecting a patient with an FcγRIIIA V/V$^{158}$ genotype, an FcγRIIA R/R$^{131}$ genotype, or both an FcγRIIIA V/V$^{158}$ genotype and an FcγRIIA R/R$^{131}$ genotype and (b) administering the antibody to the patient selected in step (a).

Methods are also provided for treating a patient with an antibody by (a) selecting a patient with an FcγRIIIA V/F$^{158}$ genotype, an FcγRIIA R/R$^{131}$ genotype, or both an FcγRIIIA V/F$^{158}$ genotype and an FcγRIIA R/R$^{131}$ genotype and (b) administering the antibody to the patient selected in step (a).

Methods are provided for treating a patient with an antibody, comprising: (a) selecting a patient with an FcγRIIIA F/F$^{158}$ genotype, an FcγRIIA R/R$^{131}$ genotype, or both an FcγRIIIA F/F$^{158}$ genotype and an FcγRIIA R/R$^{131}$ genotype and (b) administering the antibody to the patient selected in step (a).

Methods are also provided for classifying a subject having an ADCC-treatable disease or disorder into one of more than three categories of responsiveness to an antibody therapy by genotyping subjects for a FcγRIIA polymorphism and a FcγRIIIA polymorphism, wherein the subjects have or had the ADCC-treatable disease or disorder and are or were administered antibody therapy for the disease or disorder; classifying each subject based on its FcγRIIA polymorphism and FcγRIIIA polymorphism to one of three or more categories of responsiveness to the antibody therapy; genotyping the subject for an FcγRIIA polymorphism and a FcγRIIIA polymorphism; identifying a genotype from (a) that is identical to the genotype from the subject in step (c), wherein the subject is classified into a category of responsiveness to the antibody therapy for the disease or disorder corresponding with a subject having an identical FcγRIIA polymorphism and an identical FcγRIIIA polymorphism.

Methods are provided for determining the degree of responsiveness that a subject having an ADCC-treatable disease or disorder will have to an antibody therapy for the disease or disorder by genotyping the subject for an FcγRIIA polymorphism and a FcγRIIIA polymorphism; and identifying a genotype associated with a particular degree of responsiveness to the antibody therapy from a reference that is identical to the genotype from the test subject, wherein the test subject is determined to have a degree of responsiveness to the antibody therapy for the disease or disorder corresponding to the level of responsiveness associated with the reference having an identical FcγRIIA polymorphism and an identical FcγRIIIA polymorphism.

Methods are also provided for determining the degree of responsiveness that a test subject having an ADCC-treatable disease or disorder will have to an antibody therapy for the disease or disorder by (a) genotyping subjects for a FcγRIIA polymorphism and a FcγRIIIA polymorphism, wherein the subjects have or had the ADCC-treatable disease or disorder and are or were administered antibody therapy for the disease or disorder; (b) classifying each subject based on its FcγRIIA polymorphism and FcγRIIIA polymorphism to one of more than three categories of responsiveness to the antibody therapy; (c) genotyping the test subject for an FcγRIIA polymorphism and a FcγRIIIA polymorphism; and (d) identifying a genotype from (a) that is identical to the genotype from the test subject in step (c), wherein the test subject is determined to have a degree of responsiveness to the antibody therapy for the disease or disorder corresponding to the level of responsiveness associated with a subject having an identical FcγRIIA polymorphism and an identical FcγRIIIA polymorphism.

Also provided are kits for use in determining responsiveness to an antibody therapy in a patient which include an element for genotyping the sample to identify a FcγRIIA polymorphism; an element for genotyping the sample to identify a FcγRIIIA polymorphism; and a reference that correlates a genotype in the patient with one of more than three predicted therapeutic responses to the antibody therapy.

Methods are provided for selecting a specific variant antibody therapy from a set of two or more variant antibody therapies for use in treatment of subjects having an ADCC-treatable disease by genotyping the subjects for an FcγRIIA polymorphism and a FcγRIIIA polymorphism, classifying the subjects into one of more than three categories of responsiveness based on their FcγRIIA polymorphism and their FcγRIIIA polymorphism, and selecting a specific variant antibody therapy for the subjects such that the degree of responsiveness to the antibody therapy in the subjects is improved from the degree of responsiveness obtained with another variant antibody.

Methods are also provided for treating an ADCC-treatable disease or disorder in a subject by genotyping the subject for an FcγRIIA polymorphism and an FcγRIIIA polymorphism, classifying the subject into one of more than three categories of therapeutic responsiveness to an antibody therapy based on the FcγRIIA polymorphism and the FcγRIIIA polymorphism, selecting an antibody with a preferred degree of therapeutic responsiveness from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function, and administering a therapeutically effective amount of the antibody to the subject, wherein, the antibody treats the ADCC-treatable disease or disorder in the subject.

Methods are provided for making a set of related antibodies capable of modulating the responsiveness of a subject having an ADCC-treatable disease or disorder to an antibody therapy for the disease or disorder by modifying the amino acid sequence of at least one amino acid residue in a parent antibody, such that the modified parent antibody exhibits enhanced binding affinity to at least one Fc receptor encoded by an Fc receptor gene of a first genotype, compared to the Fc binding affinity of the parent antibody, to generate a first variant antibody; and modifying at least one amino acid residue in a parent antibody, such that the modified parent antibody exhibits enhanced binding affinity to at least one Fc receptor encoded by an Fc receptor gene of a second genotype, compared to the Fc binding affinity of the parent antibody, to generate a second variant antibody, wherein the first and second variant antibodies have the same antigen specificity and are capable of modulating the responsiveness of a subject having an ADCC-treatable disease or disorder to an antibody therapy for the disease or disorder.

Methods are provided for generating a set of variant antibodies capable of modulating the responsiveness of a subject having an ADCC-treatable disease or disorder to an antibody therapy for the disease or disorder by amplifying a nucleic acid comprising a nucleotide sequence encoding a region of an antibody, wherein the amplifying is carried out with a set of primers that encode all nineteen amino acid variants at a single residue of the region, to generate a set of variant nucleic acids encoding nineteen amino acid substitution variants at the single residue of the region, transcribing and translating each of the variant nucleic acids in vitro, to generate a set of variants, and/or selecting from the set an variant having altered FcR binding activity compared to a reference region, generating a set of selected variants, wherein the first and second variant antibodies have the same antigen specificity and are capable of modulating the responsiveness of a subject having an ADCC-treatable disease or disorder to an antibody therapy for the disease or disorder. In some embodiments, the method includes determining in vitro ADCC activity of the selected variant.

Methods are also provided for modulating the responsiveness of a subject having an ADCC-treatable disease or disorder to an antibody therapy for the disease or disorder by genotyping the subject for an FcγRIIA polymorphism and an FcγRIIIA polymorphism, classifying the subject into one of more than three categories of therapeutic responsiveness to an antibody therapy based on the FcγRIIA polymorphism and the FcγRIIIA polymorphism, selecting an antibody from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function, and administering a therapeutically effective amount of the antibody to the subject, wherein the antibody modulates the responsiveness of the subject having an ADCC-treatable disease or disorder to an antibody therapy for the disease or disorder.

Methods are provided for enhancing antibody dependent cell mediated cytotoxicity (ADCC) activity of an antibody for use in treatment of a subject having an ADCC-treatable disease by genotyping the subject for an FcγRIIA polymorphism and a FcγRIIIA polymorphism, selecting an Fc nucleotide sequence for the antibody that has optimal ADCC for the FcγRIIA polymorphism and FcγRIIIA polymorphism, and modifying the antibody to include the optimal Fc sequence for the subject's genotype, wherein the ADCC activity of the antibody is enhanced by using the optimal Fc.

BRIEF DESCRIPTION OF THE DRAWINGS

FIGS. 5, 6, 7, 8, 9, 10 and 11 provide Tables 1 to 7 referred to in the Experimental Section, below.

FIGS. 12A-D: Amino acid sequences of Fc receptors and IgGs. FIG. 12A depicts an amino acid sequence alignment of FcγRIIIA (SEQ ID NO:26) and FcγRIIA (SEQ ID NO:27) from residues 83-170. Identical residues between the receptors are aligned, and the FcR residues that contact FcI are in bold. According to the numbering system used in crystal structure studies, the Valine at position 155 of FcγRIIIA is the residue referred to herein as V$^{158}$. The residues H/R$^{131}$ and V/I$^{158}$ are underlined. FIG. 12B depicts an amino acid sequence of hIgG1 from residues 229-444 (SEQ ID NO:34). Key binding motifs in the Fc region are in bold. FIG. 12C depicts a structure-based sequence alignment of FcγRIII (FcγR1—SEQ ID NO:36, SEQ ID NO: 37, SEQ ID NO:38; FcγRIIa-HR—SEQ ID NO: 39, SEQ ID NO: 40, and SEQ ID NO: 41; FcγRIIa-LR—SEQ ID NO: 42, SEQ ID NO: 43, and SEQ ID NO: 44; FcγRIIb—SEQ ID NO: 45, SEQ ID NO: 46, and SEQ ID NO: 47; FcγRIa—SEQ ID NO: 48, SEQ ID NO: 49, and SEQ ID NO: 50; FcγRIII-V—SEQ ID NO: 51, SEQ ID NO: 52, and SEQ ID NO: 53; and FcγRIII-F—SEQ ID NO: 54, SEQ ID NO: 55, and SEQ ID NO: 56) and hIgG1 (IgG$_1$—SEQ ID NO: 57, SEQ ID NO: 58, and SEQ ID NO: 59; IgG$_2$—SEQ ID NO: 60 SEQ ID NO: 61 and SEQ ID NO: 62. IgG$_3$—SEQ ID NO: 63 SEQ ID NO: 64 and SEQ ID NO: 65. IgG$_4$—SEQ ID NO: 66 SEQ ID NO: 67 and SEQ ID NO: 68; IgE—SEQ ID NO: 69, SEQ ID NO: 70, and SEQ ID NO: 71) with their respective homologues. HR indicates high responders; LR indicates low responders. FcγRIIIA-V, V$^{158}$ allele; FcγRIIIA-F, F$^{158}$ allele. FIG. 12D depicts Fc Walking: This involves bi-directional scanning saturation mutagenesis of approximately 5-10 residues, one residue at a time, on both sides of the "binding" motifs of the hFc regions namely lower hinge region (SEQ ID NO:30), B/C loop (SEQ ID NO:31), C/E loop (SEQ ID NO:32), and the F/G loop (SEQ ID NO:33).

FIG. 13: Table depicting an analysis of FcγRIIIA and FcγRIIA polymorphisms in B-NHL patients.

FIG. 14: Table depicting prevalence of FcγRIIIA and FcγRIIA polymorphisms in B-NHL patients (Weng), healthy U.S. Caucasians (Lehrnbecher), healthy U.S. African Americans (Lehrnbecher) and healthy Norwegians (Torkildsen).

FIG. 15: Alignment of Antibody Fc Regions: Table comparing the nucleotide sequence of the Fc regions of RITUXAN® (rituximab) (SEQ ID NO:1), REMICADE® (infliximab) (SEQ ID NO:12), ERBITUX® (cetuximab) (SEQ ID NO:13), CAMPATH® (alemtuzumab) (SEQ ID NO:14 and HERCEPTIN® (trastuzumab) (SEQ ID NO:15) (Prepared with CLUSTAL W (1.83); Mismatches are indicated by the absence of a "*" underneath the alignment.

FIG. 16: SSM in rituximab V$_L$ CDR2 region (SEQ ID NO:18).

FIG. 18: Sequence Comparison of the Hinge Region of human IgG$_3$ and human IgG$_1$. Numbers correspond to those of IgG$_1$ Eu-residues 215 to 254 (Edelman et. al., *Proc. Natl. Acad. Sci. USA* 63:78, 1969). The IgG$_3$ hinge region (SEQ ID NO:24) is about 4 times larger than the counterpart region of IgG$_1$ (SEQ ID NO:25), IgG$_2$, and IgG$_4$. The insertion sequence of the IgG$_3$ hinge region consists of an N-terminal 17-residue segment followed by a 15-residue segment that is identically and consecutively repeated three times (Michaelsen et. al., J. Biol. Chem. 252:883, 1977).

DEFINITIONS

Figure 1:
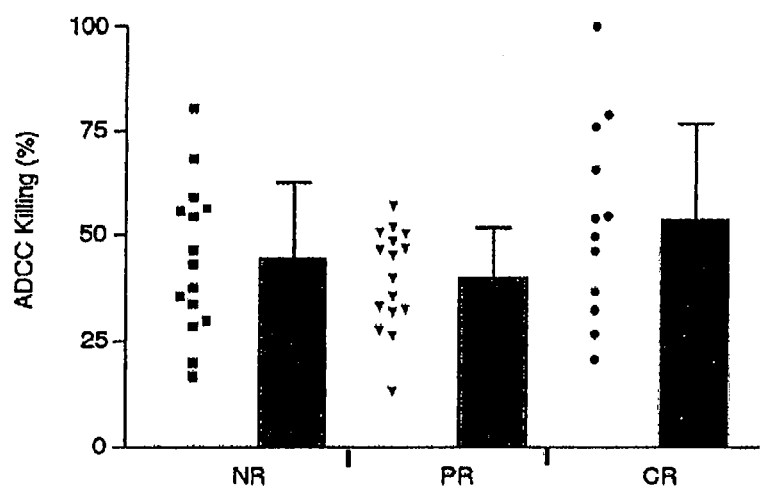
FIG. 1: Rituximab-induced antibody-dependent cell-mediated cytotoxicity (ADCC). The scatter plot in the left column of each Group represents the degree of rituximab-induced ADCC (effector/target ratio at 30:1) of individual tumors. The bars represent the mean and standard deviations in each Group. NR, nonresponder; PR, partial responder; CR, complete responder or complete response unconfirmed.

A polynucleotide has a certain percent "sequence identity" to another polynucleotide, meaning that, when aligned, that percentage of bases are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al., (1990), *J. Mol. Biol.* 215: 403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: *Computer Methods for Macromolecular Sequence Analysis* (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See, e.g., *Meth. Mol. Biol.* 70: 173-187 (1997). Also, the GAP program using the Needleman and Wunsch alignment method can be utilized to align sequences. See, e.g., *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. *Molecular Cloning: A Laboratory Manual, Second Edition*, Cold Spring Harbor Laboratory Press, Cold Spring Harbor (1989), particularly Chapter 11 and Table 11.1 therein; and Sambrook, J. and Russell, W., *Molecular Cloning: A Laboratory Manual, Third Edition*, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms.

Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (See, e.g., Sambrook et al., supra, 9.50-9.51). For hybridizations with shorter nucleic acids, i.e., oligonucleotides, the position of mismatches becomes more important, and the length of the oligonucleotide determines its specificity (See, e.g., Sambrook et al., supra, 11.7-11.8). In some embodiments, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

As used herein, the term "target nucleic acid region" or "target nucleic acid" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through hybridization and/or amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are in some embodiments of a length compatible with their use in synthesis of primer extension products, and are in some embodiments are in the range of between 8 nucleotides to 100 nucleotides in length, such as 10 to 75 nucleotides, 15 to 60 nucleotides, 15 to 40 nucleotides, 18 to 30 nucleotides, 20 to 40 nucleotides, 21 to 50 nucleotides, 22 to 45 nucleotides, or 25 to 40 nucleotides, and so on. In some embodiments, a primer has a length in the range of between 18-40 nucleotides, 20-35 nucleotides, or 21-30 nucleotides, and any length between the stated ranges. In some embodiments, primers are in the range of between 10-50 nucleotides long, such as 15-45 nucleotides long, 18-40 nucleotides long, 20-30 nucleotides long, 21-25 nucleotides long and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Primers are in some embodiments single-stranded for maximum efficiency in amplification, but may alternatively be double-stranded. If double-stranded, the primer is usually first treated to separate its strands before being used to prepare extension products. This denaturation step can be effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are in some embodiments of a length compatible with its use in specific detection of all or a portion of a target sequence of a target nucleic acid, and are in some embodiments in the range of between 8 nucleotides to 100 nucleotides in length, such as 8 to 75 nucleotides, 10 to 74 nucleotides, 12 to 72 nucleotides, 15 to 60 nucleotides, 15 to 40 nucleotides, 18 to 30 nucleotides, 20 to 40 nucleotides, 21 to 50 nucleotides, 22 to 45 nucleotides, or 25 to 40 nucleotides, and so on. In some embodiments, a probe has a length in the range of between 18-40 nucleotides, 20-35 nucleotides, or 21-30 nucleotides long, and any length between the stated ranges. In some embodiments, a probe is in the range of between 10-50 nucleotides long, such as 15-45 nucleotides, 18-40 nucleotides, 20-30 nucleotides, 21-28 nucleotides, or 22-25 nucleotides, and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

Exemplary stringent conditions typically will be those in which the salt concentration is at least about 0.01 to 1.0 M sodium ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above that the hybridization pattern is not appreciably altered and which provides adequate signal for the particular oligonucleotide probes of interest.

The term "assessing" includes any form of measurement, and includes determining if an element is present or not. The terms "determining," "measuring," "evaluating," "assessing," and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

As used herein, the term "ADCC-dependent antibody therapy" refers to a therapy involving use of antibody that comprises an antigen-binding domain and an Fc region that binds an FcR of a cytotoxic effector cell, where binding of the antibody to a target cell results in killing of the target cell via ADCC, and where killing of the target cell(s) provides for a therapeutic effect in an individual.

An "ADCC-treatable disease, condition, or disorder," as used herein, is a disease, condition, or disorder that is treated with a therapeutic antibody that mediates ADCC, thereby treating the disease, condition, or disorder. ADCC-treatable diseases, conditions, and disorders include, but are not limited to, a neoplastic disease; an autoimmune disease; a microbial infection; and allograft rejection.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the γ chain of the Fc receptor. Fc receptors are defined by their specificity for immunoglobulin subtypes. Fc receptors for IgG are referred to as FcγR, for IgE as FcεR, and for IgA as FcαR. Different accessory cells bear Fc receptors for antibodies of different isotype, and the isotype of the antibody determines which accessory cells will be engaged in a given response (Ravetch J. V. et al., *Annu. Rev. Immunol.* 19:275-90, 2001).

FcγRs, designated FcγRI (CD64), FcγRII (CD32), and FcγRIII (CD16), are encoded by distinct genes although they share extensive sequence homology.

FcγRII (CD32) is a 40 KDa integral membrane glycoprotein which binds complexed IgG; and exhibits only low affinity for monomeric Ig (appr. $10^6$ $M^{-1}$). FcγRII is the most widely expressed FcγR, present on all hematopoietic cells, including monocytes, macrophages, B cells, NK cells, neutrophils, mast cells, and platelets (Cohen-Solal et al., *Immunol. Lett.* 92:199-205, 2004). FcγRII has only two immunoglobulin-like regions in its immunoglobulin binding chain and hence a much lower affinity for IgG than FcγRI. There are three human FcγRII genes (FcγRIIA, FcγRIIB, FcγRIIC), all of which bind IgG in aggregates or immune complexes. Distinct differences within the cytoplasmic domains of FcγRIIA and FcγRIIB create two functionally heterogeneous responses to receptor ligation. FcγRIIA initiates intracellular signaling leading to cell activation such as phagocytosis and respiratory burst, whereas FcγRIIB initiates inhibitory signals leading to the inhibition of B-cell activation.

FcγRIII (CD16) is a Type-I membrane protein that exists as two isoforms: FcγRIIIA and FcγRIIIB. Both FcγRIIIA and FcγRIIIB are low affinity receptors. FcγRIIIA, an activating receptor, is expressed on NK cells, macrophages, monocytes, and dendritic cells; FcγRIIIB, an inhibitory form, is expressed on neutrophils. All FcγRs bind the same region on IgG Fc, yet with differing high (FcγRI) and low (FcγRII and FcγRIII) affinities (Sondermann et al., *J. Mol. Biol.* 309:737-749, 2001).

As used herein, the terms "treatment," "treating," and the like, refer to obtaining a desired pharmacological and/or physiological effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

The terms "individual," "host," "subject," and "patient," used interchangeably herein, refer to a mammal, including primates, rodents, livestock, pets, horses, etc. In some embodiments, an individual is a human.

A "functional Fc region" possesses an "effector function" of a native Fc region, e.g., ADCC activity. Although the boundaries of the Fc region of an immunoglobulin heavy chain may vary, the human IgG heavy chain Fc region is usually defined to stretch from an amino acid residue at position Cys226, or from Pro230, to the carboxyl-terminus. The Fc region of an immunoglobulin generally comprises two constant domains, CH2 and CH3. A "native Fc region sequence" comprises an amino acid sequence identical to the amino acid sequence of an Fc region found in nature. Native human Fc region sequences include, but are not limited to, the human IgG1 Fc region (non-A and A allotypes); human IgG2 Fc region; human IgG3 Fc region; and human IgG4 Fc region as well as naturally occurring variants thereof.

The term "Fc Walking" as used herein refers to an antibody engineering procedure by which the amino acid residues in the Fc region are selectively mutated around one or more of the lower hinge region, B/C loop, C'/E loop, and the F/G loop. Fc Walking involves bi-directional mutagenesis of approximately 5-10 residues, one residue at a time, on both sides of the Fc-FcR "binding" motifs with an objective of enhancing the Fc-FcR binding affinity and the ADCC activity of IgG variants. As an example, Fc Walking would cover the sequence stretch, $L^{234}$-$S^{239}$, as well as the residues upstream ($C^{229}$-$E^{233}$) and downstream ($V^{240}$-$P^{245}$) of this stretch. One such antibody engineering procedure that can be employed for Fc Walking is in vitro scanning saturation mutagenesis.

The term "Fc variant antibody" refers to an antibody that differs in amino acid sequence by at least one amino acid, compared to a reference antibody (where a reference antibody is also referred to as a "parent antibody"). In some embodiments, the Fc variant antibody is a monoclonal antibody (MAb); in these embodiments, the Fc variant antibody is referred to as an "Fc variant MAb." An Fc variant antibody may have altered FcR binding properties (e.g., enhanced FcR binding affinity), and/or altered ADCC activity, and/or altered effector function.

The term "enhanced affinity" is used to denote the significant increase in binding of the Fc variant antibody to one or more FcRs, compared to the binding affinity of the parent antibody for the same FcR(s). An increase of 10% or more in binding affinity over the parent antibody is considered significant.

The terms "cancer," "neoplasm," "hyperproliferative cell," and "tumor" are used interchangeably herein to refer to cells which exhibit relatively autonomous growth, so that they exhibit an aberrant growth phenotype characterized by a significant loss of control of cell proliferation. Cancerous cells can be benign or malignant. Viral infections (e.g., HCV infection in B-cells) can lead to hyper(lympho)proliferative disorders.

As used herein, the term immunological binding refers to the non-covalent interactions that occur between an antibody molecule and an antigen for which the antibody is specific. It also refers to such interactions that occur between an antibody in its bound state to an antigen and an Fc receptor in an effector cell. The strength or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the on ($k_{on}$) and the off ($k_{off}$) rate constants can be determined by calculation of the concentrations and the actual rates of association and dissociation. The ratio of $k_{off}/k_{on}$ enables cancellation of all parameters not related to affinity and is thus equal to the dissociation constant $K_D$ (Davies et. al., *Ann. Rev. Biochem.* 59: 439, 1990).

The term "in vitro scanning saturation mutagenesis" (SSM; Monju™) refers to a novel antibody engineering procedure, analogous to somatic hypermutation in vivo, for exploring in vitro antibody affinity evolution. An amino acid residue of interest in a protein sequence is mutated to nineteen other possible substitutions, and its effect on the structure and function of the protein analyzed. Interesting single mutants can be used as a starting point for subsequent rounds of SSM at other sites, so that multiple mutations with synergistic effects on binding may be identified. This same sequential mutation approach should be useful to optimize properties such as affinity, potency, efficacy, altered specificity, reduced immunogenicity, and removal of proteolytic cleavage sites (Burks et. al., *Proc. Natl. Acad. Sci. USA* 94:412, 1997; Chen et. al., *Prot. Engg.* 12:349, 1999; U.S. Pat. No. 6,180,341).

The term "specifically binds to a protein" refers to a binding reaction, which is determinative of the presence of the protein in the presence of a heterogeneous population of proteins. Thus, under designated immunoassay conditions, the specified antibodies bind to a particular protein and do not bind in a significant amount to other proteins present in the sample. Specific binding to a protein under such conditions may require an antibody that is selected for its specificity for a particular protein (Harlow and Lane (1988), *Antibodies: A Laboratory Manual*, Cold Spring Harbor Publications, New York, N.Y.).

The terms "polypeptide", "peptide", or "protein" are used interchangeably herein to designate a linear sequence of amino acid residues by peptide bonds between the alpha amino and carboxyl Groups of adjacent residues. The amino acid residues are in many embodiments in the natural L-isomeric form. However, residues in the D-isomeric form can be substituted for any L-amino acid residue, as long as the desired functional property is retained by the polypeptide.

The term "binding polypeptide" refers to a polypeptide that specifically binds to a target molecule (for example, a cell receptor) in a manner analogous to the binding of an antibody to an antigen. Binding polypeptides can be derived from antibody genes or fragments of antibody genes. Thus, Fc fragment that binds to Fc receptor is an example of a binding polypeptide.

The substitutions, deletions, inversions, and/or insertions of amino acids in an antibody (e.g., in an Fc variant antibody) will occur in regions not essential to antigen binding. The identification of essential and non-essential amino acids in the antibody can be achieved by methods known in the art, such as by site-directed mutagenesis (for example, SSM) and AlaScan analysis (Moffison et. al., *Chem. Biol.* 5:302-307, 2001). Essential amino acids have to be maintained or replaced by conservative substitutions in the variants. Non-essential amino acids can be deleted, or replaced by a spacer or by conservative or non-conservative substitutions.

Antibody variants can be obtained by substitution of any of the amino acids present in the antibody. For example, Fc variant antibodies can be obtained by substitution of any of the amino acids present in the Fc fragment. As can be appreciated, there are positions in the sequence that are more tolerant to substitutions than others, and some substitutions can improve the binding activity of the parent antibody. The amino acids that are essential should either be identical to the amino acids present in the parent antibody, or substituted by conservative substitutions. The amino acids that are non-essential can be identical to those in the parent antibody, or can be substituted by conservative or non-conservative substitutions, and/or can be deleted.

The term "conservative substitution" is used in reference to proteins or peptides to reflect amino acid substitutions that do not substantially alter the activity (specificity or binding affinity) of the molecule. Where the side-chain of the amino acid to be replaced is either polar or hydrophobic, the conservative substitution should be with a naturally or non-naturally occurring amino acid that is also polar or hydrophobic. Conservative amino acid substitutions generally involve substitution of one amino acid for another amino acid with similar chemical properties (e.g. charge or hydrophobicity). The following six Groups each contain amino acids that are typical conservative substitutions for one another: [1] Alanine (A), Serine (S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W).

A non-conservative substitution is a substitution in which the substituting amino acid (naturally or non-naturally occurring) has significantly different size, configuration and/or electronic properties compared to the amino acid being substituted. Thus, the side chain of the substituting amino acid can be significantly lower (or smaller) than the side chain of the native amino acid being substituted and/or can have functional groups with significantly different electronic properties than the amino acid being substituted.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated.

Specifically, degenerate codon substitutions may be achieved by generating sequences in which the third position of one or more selected (or all) codons is substituted with mixed-base and/or deoxyinosine residues (Batzer et. al., *Nucleic Acid Res.* 19:5081, 1991; Ohtsuka et. al., *J. Biol. Chem.* 260:2605, 1985). The term nucleic acid is used interchangeably with gene, cDNA, and the mRNA encoded by a gene.

The term "heterologous nucleic acid" refers to a nucleic acid that is not native to the cell in which it is found.

The term "detectable label" refers to any material having a detectable physical or chemical property. Such detectable labels have been well established in the field of immunoassays. Thus, a label is any composition detectable by spectroscopic, photochemical, biochemical, immunochemical, electrical, optical or chemical means. Useful labels in the present disclosure include magnetic beads (for example, DYNABEADS™), fluorescent dyes (example, fluorescein isothiocyanate, rhodamine), enzymes (example, β-galactosidase, chloramphenicol acetyltransferase, horse radish peroxidase, alkaline phosphatase and others, commonly used as detectable enzymes, either as marker gene products or in an enzyme-linked immunosorbent assay (ELISA). Those detectable labels that can be encoded by nucleic acids are referred to as 'reporter genes' or 'reporter gene products'.

Functional or active regions of the antibody or antibody fragment may be identified and/or improved by mutagenesis of a specific region of the protein, followed by expression and testing of the expressed polypeptide. For example, amino acid sequence variants of antibodies or antibody fragments can be generated and those that display equivalent or improved affinity for antigen can be identified using standard techniques and/or those described herein. One such example is generation of an Fc variant region with an improved affinity for FcγRIIIA comprising F/F$^{158}$ allele. Methods for generating amino acid sequence variants are readily apparent to a skilled practitioner in the art and can include site-specific mutagenesis, directed evolution technologies (U.S. Pat. No. 6,180, 341) or random mutagenesis (e.g., by PCR) of the nucleic acid encoding the antibody or antibody fragment (Zoller, M. J. *Curr. Opinion in Biotechnol.* 3:348-354, 1992). Both naturally occurring and non-naturally occurring amino acids may be used to generate amino acid sequence variants of the antibodies and antibody fragments of the disclosure.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical residue (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (See, e.g., below) is calculated using default gap weights. Sequences corresponding to the antibodies in the present disclosure may comprise at least about 70% sequence identity to the sequence of the antibody deposited in GenBank, preferably about 75%, 80% or 85% or more preferably, about 90% or 95% or more identity.

Homology or identity is determined by BLAST (Basic Local Alignment Search Tool) analysis using the algorithm employed by the programs blastp, blastn, blastx, tblastn and tblastx (Karlin et al. (1990), Proc Natl Acad Sci USA 87:2264-2268 and Altschul (1993), J Mol Evol 36:290-300) which are tailored for sequence similarity searching. The approach used by the BLAST program is first to consider similar segments between a query sequence and a database sequence, then to evaluate the statistical significance of all matches that are identified and finally to summarize only those matches which satisfy a preselected threshold of significance. For a discussion of basic issues in similarity searching of sequence databases, See, e.g., Altschul et al. (1994), Nat Genet. 6:119-129). The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al. (1992), Proc Natl Acad Sci USA 89:10915-10919). Four blastn parameters were adjusted as follows: Q=10 (gap creation penalty); R=10 (gap extension penalty); wink=-1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

DETAILED DESCRIPTION

Methods and compositions are provided for determining whether a subject suffering from a neoplastic condition is responsive to an antineoplastic therapy, such as antibody therapy, e.g., Rituximab therapy. In practicing the subject methods, the subject is genotyped to determine whether the subject has at least one favorable FcγR polymorphism, e.g., the $H/H^{131}$ genotype in FcγRIIA or the $V/V^{151}$ genotype in FcγRIIIA. In addition, reagents, devices and kits thereof that find use in practicing the subject methods are provided.

Methods and compositions are provided for determining whether a subject suffering from a neoplastic condition is responsive to an antineoplastic therapy, such as antibody therapy, e.g., rituximab therapy. In practicing the subject methods, the subject is genotyped to determine whether the subject has at least one favorable FcγR polymorphism, e.g., the $H/H^{131}$ genotype in FcγRIIA or the $V/V^{158}$ genotype in FcγRIIIA. In addition, reagents, devices and kits thereof, that find use in practicing the subject methods are provided.

Methods are provided for determining the degree of responsiveness that a subject having an ADCC-treatable disease or disorder will have to an antibody therapy for the disease or disorder by genotyping the subject for an FcγRIIA polymorphism to obtain a first result, genotyping the subject for an FcγRIIIA polymorphism to obtain a second result, assigning the subject to one of more than three categories of treatment response and/or employing the first and second results to determine the degree of the responsiveness of the subject to the antibody therapy.

For example, the FcγRIIA polymorphism can be the $H/R^{131}$ polymorphism and the FcγRIIIA polymorphism can be the $V/F^{158}$ polymorphism.

In some embodiments, the presence of both a $H/H^{131}$ genotype and a $V/V^{158}$ genotype indicates a high degree of treatment response to the antibody therapy. In other embodiments, the identification of i) a $H/H^{131}$ genotype and ii) a $V/F^{158}$ or a $F/F^{158}$ genotype indicates an intermediate degree of treatment response to the antibody therapy. In yet another embodiment, the identification of i) a $V/V^{158}$ genotype and ii) a $H/R^{131}$ or a $R/R^{131}$ genotype indicates an intermediate degree of treatment response to the antibody therapy. In some embodiments, the identification of: i) a $V/F^{158}$ genotype and a $H/R^{131}$ genotype; ii) a 158 V/F genotype and a $R/R^{131}$ genotype; iii) a $F/F^{158}$ genotype and a $H/R^{131}$ genotype; or iv) a $F/F^{158}$ genotype and a $R/R^{131}$ genotype indicates a low degree of treatment response to the antibody therapy.

In some embodiments, the ADCC-treatable disease or disorder may be a neoplastic disease, an autoimmune disease, a microbial infection, or an allograft rejection. In other embodiments, the ADCC-treatable disease or disorder is a neoplastic disease. In another embodiment, the neoplastic disease is non-Hodgkin's lymphoma (NHL), e.g., follicular lymphoma.

In some embodiments, the antibody therapy includes the use of a therapeutic antibody or mimetic thereof that specifically binds to CD20. In other embodiments, the therapeutic antibody is a monoclonal antibody, e.g. rituximab.

In some embodiments, the methods include developing patient-group specific Fc variant antibodies based on the first and second results such that the therapeutic response rate of the patient group to the antibody therapy is improved.

Methods are provided for selecting a specific Fc variant antibody therapy from a set of two or more Fc variant antibody therapies for use in treating subjects having an ADCC-treatable disease by genotyping the subjects for an FcγRIIA polymorphism to classify patient population into three groups (e.g., $H/H^{131}$, $H/R^{131}$, $R/R^{131}$), genotyping the subjects for an FcγRIIIA polymorphism to classify patient population into three groups (e.g., $V/V^{158}$, $V/F^{158}$, $F/F^{158}$), classifying the subjects into nine patient groups I-IX based on the first and second results, and employing the first and second results to select a specific Fc variant antibody therapy for the patient group such that the degree of treatment response to antibody therapy in the patient group is improved.

For example, the FcγRIIA polymorphism can be the $H/R^{131}$ polymorphism and the FcγRIIIA polymorphism can be the $V/F^{158}$ polymorphism.

In some embodiments, the genotyping may identify a $H/H^{131}$ genotype and a $V/V^{158}$ genotype. In this embodiment, the Fc variant antibody may be selected for enhanced binding and/or in vitro ADCC function to at least one of an FcγRIIA including a H/H$^{131}$ allele and an FcγRIIIA including a V/V$^{158}$ allele.

In other embodiments, the genotyping may identify a H/H$^{131}$ genotype and a V/F$^{158}$ genotype. In this embodiment, the Fc variant antibody can be selected for enhanced binding and/or in vitro ADCC function to at least one of an FcγRIIA including a H/H$^{131}$ allele and an FcγRIIIA including a V/F$^{158}$ allele.

In some embodiments, the genotyping may identify a H/H$^{131}$ genotype and a F/F$^{158}$ genotype. In this embodiment, the Fc variant antibody may be selected for enhanced binding and/or in vitro ADCC function to at least one of an FcγRIIA including a H/H$^{131}$ allele and an FcγRIIIA including a F/F$^{158}$ allele.

In other embodiments, the genotyping may identify a V/F$^{158}$ genotype and a H/R$^{131}$ genotype. In this embodiment, the Fc variant antibody may be selected for enhanced binding and/or in vitro ADCC function to at least one of an FcγRIIA including a H/R$^{131}$ allele and an FcγRIIIA including a V/F$^{158}$ allele.

In other embodiments, the genotyping may identify a V/F$^{158}$ genotype and a R/R$^{131}$ genotype. In this embodiment, the Fc variant antibody may be selected for enhanced binding and/or in vitro ADCC function to at least one of an FcγRIIA including a R/R$^{131}$ allele and an FcγRIIIA including a V/F$^{158}$ allele.

In other embodiments, the genotyping may identify a F/F$^{158}$ genotype and a H/R$^{131}$ genotype. In this embodiment, the Fc variant antibody may be selected for enhanced binding and/or in vitro ADCC function to at least one of an FcγRIIA including a H/R$^{131}$ allele and an FcγRIIIA including a F/F$^{158}$ allele.

In some embodiments, the genotyping may identify a F/F$^{158}$ genotype and a R/R$^{131}$ genotype. In this embodiment, the Fc variant antibody can be selected for enhanced binding and/or in vitro ADCC function to at least one of an FcγRIIA including a R/R$^{131}$ and an FcγRIIIA including a F/F$^{158}$ allele In other embodiments, the genotyping may identify a V/V$^{158}$ genotype and a H/R$^{131}$ genotype. In this embodiment, the Fc variant antibody may be selected for enhanced binding and/or in vitro ADCC function to at least one of an FcγRIIA including a H/R$^{131}$ allele and an FcγRIIIA including a V/V$^{158}$ allele.

In other embodiments, the genotyping may identify a V/V$^{158}$ genotype and a R/R$^{131}$ genotype. In this embodiment, the Fc variant antibody may be selected for enhanced binding and/or in vitro ADCC function to at least one of an FcγRIIA including a R/R$^{131}$ allele and an FcγRIIIA including a V/V$^{158}$ allele.

In some embodiments, the ADCC-treatable disease or disorder may be a neoplastic disease, an autoimmune disease, a microbial infection, or an allograft rejection.

In some embodiments, the ADCC-treatable disease or disorder may be a neoplastic disease, an autoimmune disease, a microbial infection, or an allograft rejection. In some embodiments, the ADCC-treatable disease or disorder is a neoplastic disease. In other embodiments, the neoplastic disease is non-Hodgkin's lymphoma (NHL), e.g., follicular lymphoma.

In some embodiments, the antibody therapy includes the use of a therapeutic antibody or mimetic thereof that specifically binds to CD20. In other embodiments, the therapeutic antibody is a monoclonal antibody.

In other embodiments, the monoclonal antibody may include one or more amino acid substitutions compared to rituximab, wherein the one or more amino acid substitutions provide for enhanced binding and/or in vitro ADCC function to at least one of an FcγRIIA comprising H/R$^{131}$ or R/R$^{131}$ alleles, and an FcγRIIIA comprising V/F$^{158}$ or F/F$^{158}$ alleles.

Methods are also provided for making a set of related antibodies by modifying the amino acid sequence of at least one Fc region amino acid residue in a parent antibody, such that the modified Fc region exhibits enhanced binding affinity to at least one Fc receptor encoded by an Fc receptor gene of a first genotype, compared to the Fc binding affinity of the parent antibody, to generate a first Fc variant antibody; and/or modifying at least one Fc region amino acid residue in a parent antibody, such that the modified constant region exhibits enhanced binding affinity to at least one Fc receptor encoded by an Fc receptor gene of a second genotype, compared to the Fc binding affinity of the parent antibody, to generate a second Fc variant antibody, wherein the first and second Fc variant antibodies have the same antigen specificity.

For example, the first and the second Fc variant antibodies can have one or more amino acid residue modifications in one or more locations of a lower hinge region, a CH2 domain, and/or a CH3 domain.

In some embodiments, the wild-type antibody is a therapeutic antibody used in therapy of an ADCC-treatable disease or disorder. In some embodiments, the wild-type antibody is a therapeutic antibody used in therapy of a neoplastic disease. In another embodiment, the neoplastic disease is non-Hodgkin's lymphoma (NHL), e.g., follicular lymphoma.

In some embodiments, the ADCC-treatable disease or disorder may be a neoplastic disease, an autoimmune disease, a viral infection, a parasitic infection, or an allograft rejection.

In some embodiments, the first and second Fc variant antibodies bind specifically binds to CD20. In some embodiments, the first and second Fc variant antibodies are monoclonal antibodies, e.g., rituximab.

Also provided are kits for use in determining responsiveness to an antibody therapy in a patient which include an element for genotyping a sample to identify a FcγRIIA polymorphism, an element for genotyping the sample to identify a FcγRIIIA polymorphism, or an element for genotyping the sample to identify a FcγRIIIA polymorphism and an FcγRIIA, and a reference that correlates a genotype with predicted therapeutic response to a therapeutic antibody.

In some embodiments, the FcγRIIA genotype may be a H/H$^{131}$ genotype and the FcγRIIIA genotype may be a V/V$^{158}$ genotype. In this embodiment, the reference indicates a high degree of responsiveness to the therapeutic antibody.

In other embodiments, the FcγRIIA genotype may be a H/H$^{131}$ genotype and the FcγRIIIA genotype may be a V/F$^{158}$ or a F/F$^{158}$ genotype. In this embodiment, the reference indicates an intermediate degree of responsiveness to the therapeutic antibody.

In another embodiment, the FcγRIIIA genotype is a V/V$^{158}$ genotype and the FcγRIIA genotype is a H/R$^{131}$ or a R/R$^{131}$ genotype. In this embodiment, the reference indicates an intermediate degree of responsiveness to the reference therapeutic antibody.

In some embodiments, the reference may indicate choosing an Fc variant antibody that exhibits enhanced binding to an FcγRIIA and/or an FcγRIIIA that exhibits enhanced in vitro ADCC function.

In some embodiments, the genotype is a V/F$^{158}$ genotype and a H/R$^{131}$ genotype, a V/F$^{158}$ genotype and a R/R$^{131}$ genotype, a F/F$^{158}$ genotype and a H/R$^{131}$ genotype, or a F/F$^{158}$ genotype and a R/R$^{131}$. In this embodiment, the reference indicates a low degree of responsiveness to the therapeutic antibody.

In some embodiments, the therapeutic antibody is used for treating an ADCC-treatable disease or disorder. In some embodiments, the ADCC-treatable disease or disorder may be a neoplastic disease, an autoimmune disease, a microbial infection, or an allograft rejection.

Methods are provided for of treating an ADCC-treatable disease or disorder in an individual by determining a category of therapeutic responsiveness to an antibody therapy by genotyping the individual for an FcγRIIA polymorphism and an FcγRIIIA polymorphism, wherein the FcγRIIA polymorphism and the FcγRIIIA polymorphism together indicate a degree of therapeutic responsiveness; selecting an antibody from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function; and administering an effective amount of the antibody to the individual.

In some embodiments, the genotyping may identify a $H/H^{131}$ genotype and a $V/V^{158}$ genotype. In this embodiment, the antibody is selected for binding to at least one of an FcγRIIA having a $H/H^{131}$ allele and an FcγRIIIA having a $V/V^{158}$ allele.

In other embodiments, the genotyping may identify an $H/H^{131}$ genotype and a $V/F^{158}$ or a $F/F^{158}$ genotype. In this embodiment, the antibody can be selected for binding to at least one of an FcγRIIA having a $His^{131}$ and an FcγRIIIA having a $Val^{158}$ or $F^{158}$.

In another embodiment, the genotyping may identify a $V/F^{158}$ genotype and a $H/R^{131}$ genotype; a $V/F^{158}$ genotype and a $R/R^{131}$ genotype; a $F/F^{158}$ genotype and a $H/R^{131}$ genotype; or a $F/F^{158}$ genotype and a $R/R^{131}$ genotype. In this embodiment, the antibody may be selected for binding to at least one of an FcγRIIA having a $Arg^{131}$ and an FcγRIIIA having a $Phe^{158}$.

In other embodiments, the genotyping may identify a $H/H^{131}$ genotype and a $V/F^{158}$ genotype. In this embodiment, the antibody may be an Fc variant antibody selected for enhanced binding and/or in vitro ADCC function to at least one of an FcγRIIA having a $H/H^{131}$ allele and an FcγRIIIA having a $V/F^{158}$ allele.

In some embodiment, the genotyping identifies a $H/H^{131}$ genotype and a $F/F^{158}$ genotype. In this embodiment, the antibody may be an Fc variant antibody selected for enhanced binding and/or in vitro ADCC function to at least one of an FcγRIIA having a $H/H^{131}$ allele and an FcγRIIIA having a $F/F^{158}$ allele.

In some embodiments, the genotyping may identify a $V/F^{158}$ genotype and a $H/R^{131}$ genotype. In this embodiment, the antibody can be an Fc variant antibody selected for enhanced binding and/or in vitro ADCC function to at least one of an FcγRIIA having a $H/R^{131}$ allele and an FcγRIIIA having a $V/F^{158}$ allele.

In some embodiments, the genotyping may identify a $V/F^{158}$ genotype and a $R/R^{131}$ genotype. In this embodiment, the antibody can be an Fc variant antibody selected for enhanced binding and/or in vitro ADCC function to at least one of an FcγRIIA having a $R/R^{131}$ allele and an FcγRIIIA having a $V/F^{158}$ allele.

In some embodiments, the genotyping may identify a $F/F^{158}$ genotype and a $H/R^{131}$ genotype. In this embodiment, the antibody can be an Fc variant antibody selected for enhanced binding and/or in vitro ADCC function to at least one of an FcγRIIA having a $H/R^{131}$ allele and an FcγRIIIA having a $F/F^{158}$ allele.

In some embodiments, the genotyping may identify a $F/F^{158}$ genotype and a $R/R^{131}$ genotype. In this embodiment, the antibody can be an Fc variant antibody selected for enhanced binding and/or in vitro ADCC function to at least one of an FcγRIIA having a $R/R^{131}$ and an FcγRIIIA having a $F/F^{158}$ allele.

In other embodiments, the genotyping may identify a $V/V^{158}$ genotype and a $H/R^{131}$ genotype. In this embodiment, the antibody may be an Fc variant antibody selected for enhanced binding and/or in vitro ADCC function to at least one of an FcγRIIA having a $H/R^{131}$ allele and an FcγRIIIA having a $V/V^{158}$ allele.

In some embodiments, the genotyping may identify a $V/V^{158}$ genotype and a $R/R^{131}$ genotype. In this embodiment, the antibody is an Fc variant antibody selected for enhanced binding and/or in vitro ADCC function to at least one of an FcγRIIA having a $R/R^{131}$ allele and an FcγRIIIA having a $V/V^{158}$ allele.

In some embodiments, the ADCC-treatable disease or disorder may be a neoplastic disease, an autoimmune disease, a microbial infection, or an allograft rejection.

Methods are provided for determining the degree of responsiveness to an antibody-dependent cell-mediated cytotoxicity antibody therapy by genotyping the subject for two or more Fcγ receptor polymorphisms and employing the first and second Fcγ receptor polymorphisms to determine the degree of the responsiveness of the subject to the antibody therapy.

In some embodiments, the Fcγ receptor polymorphisms include an FcγRIIA polymorphism and an FcγRIIIA polymorphism.

For example, an amino acid residue in the Fc region is selectively substituted by nineteen other natural amino acids.

Methods are also provided for generating a set of Fc variant antibodies by amplifying a nucleic acid comprising a nucleotide sequence encoding an Fc region of an antibody, wherein the amplifying is carried out with a set of primers that encode all nineteen amino acid variants at a single residue of the Fc region, to generate a set of variant nucleic acids encoding nineteen amino acid substitution variants at the single residue of the Fc region; transcribing and translating each of the variant nucleic acids in vitro, to generate a set of Fc variants; and/or c) selecting from the set an Fc variant having altered FcR binding activity compared to a reference Fc, generating a set of selected Fc variants.

In some embodiments, the methods include determining in vitro ADCC activity of the selected Fc variant.

In other embodiments, the methods include: d) repeating step (a) at a second residue of the Fc region, generating a second set of Fc variant; and/or e) repeating steps (b) and (c) on the second set, generating a second set of selected Fc variants.

In some embodiments, the transcribing and translating is carried out using a prokaryotic expression system.

In other embodiments, the Fc-encoding nucleotide sequence is under the transcriptional control of a phage promoter.

In some embodiments, FcR binding activity is assessed using an enzyme-linked immunosorbent assay.

Methods are also provided for selecting a patient for treatment with an antibody by (a) determining if the patient has (i.) an FcγRIIIA $V/V^{158}$ genotype, an FcγRIIIA $V/F^{158}$ or an FcγRIIIA $F/F^{158}$ genotype; or (ii.) determining if the patient has an FcγRIIA $H/H^{131}$ genotype, an FcγRIIA $H/R^{131}$ genotype or an FcγRIIA $R/R^{131}$ genotype, or (iii.) a FcγRIIIA $V/V^{158}$, FcγRIIA $H/H^{131}$ genotype, a FcγRIIIA $V/F^{158}$, FcγRIIA $H/H^{131}$ genotype, a FcγRIIIA $F/F^{158}$, FcγRIIA $H/H^{131}$ genotype, a FcγRIIIA $V/V^{158}$, FcγRIIA $H/R^{131}$ genotype, a FcγRIIIA $V/F^{158}$, FcγRIIA $H/R^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the H/H$^{131}$ genotype, or both the V/V$^{158}$ genotype, the H/H$^{131}$ genotype for treatment with the antibody based on the genotype determination of steps (i), (ii) or (iii); and (c) administering the antibody to the patient selected in step (b).

In some embodiments, the patient has a hyperproliferative disorder. In some embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the H/H$^{131}$ genotype, or both the V/F$^{158}$ genotype, the H/H$^{131}$ genotype for treatment with the antibody based on the genotype determination of steps (i), (ii) or (iii); and (c) administering the antibody to the patient selected in step (b).

In a some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the H/H$^{131}$ genotype, or both the F/F$^{158}$ genotype, the H/H$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the H/R$^{131}$ genotype, or both the V/V$^{158}$ genotype, the H/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the H/R$^{131}$ genotype, or both the V/F$^{158}$ genotype, the H/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the H/R$^{131}$ genotype, or both the F/F$^{158}$ genotype, the H/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/V$^{158}$ genotype, the R/R$^{131}$ genotype, or both the V/V$^{158}$ genotype, the R/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the V/F$^{158}$ genotype, the R/R$^{131}$ genotype, or both the V/F$^{158}$ genotype, the R/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for selecting a patient for treatment with an antibody by (a) determining if the patient has (i.) an FcγRIIIA V/V$^{158}$ genotype, an FcγRIIIA V/F$^{158}$ or an FcγRIIIA F/F$^{158}$ genotype; or (ii.) determining if the patient has an FcγRIIA H/H$^{131}$ genotype, an FcγRIIA H/R$^{131}$ genotype or an FcγRIIA R/R$^{131}$ genotype, or (iii.) a FcγRIIIA V/V$^{158}$, FcγRIIA H/H$^{131}$ genotype, a FcγRIIIA V/F$^{158}$, FcγRIIA H/H$^{131}$ genotype, a FcγRIIIA F/F$^{158}$, FcγRIIA H/H$^{131}$ genotype, a FcγRIIIA V/V$^{158}$, FcγRIIA H/R$^{131}$ genotype, a FcγRIIIA V/F$^{158}$, FcγRIIA H/R$^{131}$ genotype, a FcγRIIIA F/F$^{158}$, FcγRIIA H/R$^{131}$ genotype, a FcγRIIIA V/V$^{158}$, FcγRIIA R/R$^{131}$ genotype, a FcγRIIIA V/F$^{158}$, FcγRIIA R/R$^{131}$ genotype or a FcγRIIIA F/F$^{158}$, FcγRIIA R/R$^{131}$ genotype; (b) selecting the patient with the F/F$^{158}$ genotype, the R/R$^{131}$ genotype, or both the F/F$^{158}$ genotype, the R/R$^{131}$ genotype for treatment with the antibody based on the genotype determination of steps (i), (ii) or (iii); and (c) administering the antibody to the patient selected in step (b).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIa V/V$^{158}$ genotype, a FcγRIIa H/H$^{131}$ genotype; or both a FcγRIIIa V/V$^{158}$ genotype and a FcγRIIa H/H$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIA V/F$^{158}$ genotype, an FcγRIIA H/H$^{131}$ genotype; or both a FcγRIIIA V/F$^{158}$ genotype and an FcγRIIA H/H$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIA F/F$^{158}$ genotype, or a FcγRIIA H/H$^{131}$ genotype; or both a FcγRIIIA F/F$^{158}$ genotype and a FcγRIIA H/H$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIA V/V$^{158}$ genotype, an FcγRIIA H/R$^{131}$ genotype; or both an FcγRIIIA V/V$^{158}$ genotype and an FcγRIIA H/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for treating a patient with an antibody by (a) selecting a patient with an FcγRIIIA V/F$^{158}$ genotype, an FcγRIIA H/R$^{131}$ genotype, or both an FcγRIIIA V/F$^{158}$ genotype and an FcγRIIA H/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIA F/F$^{158}$ genotype, an FcγRIIA H/R$^{131}$ genotype, or both an FcγRIIIA F/F$^{158}$ genotype and an FcγRIIA H/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody by (a) selecting a patient with an FcγRIIIA V/V$^{158}$ genotype, an FcγRIIA R/R$^{131}$ genotype, or both an FcγRIIIA V/V$^{158}$ genotype and an FcγRIIA R/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for treating a patient with an antibody by (a) selecting a patient with an FcγRIIIA V/F$^{158}$ genotype, an FcγRIIA R/R$^{131}$ genotype, or both an FcγRIIIA V/F$^{158}$ genotype and an FcγRIIA R/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for treating a patient with an antibody, comprising: (a) selecting a patient with an FcγRIIIA F/F$^{158}$ genotype, an FcγRIIA R/R$^{131}$ genotype, or both an FcγRIIIA F/F$^{158}$ genotype and an FcγRIIA R/R$^{131}$ genotype and (b) administering the antibody to the patient selected in step (a).

In some embodiments, the patient has a hyperproliferative disorder. In other embodiments, the hyperproliferative disorder is cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are also provided for classifying a subject having an ADCC-treatable disease or disorder into one of more than three categories of responsiveness to an antibody therapy by genotyping subjects for a FcγRIIA polymorphism and a FcγRIIIA polymorphism, wherein the subjects have or had the ADCC-treatable disease or disorder and are or were administered antibody therapy for the disease or disorder; classifying each subject based on its FcγRIIA polymorphism and FcγRIIIA polymorphism to one of three or more categories of responsiveness to the antibody therapy; genotyping the subject for an FcγRIIA polymorphism and a FcγRIIIA polymorphism; identifying a genotype from (a) that is identical to the genotype from the subject in step (c), wherein the subject is classified into a category of responsiveness to the antibody therapy for the disease or disorder corresponding with a subject having an identical FcγRIIA polymorphism and an identical FcγRIIIA polymorphism.

In one embodiment, the subjects are classified into one of nine categories of responsiveness to the antibody therapy.

For example, the FcγRIIA polymorphism may be the H/R$^{131}$ polymorphism and the FcγRIIIA polymorphism may be the V/F$^{158}$ polymorphism.

In some embodiments, the presence of both a H/H$^{131}$ genotype and a V/V$^{158}$ genotype indicates a high degree of treatment response to the antibody therapy.

In other embodiments, the identification of i) a H/H$^{131}$ genotype and ii) a V/F$^{158}$ or a F/F$^{158}$ genotype indicates an intermediate degree of treatment response to the antibody therapy.

In other embodiments, the identification of i) a V/V$^{158}$ genotype and ii) a H/R$^{131}$ or a R/R$^{131}$ genotype indicates an intermediate degree of treatment response to the antibody therapy.

In some embodiments, the identification of: i) a V/F$^{158}$ genotype and a H/R$^{131}$ genotype; ii) a 158 V/F genotype and a R/R$^{131}$ genotype; iii) a F/F$^{158}$ genotype and a H/R$^{131}$ genotype; or iv) a F/F$^{158}$ genotype and a R/R$^{131}$ genotype indicates a low degree of treatment response to the antibody therapy.

In some embodiments, the ADCC-treatable disease or disorder may be a neoplastic disease, an autoimmune disease, a microbial infection, or an allograft rejection. In some embodiments, the ADCC-treatable disease or disorder may be a neoplastic disease. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Methods are provided for determining the degree of responsiveness that a subject having an ADCC-treatable disease or disorder will have to an antibody therapy for the disease or disorder by genotyping the subject for an FcγRIIA polymorphism and a FcγRIIIA polymorphism; and identifying a genotype associated with a particular degree of responsiveness to the antibody therapy from a reference that is identical to the genotype from the test subject, wherein the test subject is determined to have a degree of responsiveness to the antibody therapy for the disease or disorder corresponding to the level of responsiveness associated with the reference having an identical FcγRIIA polymorphism and an identical FcγRIIIA polymorphism.

In some embodiments, the subjects may be classified into one of nine categories of responsiveness to the antibody therapy.

In some embodiments, the FcγRIIA polymorphism is the $H/R^{131}$ polymorphism and the FcγRIIIA polymorphism is the $V/F^{158}$ polymorphism. In other embodiments, the presence of both a $H/H^{131}$ genotype and a $V/V^{158}$ genotype indicates a high degree of treatment response to the antibody therapy. In other embodiments, the identification of i) a $H/H^{131}$ genotype and ii) a $V/F^{158}$ or a $F/F^{158}$ genotype indicates an intermediate degree of treatment response to the antibody therapy. In other embodiments, the identification of i) a $V/V^{158}$ genotype and ii) a $H/R^{131}$ or a $R/R^{131}$ genotype indicates an intermediate degree of treatment response to the antibody therapy. In yet other embodiments, the identification of: i) a $V/F^{158}$ genotype and a $H/R^{131}$ genotype; ii) a 158 V/F genotype and a $R/R^{131}$ genotype; iii) a $F/F^{158}$ genotype and a $H/R^{131}$ genotype; or iv) a $F/F^{158}$ genotype and a $R/R^{131}$ genotype indicates a low degree of treatment response to the antibody therapy.

In some embodiments, the ADCC-treatable disease or disorder may be a neoplastic disease, an autoimmune disease, a microbial infection, or an allograft rejection. In some embodiments, the ADCC-treatable disease or disorder may be a neoplastic disease. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

For example, the reference may be an index including the genotypes for subjects that had an ADCC-treatable disease or disorder and were administered antibody therapy for the disease or disorder and wherein the subjects were classified into one of more than three categories of responsiveness to the antibody therapy.

Methods are also provided for determining the degree of responsiveness that a test subject having an ADCC-treatable disease or disorder will have to an antibody therapy for the disease or disorder by (a) genotyping subjects for a FcγRIIA polymorphism and a FcγRIIIA polymorphism, wherein the subjects have or had the ADCC-treatable disease or disorder and are or were administered antibody therapy for the disease or disorder; (b) classifying each subject based on its FcγRIIA polymorphism and FcγRIIIA polymorphism to one of more than three categories of responsiveness to the antibody therapy; (c) genotyping the test subject for an FcγRIIA polymorphism and a FcγRIIIA polymorphism; and (d) identifying a genotype from (a) that is identical to the genotype from the test subject in step (c), wherein the test subject is determined to have a degree of responsiveness to the antibody therapy for the disease or disorder corresponding to the level of responsiveness associated with a subject having an identical FcγRIIA polymorphism and an identical FcγRIIIA polymorphism.

For example, the subjects may be classified into one of nine categories of responsiveness to the antibody therapy.

For example, the FcγRIIA polymorphism may be the $H/R^{131}$ polymorphism and the FcγRIIIa polymorphism may be the $V/F^{158}$ polymorphism.

In some embodiments, the presence of both a $H/H^{131}$ genotype and a $V/V^{158}$ genotype indicates a high degree of treatment response to the antibody therapy. In other embodiments, the identification of i) a $H/H^{131}$ genotype and ii) a $V/F^{158}$ or a $F/F^{158}$ genotype indicates an intermediate degree of treatment response to the antibody therapy. In other embodiments, the identification of i) a $V/V^{158}$ genotype and ii) a $H/R^{131}$ or a $R/R^{131}$ genotype indicates an intermediate degree of treatment response to the antibody therapy. In other embodiments, the identification of: i) a $V/F^{158}$ genotype and a $H/R^{131}$ genotype; ii) a 158 V/F genotype and a $R/R^{131}$ genotype; iii) a $F/F^{158}$ genotype and a $H/R^{131}$ genotype; or iv) a $F/F^{158}$ genotype and a $R/R^{131}$ genotype indicates a low degree of treatment response to the antibody therapy.

In some embodiments, the ADCC-treatable disease or disorder may be a neoplastic disease, an autoimmune disease, a microbial infection, or an allograft rejection. In some embodiments, the ADCC-treatable disease or disorder may be a neoplastic disease. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

Also provided are kits for use in determining responsiveness to an antibody therapy in a patient which include an element for genotyping the sample to identify a FcγRIIA polymorphism; an element for genotyping the sample to identify a FcγRIIIA polymorphism; and a reference that correlates a genotype in the patient with one of more than three predicted therapeutic responses to the antibody therapy.

For example, the reference may correlate a genotype in the patient with one of nine predicted therapeutic responses to the antibody therapy.

In some embodiments, the FcγRIIA genotype is a H/H$^{131}$ genotype, wherein the FcγRIIIA genotype is a V/V$^{158}$ genotype, and wherein the reference indicates a high degree of responsiveness to the therapeutic antibody.

In other embodiments, the FcγRIIA genotype is a H/H$^{131}$ genotype, wherein the FcγRIIIA genotype is a V/F$^{158}$ or a F/F$^{158}$ genotype, and wherein the reference indicates an intermediate degree of responsiveness to the therapeutic antibody.

In some embodiments, the FcγRIIIA genotype is a V/V$^{158}$ genotype, wherein the FcγRIIA genotype is a H/R$^{131}$ or a R/R$^{131}$ genotype, and wherein the reference indicates an intermediate degree of responsiveness to the reference therapeutic antibody.

In other embodiments, the genotype is i) a V/F$^{158}$ genotype and a H/R$^{131}$ genotype; ii) a V/F$^{158}$ genotype and a R/R$^{131}$ genotype; iii) a F/F$^{158}$ genotype and a H/R$^{131}$ genotype; or iv) a F/F$^{158}$ genotype and a R/R$^{131}$, and wherein the reference indicates a low degree of responsiveness to the therapeutic antibody.

In some embodiments, the reference indicates choosing an variant antibody that exhibits enhanced binding to an FcγRIIA and/or an FcγRIIIA and/or that exhibits enhanced in vitro ADCC function.

In some embodiments, the therapeutic antibody is used for treating an ADCC-treatable disease or disorder. In some embodiments, the ADCC-treatable disease or disorder may be a neoplastic disease, an autoimmune disease, a microbial infection, or an allograft rejection. In some embodiments, the neoplastic disease is non-Hodgkin's lymphoma (NHL), e.g., follicular lymphoma.

Methods are provided for selecting a specific variant antibody therapy from a set of two or more variant antibody therapies for use in treatment of subjects having an ADCC-treatable disease by genotyping the subjects for an FcγRIIA polymorphism and a FcγRIIIA polymorphism, classifying the subjects into one of more than three categories of responsiveness based on their FcγRIIA polymorphism and their FcγRIIIA polymorphism, and selecting a specific variant antibody therapy for the subjects such that the degree of responsiveness to the antibody therapy in the subjects is improved from the degree of responsiveness obtained with another variant antibody.

In some embodiments, the subjects are classified into one of nine categories of responsiveness to the antibody therapy.

For example, the FcγRIIA polymorphism can be the H/R$^{131}$ polymorphism and the FcγRIIIA polymorphism can be the V/F$^{158}$ polymorphism.

In some embodiments, the presence of both a H/H$^{131}$ genotype and a V/V$^{158}$ genotype indicates a high degree of treatment response to the antibody therapy. In other embodiments, the identification of i) a H/H$^{131}$ genotype and ii) a V/F$^{158}$ or a F/F$^{158}$ genotype indicates an intermediate degree of treatment response to the antibody therapy. In other embodiments, the identification of i) a V/V$^{158}$ genotype and ii) a H/R$^{131}$ or a R/R$^{131}$ genotype indicates an intermediate degree of treatment response to the antibody therapy. In yet other embodiments, the identification of: i) a V/F$^{158}$ genotype and a H/R$^{131}$ genotype; ii) a 158 V/F genotype and a R/R$^{131}$ genotype; iii) a F/F$^{158}$ genotype and a H/R$^{131}$ genotype; or iv) a F/F$^{158}$ genotype and a R/R$^{131}$ genotype indicates a low degree of treatment response to the antibody therapy.

In some embodiments, the ADCC-treatable disease or disorder may be a neoplastic disease, an autoimmune disease, a microbial infection, or an allograft rejection. In some embodiments, the ADCC-treatable disease or disorder may be a neoplastic disease. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

For example, the monoclonal antibody may include one or more amino acid substitutions compared to Rituximab, wherein the one or more amino acid substitutions provide for enhanced binding and/or in vitro ADCC function to at least one of an FcγRIIA comprising H/R$^{131}$ or R/R$^{131}$ alleles, and an FcγRIIIA comprising V/F$^{158}$ or F/F$^{158}$ alleles.

Methods are also provided for treating an ADCC-treatable disease or disorder in a subject by genotyping the subject for an FcγRIIA polymorphism and an FcγRIIIA polymorphism, classifying the subject into one of more than three categories of therapeutic responsiveness to an antibody therapy based on the FcγRIIA polymorphism and the FcγRIIIA polymorphism, selecting an antibody with a preferred degree of therapeutic responsiveness from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function, and administering a therapeutically effective amount of the antibody to the subject, wherein, the antibody treats the ADCC-treatable disease or disorder in the subject.

In some embodiments, the subject is classified into one of nine categories of therapeutic responsiveness.

For example, the FcγRIIA polymorphism may be the H/R$^{131}$ polymorphism, and the FcγRIIIA polymorphism may be the V/F$^{158}$ polymorphism.

In some embodiments, the genotyping identifies a H/H$^{131}$ genotype and a V/V$^{158}$ genotype, and the antibody is selected for binding to at least one of an FcγRIIA comprising H/H$^{131}$ allele and an FcγRIIIA comprising V/V$^{158}$ allele.

In some embodiments, the genotyping identifies a H/H$^{131}$ genotype and a V/F$^{158}$ genotype, and the variant antibody is selected for enhanced binding and/or in vitro ADCC function to at least one of an FcγRIIA comprising H/H$^{131}$ allele and an FcγRIIIA comprising V/F$^{158}$ allele.

In some embodiments, the genotyping identifies a H/H$^{131}$ genotype and a F/F$^{158}$ genotype, and the variant antibody is selected for enhanced binding and/or in vitro ADCC function to at least one of an FcγRIIA comprising H/H$^{131}$ allele and an FcγRIIIA comprising F/F$^{158}$ allele.

In some embodiments, the genotyping identifies a V/V$^{158}$ genotype and a H/R$^{131}$ genotype, and the variant antibody is selected for enhanced binding and/or in vitro ADCC function to at least one of an FcγRIIA comprising H/R$^{131}$ allele and an FcγRIIIA comprising V/V$^{158}$ allele.

In some embodiments, the genotyping identifies a V/V$^{158}$ genotype and a R/R$^{131}$ genotype, and the variant antibody is selected for enhanced binding and/or in vitro ADCC function to at least one of an FcγRIIA comprising R/R$^{131}$ allele and an FcγRIIIA comprising V/V$^{158}$ allele.

In other embodiments, the genotyping identifies a V/F$^{158}$ genotype and a H/R$^{131}$ genotype, and the variant antibody is selected for enhanced binding and/or in vitro ADCC function to at least one of an FcγRIIA comprising H/R$^{131}$ allele and an FcγRIIIA comprising V/F$^{158}$ allele.

In other embodiments, the genotyping identifies a V/F$^{158}$ genotype and a R/R$^{131}$ genotype, and the variant antibody is selected for enhanced binding and/or in vitro ADCC function to at least one of an FcγRIIA comprising R/R$^{131}$ allele and an FcγRIIIA comprising V/F$^{158}$ allele.

In some embodiments, the genotyping identifies a F/F$^{158}$ genotype and a H/R$^{131}$ genotype, and the variant antibody is selected for enhanced binding and/or in vitro ADCC function to at least one of an FcγRIIA comprising H/R$^{131}$ allele and an FcγRIIIA comprising F/F$^{158}$ allele.

In other embodiments, the genotyping identifies a F/F$^{158}$ genotype and a R/R$^{131}$ genotype, and the variant antibody is selected for enhanced binding and/or in vitro ADCC function to at least one of an FcγRIIA comprising R/R$^{131}$ and an FcγRIIIA comprising F/F$^{158}$ allele.

In some embodiments, the ADCC-treatable disease or disorder may be a neoplastic disease, an autoimmune disease, a microbial infection, or an allograft rejection. In some embodiments, the ADCC-treatable disease or disorder may be a neoplastic disease. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

In another embodiment, the monoclonal antibody includes one or more amino acid substitutions compared to Rituximab, wherein the one or more amino acid substitutions provide for enhanced binding and/or in vitro ADCC function to at least one of an FcγRIIA comprising H/R$^{131}$ or R/R$^{131}$ alleles, and an FcγRIIIA comprising V/F$^{158}$ or F/F$^{158}$ alleles.

Methods are provided for making a set of related antibodies capable of modulating the responsiveness of a subject having an ADCC-treatable disease or disorder to an antibody therapy for the disease or disorder by modifying the amino acid sequence of at least one amino acid residue in a parent antibody, such that the modified parent antibody exhibits enhanced binding affinity to at least one Fc receptor encoded by an Fc receptor gene of a first genotype, compared to the Fc binding affinity of the parent antibody, to generate a first variant antibody; and modifying at least one amino acid residue in a parent antibody, such that the modified parent antibody exhibits enhanced binding affinity to at least one Fc receptor encoded by an Fc receptor gene of a second genotype, compared to the Fc binding affinity of the parent antibody, to generate a second variant antibody, wherein the first and second variant antibodies have the same antigen specificity and are capable of modulating the responsiveness of a subject having an ADCC-treatable disease or disorder to an antibody therapy for the disease or disorder.

For example, the first and the second variant antibodies may include one or more amino acid residue modifications in one or more locations of a lower hinge region, a CH2 domain, and/or a CH3 domain.

In some embodiments, the parent antibody may be a therapeutic antibody used in therapy of an ADCC-treatable disease or disorder.

In some embodiments, the ADCC-treatable disease or disorder may be a neoplastic disease, an autoimmune disease, a viral infection, a parasitic infection, or an allograft rejection. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

In other embodiments, the parent antibody is modified in its Fc domain. In another embodiment, the parent antibody is modified in its CDR.

Methods are provided for generating a set of variant antibodies capable of modulating the responsiveness of a subject having an ADCC-treatable disease or disorder to an antibody therapy for the disease or disorder by amplifying a nucleic acid comprising a nucleotide sequence encoding a region of an antibody, wherein the amplifying is carried out with a set of primers that encode all nineteen amino acid variants at a single residue of the region, to generate a set of variant nucleic acids encoding nineteen amino acid substitution variants at the single residue of the region, transcribing and translating each of the variant nucleic acids in vitro, to generate a set of variants, and/or selecting from the set an variant having altered FcR binding activity compared to a reference region, generating a set of selected variants, wherein the first and second variant antibodies have the same antigen specificity and are capable of modulating the responsiveness of a subject having an ADCC-treatable disease or disorder to an antibody therapy for the disease or disorder. In some embodiments, the method includes determining in vitro ADCC activity of the selected variant.

In some embodiments, the methods include, repeating step amplifying a nucleic acid comprising a nucleotide sequence encoding a region of an antibody, wherein the amplifying is carried out with a set of primers that encode all nineteen amino acid variants at a single residue of the region at a second residue of the region, generating a second set of variants and generating a second set of selected variants.

In some embodiments, the transcribing and translating are carried out using a prokaryotic expression system. For example, the region-encoding nucleotide sequence may be under the transcriptional control of a phage promoter.

In some embodiments, FcR binding activity is assessed using an enzyme-linked immunosorbent assay.

In some embodiments, the parent antibody is modified in its Fc domain. In other embodiments, the parent antibody is modified in its CDR.

Methods are also provided for modulating the responsiveness of a subject having an ADCC-treatable disease or disorder to an antibody therapy for the disease or disorder by genotyping the subject for an FcγRIIA polymorphism and an FcγRIIIA polymorphism, classifying the subject into one of more than three categories of therapeutic responsiveness to an antibody therapy based on the FcγRIIA polymorphism and the FcγRIIIA polymorphism, selecting an antibody from a set of related antibodies, wherein members of the set of related antibodies have the same antigen binding specificity, and wherein the members of the set of related antibodies differ in binding affinity to an FcγRIIA and/or an FcγRIIIA and/or differ in in vitro ADCC function, and administering a therapeutically effective amount of the antibody to the subject, wherein the antibody modulates the responsiveness of the subject having an ADCC-treatable disease or disorder to an antibody therapy for the disease or disorder.

For example, the subject may be classified into one of nine categories of therapeutic responsiveness.

In some embodiments, the antibody increases responsiveness to the antibody therapy. In other embodiments, the antibody decreases responsiveness to the antibody therapy.

For example, the FcγRIIA polymorphism may be the $H/R^{131}$ polymorphism, and the FcγRIIIA polymorphism may be the $V/F^{158}$ polymorphism.

In some embodiments, the genotyping identifies a $H/H^{131}$ genotype and a $V/V^{158}$ genotype, and the antibody is selected for enhanced binding to at least one of an FcγRIIA comprising an $H/H^{131}$ allele and an FcγRIIIA comprising an $V/V^{158}$ allele.

In other embodiments the genotyping identifies a $H/H^{131}$ genotype and a $V/F^{158}$ genotype, and the variant antibody is selected for enhanced binding and/or in vitro ADCC function to at least one of an FcγRIIA comprising $H/H^{131}$ allele and an FcγRIIIA comprising an $V/F^{158}$ allele.

In some embodiments, the genotyping identifies a $H/H^{131}$ genotype and a $F/F^{158}$ genotype, and the variant antibody is selected for enhanced binding and/or in vitro ADCC function to at least one of an FcγRIIA comprising $H/H^{131}$ allele and an FcγRIIIA comprising an $F/F^{158}$ allele.

In some embodiments, the genotyping identifies a $V/V^{158}$ genotype and a $H/R^{131}$ genotype, and the variant antibody is selected for enhanced binding and/or in vitro ADCC function to at least one of an FcγRIIA comprising $H/R^{131}$ allele and an FcγRIIIA comprising an $V/V^{158}$ allele.

In some embodiments, the genotyping identifies a $V/V^{158}$ genotype and a $R/R^{131}$ genotype, and the variant antibody is selected for enhanced binding and/or in vitro ADCC function to at least one of an FcγRIIA comprising $R/R^{131}$ allele and an FcγRIIIA comprising an $V/V^{158}$ allele.

In some embodiments, the genotyping identifies a $V/F^{158}$ genotype and a $H/R^{131}$ genotype, and the variant antibody is selected for enhanced binding and/or in vitro ADCC function to at least one of an FcγRIIA comprising $H/R^{131}$ allele and an FcγRIIIA comprising an $V/F^{158}$ allele.

In some embodiments, the genotyping identifies a $V/F^{158}$ genotype and a $R/R^{131}$ genotype, and the variant antibody is selected for enhanced binding and/or in vitro ADCC function to at least one of an FcγRIIA comprising $R/R^{131}$ allele and an FcγRIIIA comprising an $V/F^{158}$ allele.

In some embodiments, the genotyping identifies a $F/F^{158}$ genotype and a $H/R^{131}$ genotype, and the variant antibody is selected for enhanced binding and/or in vitro ADCC function to at least one of an FcγRIIA comprising $H/R^{131}$ allele and an FcγRIIIA comprising an $F/F^{158}$ allele.

In some embodiments, the genotyping identifies or a $F/F^{158}$ genotype and a $R/R^{131}$ genotype, and the variant antibody is selected for enhanced binding and/or in vitro ADCC function to at least one of an FcγRIIA comprising $R/R^{131}$ and an FcγRIIIA comprising an $F/F^{158}$ allele.

In some embodiments, the ADCC-treatable disease or disorder may be a neoplastic disease, an autoimmune disease, a microbial infection, or an allograft rejection. In some embodiments, the neoplastic disease may be non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

For example, the related antibodies may include one or more amino acid substitutions compared to Rituximab, wherein the one or more amino acid substitutions provide for enhanced binding and/or in vitro ADCC function to at least one of an FcγRIIA comprising $H/R^{131}$ or $R/R^{131}$ alleles, and an FcγRIIIA comprising $V/F^{158}$ or $F/F^{158}$ alleles.

In some embodiments, the genotyping identifies a $H/H^{131}$ genotype and a $V/V^{158}$ genotype, and the antibody is selected for decreased binding to at least one of an FcγRIIA comprising $H/H^{131}$ allele and an FcγRIIIA comprising an $V/V^{158}$ allele.

In other embodiments, the genotyping identifies a $H/H^{131}$ genotype and a $V/F^{158}$ genotype, and the variant antibody is selected for decreased binding and/or in vitro ADCC function to at least one of an FcγRIIA comprising $H/H^{131}$ allele and an FcγRIIIA comprising an $V/F^{158}$ allele.

In some embodiments, the genotyping identifies a $H/H^{131}$ genotype and a $F/F^{158}$ genotype, and the variant antibody is selected for decreased binding and/or in vitro ADCC function to at least one of an FcγRIIA comprising $H/H^{131}$ allele and an FcγRIIIA comprising an $F/F^{158}$ allele.

In some embodiments, the genotyping identifies a $V/V^{158}$ genotype and a $H/R^{131}$ genotype, and the variant antibody is selected for decreased binding and/or in vitro ADCC function to at least one of an FcγRIIA comprising $H/R^{131}$ allele and an FcγRIIIA comprising an $V/V^{158}$ allele.

In some embodiments, the genotyping identifies a $V/V^{158}$ genotype and a $R/R^{131}$ genotype, and the variant antibody is selected for decreased binding and/or in vitro ADCC function to at least one of an FcγRIIA comprising $R/R^{131}$ allele and an FcγRIIIA comprising an $V/V^{158}$ allele.

In some embodiments, the genotyping identifies a $V/F^{158}$ genotype and a $H/R^{131}$ genotype, and the variant antibody is selected for decreased binding and/or in vitro ADCC function to at least one of an FcγRIIA comprising $H/R^{131}$ allele and an FcγRIIIA comprising an $V/F^{158}$ allele.

In other embodiments, the genotyping identifies a $V/F^{158}$ genotype and a $R/R^{131}$ genotype, and the variant antibody is selected for decreased binding and/or in vitro ADCC function to at least one of an FcγRIIA comprising $R/R^{131}$ allele and an FcγRIIIA comprising an $V/F^{158}$ allele.

In some embodiments, the genotyping identifies a $F/F^{158}$ genotype and a $H/R^{131}$ genotype, and the variant antibody is selected for decreased binding and/or in vitro ADCC function to at least one of an FcγRIIA comprising $H/R^{131}$ allele and an FcγRIIIA comprising an $F/F^{158}$ allele.

In some embodiments, the genotyping identifies a $F/F^{158}$ genotype and a $R/R^{131}$ genotype, and the variant antibody is selected for decreased binding and/or in vitro ADCC function to at least one of an FcγRIIA comprising $R/R^{131}$ and an FcγRIIIA comprising an $F/F^{158}$ allele.

In some embodiments, the ADCC-treatable disease or disorder may be a neoplastic disease, an autoimmune disease, a microbial infection, or an allograft rejection. In some embodiments, the neoplastic disease is non-Hodgkin's lymphoma (NHL), e.g., follicular lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

In some embodiments, the related antibodies include one or more amino acid substitutions compared to Rituximab, wherein the one or more amino acid substitutions provide for decreased binding and/or in vitro ADCC function to at least one of an FcγRIIA comprising $H/R^{131}$ or $R/R^{131}$ alleles, and an FcγRIIIA comprising $V/F^{158}$ or $F/F^{158}$ alleles.

Methods are provided for enhancing antibody dependent cell mediated cytotoxicity (ADCC) activity of an antibody for use in treatment of a subject having an ADCC-treatable disease by genotyping the subject for an FcγRIIA polymorphism and a FcγRIIIA polymorphism, selecting an Fc nucleotide sequence for the antibody that has optimal ADCC for the FcγRIIA polymorphism and FcγRIIIA polymorphism, and modifying the antibody to include the optimal Fc sequence for the subject's genotype, wherein the ADCC activity of the antibody is enhanced by using the optimal Fc.

For example, the FcγRIIA polymorphism may be the $H/R^{131}$ polymorphism, and the FcγRIIIA polymorphism may be the $V/F^{158}$ polymorphism.

In some embodiments, the patient may have a hyperproliferative disorder. In other embodiments, the hyperproliferative disorder may be cancer, e.g., non-Hodgkin's lymphoma.

In some embodiments, the antibody is a therapeutic antibody, e.g., RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab) or ZEVALIN® (ibritumomab tiuxetan).

The genotypes determined by any of the above-disclosed methods may include (i.) an FcγRIIIA $V/V^{158}$ genotype, an FcγRIIIA $V/F^{158}$ or an FcγRIIIA $F/F^{158}$ genotype; or (an FcγRIIA $H/H^{131}$ genotype, an FcγRIIA $H/R^{131}$ genotype or an FcγRIIA $R/R^{131}$ genotype, or (iii.) a FcγRIIIA $V/V^{158}$, FcγRIIA $H/H^{131}$ genotype, a FcγRIIIA $V/F^{158}$, FcγRIIA $H/H^{131}$ genotype, a FcγRIIIA $F/F^{158}$, FcγRIIA $H/H^{131}$ genotype, a FcγRIIIA $V/V^{158}$, FcγRIIA $H/R^{131}$ genotype, a FcγRIIIA $V/F^{158}$, FcγRIIA $H/R^{131}$ genotype, a FcγRIIIA $F/F^{158}$, FcγRIIA $H/R^{131}$ genotype, a FcγRIIIA $V/V^{158}$, FcγRIIA $R/R^{131}$ genotype, a FcγRIIIA $V/F^{158}$, FcγRIIA $R/R^{131}$ genotype or a FcγRIIIA $F/F^{158}$, FcγRIIA $R/R^{131}$ genotype.

It is to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As summarized above, the subject disclosure is directed to methods of determining whether a subject suffering from a neoplastic condition is responsive to a particular therapy, such as antibody therapy, as well as reagents and kits thereof (and devices) for use in practicing the subject methods. In further

Methods of Determining Whether a Subject Suffering from a Neoplastic Condition is Responsive to a Particular Therapy Methods are provided for determining whether a patient or subject suffering from a neoplastic disease, i.e., hyperproliferative disorder, is responsive to a particular therapy, such as antibody therapy. Hyperproliferative disorders, or malignancies, are conditions in which there is unregulated cell growth. The methods of the present disclosure are directed at hyperproliferative disorders and particularly whether such a disorder will or will not be responsive to a particular antineoplastic therapy, e.g., antibody therapy. The disorder may be characterized by the presence or absence of solid tumors.

In certain embodiments, the subject methods are directed to determining whether a B-cell hyperproliferative disorder, e.g., NHL, is responsive to therapeutic antibody therapy. B-cell hyperproliferative disorders are those disorders that derive from cells in the B cell lineage, typically including hematopoietic progenitor cells expressing B lineage markers, pro-B cells, pre-B cells, B-cells and memory B cells; and that express markers typically found on such B lineage cells.

Of particular interest are non-Hodgkin's lymphomas (NHLs), which are a heterogeneous group of lymphoproliferative malignancies with different patterns of behavior and responses to treatment. Like Hodgkin's disease, NHL usually originates in lymphoid tissues and can spread to other organs, however, NHL is much less predictable than Hodgkin's disease regarding their responses to therapy and has a far greater predilection to disseminate to extranodal sites. The NHLs can be divided into 2 prognostic groups: the indolent lymphomas and the aggressive lymphomas. Indolent NHL types have a relatively good prognosis, with median survival as long as 10 years, but they usually are not curable in advanced clinical stages. The aggressive type of NHL has a shorter natural history. A number of these patients can be cured with intensive combination chemotherapy regimens, but there is a significant number of relapses, particularly in the first 2 years after therapy.

Among the NHL are a variety of B-cell neoplasms, including precursor B-lymphoblastic leukemia/lymphoma; peripheral B-cell neoplasms, e.g. B-cell chronic lymphocytic leukemia; prolymphocytic leukemia; small lymphocytic lymphoma; mantle cell lymphoma; follicle center cell lymphoma; marginal zone B-cell lymphoma; splenic marginal zone lymphoma; hairy cell leukemia; diffuse large B-cell lymphoma; T-cell rich B-cell lymphoma, Burkitt's lymphoma; high-grade B-cell lymphoma, (Burkitt-like); etc.

Follicular lymphoma comprises 70% of the indolent lymphomas reported in American and European clinical trials. Most patients with follicular lymphoma are over age 50 and present with widespread disease at diagnosis. Nodal involvement is most common, often accompanied by splenic and bone marrow disease. The vast majority of patients are diagnosed with advanced stage follicular lymphoma and are not cured with current therapeutic options, and the rate of relapse is fairly consistent over time, even in patients who have achieved complete responses to treatment. Subtypes include follicular small cleaved cell (grade 1) and follicular mixed small cleaved and large cell (grade 2). Another subtype of interest is follicular large cell (grade 3 or FLC) lymphoma which can be divided into grades 3a and 3b.

Marginal zone lymphomas were previously included among the diffuse small lymphocytic lymphomas. When marginal zone lymphomas involve the nodes, they are called monocytoid B-cell lymphomas, and when they involve extranodal sites (gastrointestinal tract, thyroid, lung, breast, skin), they are called mucosa-associated lymphatic tissue (MALT) lymphomas. Many patients have a history of autoimmune disease, such as Hashimoto's thyroiditis or Sjogren's syndrome, or of *Helicobacter gastritis*. Most patients present with stage I or II extranodal disease, which is most often in the stomach. When disseminated to lymph nodes, bone marrow, or blood, this entity behaves like other low-grade lymphomas. Large B-cell lymphomas of MALT sites are classified and treated as diffuse large cell lymphomas.

Splenic marginal zone lymphoma is an indolent lymphoma that is marked by massive splenomegaly and peripheral blood and bone marrow involvement, usually without adenopathy. This type of lymphoma is otherwise known as splenic lymphoma with villous lymphocytes, an uncommon variant of B-cell chronic lymphocytic leukemia. Management of this entity usually starts with splenectomy which is different than other low-grade lymphomas. If/when the disease progresses after splenectomy, it tends to be managed like other low grade lymphomas.

Among the aggressive forms of NHL is diffuse large B-cell lymphoma, which is the most common of the non-Hodgkin's lymphomas, comprising 30% of newly-diagnosed cases. Most patients present with rapidly enlarging masses, often with symptoms both locally and systemically. Relapses after treatment are not uncommon, depending on the presence of various risk factors. Lymphomatoid granulomatosis is an EBV positive large B-cell lymphoma with a predominant T-cell background. The histology shows association with angioinvasion and vasculitis, usually manifesting as pulmonary lesions or paranasal sinus involvement. Patients are managed like others with diffuse large cell lymphoma.

Primary mediastinal B-cell lymphoma is a subset of diffuse large cell lymphoma characterized by significant fibrosis on histology. Patients are usually female and young. Patients present with a locally invasive anterior mediastinal mass which may cause respiratory symptoms or superior vena cava syndrome. Therapy and prognosis are the same as for other comparably-staged patients with diffuse large cell lymphoma, except for advanced-stage patients with a pleural effusion, who have an extremely poor prognosis (progression-free survival is less than 20%) whether the effusion is cytologically positive or negative.

Mantle cell lymphoma is found in lymph nodes, the spleen, bone marrow, blood, and sometimes the gastrointestinal system (lymphomatous polyposis). Mantle cell lymphoma is characterized by CD5-positive mantle zone B cells, a translocation of chromosomes 11 and 14, and an overexpression of the cyclin D1 protein. The median survival is significantly shorter (3-5 years) than that of other lymphomas, and this histology is now considered to be an aggressive lymphoma. A diffuse pattern and the blastoid variant have an even more aggressive course with shorter survival, while the mantle zone type may have a more indolent course. Refractoriness to chemotherapy is a usual feature.

Lymphoblastic lymphoma is a very aggressive form of NHL. It often occurs in young patients, but not exclusively. It is commonly associated with large mediastinal masses and has a high predilection for disseminating to bone marrow and the central nervous system (CNS). Treatment is usually patterned after that for acute lymphoblastic leukemia (ALL). Since these forms of NHL tend to progress so quickly, combination chemotherapy is instituted rapidly once the diagnosis has been confirmed. Careful review of the pathologic specimens, bone marrow aspirate and biopsy specimen, cerebrospinal fluid cytology, and lymphocyte marker constitute the most important aspects of the pretreatment staging work-up.

Burkitt's lymphoma/diffuse small noncleaved cell lymphoma typically involves younger patients and represents the most common type of pediatric non-Hodgkin's lymphoma. These aggressive extranodal B-cell lymphomas are characterized by translocation and deregulation of the c-myc gene on chromosome 8. A subgroup of patients with dual translocation of c-myc and bcl-2 appear to have an extremely poor outcome despite aggressive therapy. Treatment of Burkitt's lymphoma/diffuse small noncleaved cell lymphoma involves aggressive multidrug regimens similar to those used for the advanced-stage aggressive lymphomas.

Patients who undergo transplantation of the heart, lung, liver, kidney, or pancreas usually require life-long immunosuppression. Life-long immunosuppression may result in post-transplantation lymphoproliferative disorder (PTLD), which appears as an aggressive lymphoma. Pathologists can distinguish a polyclonal B-cell hyperplasia from a monoclonal B-cell lymphoma; both are almost always associated with EBV. In some cases, usually for the polyclonal forms of the disease, withdrawal of immunosuppression results in eradication of the lymphoma. When this is unsuccessful or not feasible, a combination chemotherapy is usually used. EBV-negative post-transplantation lymphoproliferative disorders occur late and have a particularly poor prognosis. Chronic lymphocytic leukemia (CLL) is a disorder of morphologically mature but immunologically less mature lymphocytes and is manifested by progressive accumulation of these cells in the blood, bone marrow, and lymphatic tissues. Lymphocyte counts in the blood are usually equal to or higher than 10,000 per cubic millimeter. At present there is no curative therapy. CLL occurs primarily in middle-aged and elderly individuals, with increasing frequency in successive decades of life. The clinical course of this disease progresses from an indolent lymphocytosis without other evident disease to one of generalized lymphatic enlargement with concomitant pancytopenia. Complications of pancytopenia, including hemorrhage and infection, represent a major cause of death in these patients. Immunological aberrations, including Coombs-positive hemolytic anemia, immune thrombocytopenia, and depressed immunoglobulin levels may all complicate the management of CLL. CLL lymphocytes coexpress the B-cell antigens CD19 and CD20 along with the T-cell antigen CD5. CLL B cells express relatively low levels of surface-membrane immunoglobulin (compared with normal peripheral blood B cells). CLL is diagnosed by an absolute increase in lymphocytosis and/or bone marrow infiltration coupled with the characteristic features of morphology and immunophenotype.

AIDS-related lymphomas are comprised of a narrow spectrum of histologic types consisting almost exclusively of B-cell tumors of aggressive type. These include diffuse large cell lymphoma; B-immunoblastic; and small non-cleaved, either Burkitt's or Burkitt's like. The HIV-associated lymphomas can be categorized into: primary central nervous system lymphoma (PCNSL); systemic lymphoma; and primary effusion lymphoma. All of these lymphomas differ from non-HIV-related lymphomas in their molecular characteristics, presumed mechanism of pathogenesis, treatment, and clinical outcome. All three pathologic types are equally distributed and represent aggressive disease. In general, the clinical setting and response to treatment of patients with AIDS-related lymphoma is very different from the non-HIV patients with lymphoma. The HIV-infected individual with aggressive lymphoma usually presents with advanced-stage disease that is frequently extranodal. The clinical course is more aggressive, and the disease is both more extensive and less responsive to chemotherapy. Immunodeficiency and cytopenias, common in these patients at the time of initial presentation, are exacerbated by the administration of chemotherapy. Therefore, treatment of the malignancy increases the risk of opportunistic infections that, in turn, further compromise the delivery of adequate treatment.

Acute lymphocytic leukemia (ALL) generally has an aggressive course, depending in part on the presence of the Philadelphia (Ph) chromosome. Patients with Ph chromosome-positive ALL are rarely cured with chemotherapy. Many patients who have molecular evidence of the bcr-abl fusion gene, which characterizes the Ph chromosome, have no evidence of the abnormal chromosome by cytogenetics.

Although the methods of the disclosure are primarily applied to NHL, in some cases treatment may be used in cases of Hodgkin's lymphoma, which is a lymphoma characterized by a pleomorphic lymphocytic infiltrate with malignant multinucleated giant cells. Most cases of Hodgkin's disease probably arise from germinal center B cells that are unable to synthesize immunoglobulin. The majority of cases in developing countries and about one third of those in the United States are associated with the presence of Epstein-Barr virus in the Reed-Sternberg cells. Treatment strategies depend on a number of factors including the presence of B symptoms, the histologic subtype, gender, and sexual maturity. To date there are several published studies demonstrating the effectiveness of Rituxan for CD20-positive Hodgkin's disease, particularly the lymphocyte predominant variant.

Other neoplastic disease conditions whose responsiveness to antibody therapy can be evaluated according to the subject methods include, but are not limited to: colorectal cancer, non-small cell lung cancer, small cell lung cancer, ovarian cancer, breast cancer, head and neck cancer, renal cell carcinoma, and the like.

As summarized above, the subject methods may be used to evaluate the responsiveness of a subject to a given antineoplastic therapy. Antineoplastic therapies of interest include, but are not limited to: chemotherapy, radiation therapy, antibody therapy, etc.

By therapeutic antibody therapy is meant a treatment protocol or regimen that includes administration of a therapeutic antibody agent. Representative therapeutic antibody agents specifically bind to antigens present on B cells, particularly hyperproliferative B cells, e.g. B lineage lymphomas and leukemias, and the like. The term "antibody" is used in the broadest sense and specifically covers monoclonal antibodies (including full length monoclonal antibodies), polyclonal antibodies, multispecific antibodies (e.g., bispecific antibodies), antibody fragments, and Fc:fusion proteins so long as they exhibit the desired biological activity. Fragments comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. In some aspects of the disclosure, a combination of one or more antibodies with different specificities, either for epitopes of a single antigen, or for multiple antigens, may be used.

Markers that are specifically found on B-cells include CD45R, which is an exon specific epitope found on essentially all B-cells, and is maintained throughout B cell development (Coffman et al. (1982) *Immunol. Rev.* 69:5-23). The B-cell markers CD19, CD20; CD22; CD23 are selectively expressed on B-cells and have been associated with B-cell malignancies (Kalil and Cheson (2000) *Drugs Aging* 16(1): 9-27; U.S. Pat. No. 6,183,744, herein incorporated by reference). Surface immunoglobulin, including epitopes present on the constant regions or idiotypic determinants, is a specific marker for B-cells and has been utilized in immunotherapy (Caspar et al., (1997) *Blood* 90(9):3699-706). The MB-1 antigen is found on all normal immunoglobulin (Ig)-expressing cells, but not on T-cells, thymocytes, granulocytes, or platelets, and expressed by virtually all Ig-expressing B-cell tumors (Link et al. (1986) *J. Immunol.* 137(9):3013-8). Other B cell antigens of interest known to be expressed, for example, on non-Hodgkin's lymphomas, are Muc-1; B5; BB1; and T9 (Freedman et al., (1987) *Leukemia* 1(1):9-15).

Of particular interest is the CD20 antigen, also known as "Bp35". (Note that CD20 was called B1 early in the course of research on B-cell markers). CD20 is a human B cell marker that is expressed during early pre-B cell development and remains until plasma cell differentiation. The CD20 molecule may regulate a step in the activation process that is required for cell cycle initiation and differentiation, and is usually expressed at very high levels on neoplastic B cells. Thus, the CD20 surface antigen can be targeted for treating B cell lymphomas. U.S. Pat. No. 5,736,137, herein incorporated by reference, describes the chimeric antibody "C2B8" that binds the CD20 antigen and its use to treat B-cell lymphoma (antibody is also known as Rituxan®, rituximab, Mabthera (this is a trademark in Europe)).

In an embodiment, the antibody is a monoclonal antibody. Monoclonal antibodies are highly specific, being directed against a single antigenic site, and each monoclonal antibody is directed against a single determinant on the antigen. For example, the monoclonal antibodies to be used in accordance with the present disclosure may be made by the hybridoma method first described by Kohler et al. (1975) *Nature* 256: 495, or may be made by recombinant DNA methods (see, e.g., U.S. Pat. No. 4,816,567). The monoclonal antibodies may also be isolated from phage antibody libraries using the techniques described in Clackson et al., (1991) *Nature* 352:624-628 (1991) and Marks et al., (1991) *J. Mol. Biol.* 222:581-597 (1991), for example. For clinical use, the monoclonal antibodies may be humanized forms of non-human antibodies. These are chimeric antibodies that contain sequences derived from both human and non-human immunoglobulin. For the most part, humanized antibodies are human immunoglobulins in which residues from a hypervariable region of the recipient are replaced by residues from a hypervariable region of a non-human species having the desired specificity, affinity, and capacity.

Specificity, as used herein, refers to the affinity of the antibody, and to the cross-reactivity with other antigens. In order to consider an antibody interaction to be "specific", the affinity will be at least about $10^{-7}$ M, usually about $10^{-8 \text{ to } -9}$ M, and may be up to $10^{-11}$ M or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g., to a relatedness of antigen sequence or structure, or to the structure of the antibody binding pocket itself. Antibodies demonstrating such cross-reactivity are still considered specific for the purposes of the present disclosure.

In practicing the subject methods, a subject or patient sample, e.g., cells or collections thereof, e.g., tissues, is assayed to determine whether the host or subject from which the assayed sample was obtained is responsive to a given therapy, e.g., therapeutic antibody therapy. The sample obtained from the host is assayed to determine the genotype of the host or subject from which the sample was obtained with respect to at least two or more, polymorphisms, where polymorphisms of interest are referred to herein as target polymorphisms.

In certain embodiments, the target polymorphisms are FcγR polymorphisms. An FcγR polymorphism is a polymorphism present in an FcγR (Fc receptor) protein. FcγR proteins of interest include, but are not limited to, FcγRII proteins (e.g., FcγRIIA, also known as CD32 (whose amino acid and nucleotide sequence is present at Genbank accession NOs. NM_021642 or M28697)); FcγRIII proteins (e.g., FcγRIIIA, also known as CD16 (whose amino acid and nucleotide sequence is present at Genbank accession NOs. BC036723; BC033678; BC017865 and NM_000569)).

In certain embodiments, the sample is assayed to determine the genotype of a subject with respect to two or more different target polymorphisms, where the two or more different target polymorphisms include at least one FcγR polymorphism. In certain of these embodiments, at least two of the target polymorphisms are different FcγR polymorphisms, such as an FcγRII and an FcγRIII polymorphism.

In some embodiments, the sample is assayed to determine the genotype of the subject with respect to at least two or more target polymorphisms, where, the target polymorphisms are an FcγRII polymorphism and a FcγRIII polymorphism. In certain embodiments, the FcγRIIA polymorphism is the FcγRIIA H/R$^{131}$ polymorphism (where the nucleotide codons encoding the H and R residues of the polymorphism are CAT and CGT, respectively). In certain embodiments, the FcγRIIIA polymorphism is the FcγRIIIA V/F$^{158}$ polymorphism (where the nucleotide codons encoding the V and F residues of the polymorphism are GTT and TTT, respectively).

In practicing the subject methods, a subject or patient sample, e.g., cells or collections thereof, e.g., tissues, is assayed to determine whether the host or subject from which the assayed sample was obtained is responsive to a given therapy, e.g., therapeutic antibody therapy. In practicing the subject diagnostic methods, the sample obtained from the host is assayed to determine the genotype of the host or subject from which the sample was obtained with respect to at least one, i.e., one or more, polymorphisms, where polymorphisms of interest are referred to herein as target polymorphisms. In certain embodiments, the at least one target polymorphism is an FcγR polymorphism. An FcγR polymorphism is a polymorphism present in an FcγR (Fc receptor) protein. FcγR proteins of interest include, but are not limited to, FcγRII proteins (e.g., FcγRIIA, also known as CD32 (whose amino acid and nucleotide sequence is present at Genbank accession nos. NM_021642 or M28697)); FcγRIII proteins (e.g., FcγRIIIA, also known as CD16 (whose amino acid and nucleotide sequence is present at Genbank accession nos. BC036723; BC033678; BC017865 and NM_000569)), and the like. In certain embodiments, the sample is assayed to determine the genotype of the host with respect to a single target polymorphism, where in these embodiments, the single target polymorphism is an FcγRII polymorphism, such as an FcγRIIA polymorphism, where a specific representative FcγRIIA polymorphism of interest is the FcγRIIa H/R$^{131}$ polymorphism (where the nucleotide codons encoding the H and R residues of the polymorphism are CAT and CGT, respectively). In certain embodiments, the sample is assayed to determine the genotype of the host with respect to two or more different target polymorphisms, where in these embodiments, the two or more different target polymorphisms include at least one FcγR polymorphism. In certain of these embodiments, at least two of the target polymorphisms are different FcγR polymorphisms, such as an FcγRII and an FcγRIII polymorphism. In certain embodiments, the sample is assayed for both an FcγRII polymorphism, such as the specific FcγRIIa polymorphisms described above, and an FcγRIII polymorphism, such as an FcγRIIIA polymorphism, including the FcγRIIIA V/F$^{158}$ polymorphism (where the nucleotide codons encoding the V and F residues of the polymorphism are GTT and TTT, respectively).

Any convenient protocol for assaying a sample for the above one or more target polymorphisms may be employed in the subject methods. In certain embodiments, the target polymorphism will be detected at the protein level, e.g., by assaying for a polymorphic protein. In yet other embodiments, the target polymorphism will be detected at the nucleic acid level, e.g., by assaying for the presence of nucleic acid polymorphism, e.g., a single nucleotide polymorphism (SNP) that cause expression of the polymorphic protein.

For example, polynucleotide samples derived from (e.g., obtained from) an individual may be employed. Any biological sample that comprises a polynucleotide from the individual is suitable for use in the methods of the disclosure. The biological sample may be processed so as to isolate the polynucleotide. Alternatively, whole cells or other biological samples may be used without isolation of the polynucleotides contained therein. Detection of a target polymorphism in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; and the like. Detection of a target polymorphism can also be accomplished by detecting an alteration in the level of a mRNA transcript of the gene; aberrant modification of the corresponding gene, e.g., an aberrant methylation pattern; the presence of a non-wild-type splicing pattern of the corresponding mRNA; an alteration in the level of the corresponding polypeptide; and/or an alteration in corresponding polypeptide activity.

Detection of a target polymorphism by analyzing a polynucleotide sample can be conducted in a number of ways. A test nucleic acid sample can be amplified with primers which amplify a region known to comprise the target polymorphism(s). Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "*PCR Protocols (Methods in Molecular Biology)*" (2000) J. M. S. Bartlett and D. Stirling, eds, Humana Press; and "*PCR Applications: Protocols for Functional Genomics*" (1999) Innis, Gelfand, and Sninsky, eds., Academic Press. Once the region comprising a target polymorphism has been amplified, the target polymorphism can be detected in the PCR product by nucleotide sequencing, by SSCP analysis, or any other method known in the art. In performing SSCP analysis, the PCR product may be digested with a restriction endonuclease that recognizes a sequence within the PCR product generated by using as a template a reference sequence, but does not recognize a corresponding PCR product generated by using as a template a variant sequence by virtue of the fact that the variant sequence no longer contains a recognition site for the restriction endonuclease. PCR may also be used to determine whether a polymorphism is present by using a primer that is specific for the polymorphism. Such methods may comprise the steps of collecting from an individual a biological sample comprising the individual's genetic material as template, optionally isolating template nucleic acid (genomic DNA, mRNA, or both) from the biological sample, contacting the template nucleic acid sample with one or more primers that specifically hybridize with a target polymorphic nucleic acid molecule under conditions such that hybridization and amplification of the template nucleic acid molecules in the sample occurs, and detecting the presence, absence, and/or relative amount of an amplification product and comparing the length to a control sample. Observation of an amplification product of the expected size is an indication that the target polymorphism contained within the target polymorphic primer is present in the test nucleic acid sample. Parameters such as hybridization conditions, polymorphic primer length, and position of the polymorphism within the polymorphic primer may be chosen such that hybridization will not occur unless a polymorphism present in the primer(s) is also present in the sample nucleic acid. Those of ordinary skill in the art are well aware of how to select and vary such parameters. See, e.g., Saiki et al. (1986) *Nature* 324:163; and Saiki et al (1989) *Proc. Natl. Acad. Sci. USA* 86:6230. As one non-limiting example, a PCR primer comprising the T78C variation described in Example 1 may be used.

Alternatively, various methods are known in the art that utilize oligonucleotide ligation as a means of detecting polymorphisms. See, e.g., Riley et al. (1990) *Nucleic Acids Res.* 18:2887-2890; and Delahunty et al., (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid may be sequenced by a dideoxy chain termination method or other well-known methods. Genomic DNA or mRNA may be used directly. If mRNA is used, a cDNA copy may first be made. If desired, the sample nucleic acid can be amplified using a PCR. A variety of sequencing reactions known in the art can be used to directly sequence the relevant gene, or a portion thereof in which a specific polymorphism is known to occur, and detect polymorphisms by comparing the sequence of the sample nucleic acid with a reference polynucleotide that contains a target polymorphism. Any of a variety of automated sequencing procedures can be used. See, e.g., WO 94/16101; Cohen et al. (1996) *Adv. Chromatography* 36:127-162.

Hybridization with the variant sequence may also be used to determine the presence of a target polymorphism. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Identification of a polymorphism in a nucleic acid sample can be performed by hybridizing a sample and control nucleic acids to high density arrays containing hundreds or thousands of oligonucleotide probes. Cronin et al., (1996) *Human Mutation* 7:244-255; and Kozal et al., (1996) *Nature Med.* 2:753-759.

Single strand conformational polymorphism (SSCP) analysis; denaturing gradient gel electrophoresis (DGGE); mismatch cleavage detection; and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels. The aforementioned techniques are well known in the art. Detailed description of these techniques can be found in a variety of publications, including, e.g., "*Laboratory Methods for the Detection of Mutations and Polymorphisms in DNA*" (1997) G. R. Taylor, ed., CRC Press, and references cited therein.

A number of methods are available for determining the expression level of a polymorphic nucleic acid molecule, e.g., a polymorphic mRNA, or polymorphic polypeptide in a particular sample. Diagnosis may be performed by a number of methods to determine the absence or presence or altered amounts of normal or abnormal mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a polymorphic polypeptide may also be detected and/or quantitated in any of a variety of published procedures.

Alternatively, one may focus on the expression of mRNA. Biochemical studies may be performed to determine whether a sequence polymorphism in a coding region or control regions is associated with disease. Disease associated polymorphisms may include deletion or truncation of the gene, mutations that alter expression level, that affect the activity of the protein, etc.

Screening for mutations in a polymorphic polypeptide may be based on the functional or antigenic characteristics of the protein. Protein truncation assays are useful in detecting deletions that may affect the biological activity of the protein. Various immunoassays designed to detect polymorphisms in polymorphic polypeptides may be used in screening. Where many diverse genetic mutations lead to a particular disease phenotype, functional protein assays have proven to be effective screening tools. The activity of the encoded a polymorphic polypeptide may be determined by comparison with a reference polypeptide lacking a specific polymorphism.

Diagnostic methods of the subject disclosure in which the level of polymorphic gene expression is of interest will typically involve comparison of the relevant nucleic acid abundance of a sample of interest with that of a control value to determine any relative differences, where the difference may be measured qualitatively and/or quantitatively, which differences are then related to the presence or absence of an abnormal gene expression pattern. A variety of different methods for determining the nucleic acid abundance in a sample are known to those of skill in the art, where particular methods of interest include those described in: Pietu et al., *Genome Res.* (June 1996) δ: 492-503; Zhao et al., *Gene* (Apr. 24, 1995) 156: 207-213; Soares, *Curr. Opin. Biotechnol.* (October 1997) δ: 542-546; Raval, *J. Pharmacol. Toxicol. Methods* (November 1994) 32: 125-127; Chalifour et al., *Anal. Biochem.* (Feb. 1, 1994) 216: 299-304; Stolz & Tuan, *Mol. Biotechnol.* (December 19960 6: 225-230; Hong et al., *Bioscience Reports* (1982) 2: 907; and McGraw, *Anal. Biochem.* (1984) 143: 298. Also of interest are the methods disclosed in WO 97/27317, the disclosure of which is herein incorporated by reference.

Additional references describing various protocols for detecting the presence of a target polymorphism include, but are not limited to, those described in: U.S. Pat. Nos. 6,703,228; 6,692,909; 6,670,464; 6,660,476; 6,653,079; 6,632,606; 6,573,049; the disclosures of which are herein incorporated by reference.

Following obtainment of the genotype from the sample being assayed, the genotype is evaluated to determine whether the subject is responsive to the antineoplastic therapy of interest. In certain embodiments, the obtained genotype may be compared with a reference or control to make a diagnosis regarding the therapy responsive phenotype of the cell or tissue, and therefore host, from which the sample was obtained/derived. The terms "reference" and "control" as used herein mean a standardized genotype to be used to interpret the genotype of a given patient and assign a prognostic class thereto. The reference or control may be a genotype that is obtained from a cell/tissue known to have the desired phenotype, e.g., responsive phenotype, and therefore may be a positive reference or control genotype. In addition, the reference/control genotype may be from a cell/tissue known to not have the desired phenotype, and therefore be a negative reference/control genotype.

In certain embodiments, the obtained genotype is compared to a single reference/control genotype to obtain information regarding the phenotype of the cell/tissue being assayed. In yet other embodiments, the obtained genotype is compared to two or more different reference/control profiles to obtain more in depth information regarding the phenotype of the assayed cell/tissue. For example, the obtained genotype may be compared to a positive and negative genotype to obtain confirmed information regarding whether the cell/tissue has the phenotype of interest.

Representative examples of genotypes associated with therapy responsiveness, particularly Rituximab responsive include, but are not limited to: the FcγRIIA H/H$^{131}$ genotype and the FcγRIIIA V/V$^{158}$ genotype. Representative examples of genotypes associated with therapy non-responsiveness, particularly Rituximab-non responsiveness include, but are not limited to: the FcγRIIA H/R$^{131}$ genotype; the FcγRIIA R/R$^{131}$ genotype; the FcγRIIIA V/F$^{158}$ genotype; and the FcγRIIIA F/F$^{158}$ genotype.

In certain embodiments, the above-obtained information about the cell/tissue being assayed is employed to diagnose a host, subject or patient with respect to responsive to therapeutic antibody therapy, as described above. In certain embodiments, the above-obtained information is employed to give a refined probability determination as to whether a subject will or will not respond to a particular therapy. For example, an identification of the FcγRIIA H/H$^{131}$ genotype and/or the FcγRIIIA V/V$^{158}$ genotype may be employed to determine that the subject has at least a 70% chance, such as at least a 75% chance, including at least an 80% chance of responding to antibody, e.g., Rituximab, therapy. Likewise, an identification of the FcγRIIA H/R$^{131}$ or R/R$^{131}$ genotype and/or the FcγRIIIA V/F$^{158}$ or F/F$^{158}$ genotype may be employed to determine that the subject has less than 50% chance, such as a less than 45% chance, including a less than 40% chance of responding to antibody, e.g., Rituximab, therapy.

The subject methods further find use in pharmacogenomic applications. In these applications, a subject is first diagnosed for the presence of absence of a responsive phenotype using a protocol such as the diagnostic protocol described in the preceding section.

The subject is then treated using a pharmacological protocol, where the suitability of the protocol for a particular subject/patient is determined using the results of the diagnosis step. More specifically, where the identified phenotype is responsive, an appropriate therapeutic antibody treatment protocol is then employed to treat the patient. Alternatively, where a patient is identified as having a non-responsive phenotype, other treatment options are sought.

Methods for Selecting a Patient for Treatment with an Antibody

Methods are provided for selecting a patient for treatment with an antibody or antibody fragment based on the patient's FcγRIIA and FcγRIIIA polymorphism. For example, a patient with a particular FcγRIIA (H/R$^{131}$) polymorphism and a FcγRIIIA (V/F$^{158}$) polymorphism is selected for treatment with one or more antibody therapies.

Methods are provided for selecting a patient for treatment with an antibody, comprising: (a) determining if the patient has an FcγRIIIA V/V$^{158}$ genotype, an FcγRIIIA V/F$^{158}$ or an FcγRIIIA F/F$^{158}$ genotype; (b) determining if the patient has an FcγRIIA H/H$^{131}$ genotype, an FcγRIIA H/R$^{131}$ genotype or an FcγRIIA R/R$^{131}$ genotype; (c) selecting the patient with a particular genotype for treatment with the antibody based on the genotype determination of steps (a) and (b); and (d) administering the antibody to the patient selected in step (c).

A patient is assigned to one of nine Groups according to their FcγRIIA(H/R$^{131}$) polymorphism and a FcγRIIIA (V/F$^{158}$) polymorphism. Genotypes include: V/V$^{158}$, H/H$^{131}$ (Group-I); V/F$^{158}$, H/H$^{131}$ (Group-II); F/F$^{158}$, H/H$^{131}$ (Group-III); V/V$^{158}$, H/R$^{131}$ (Group-IV); V/F$^{158}$, H/R$^{131}$ (Group-V); F/F$^{158}$, H/R$^{131}$ (Group-VI); V/V$^{158}$, R/R$^{131}$ (Group-VII); V/F$^{158}$, R/R$^{131}$ (Group-VIII); and F/F$^{158}$, R/R$^{131}$ (Group-IX). Accordingly, a patient with one of the above-described genotypes is selected for treatment with one or more antibody therapies.

In some embodiments, the antibody, variable region of an antibody or Fc variant antibody is selected from the Group group RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), LUCENTIS® (ranibizumab), SOLIRIS® (eculizumab), OKT3® (muromonab-CD3), BEXXAR® (tositumomab), ZEVALIN® (ibritumomab tiuxetan), ENBREL® (etanercept) or AMEVIVE® (alefacept).

Methods of Determining a Degree of Responsiveness

Methods are provided for determining the degree of treatment response that an individual having an ADCC-treatable disease or disorder will have to an antibody therapy for the disease or disorder. The methods generally involve: a) genotyping an individual having a disease or disorder that is treatable with an ADCC-based antibody therapy, to determine an FcγRIIA polymorphism to obtain a first result; b) genotyping the individual to determine an FcγRIIIA polymorphism to obtain a second result; and c) employing the first and second results to determine the degree of responsiveness of the individual to the antibody therapy.

Diseases and disorders that are treatable with an ADCC-based antibody therapy include, but are not limited to, neoplastic diseases; autoimmune diseases; allograft rejection, and microbial infections.

Thus, e.g., in some embodiments, methods are provided for determining the degree of responsiveness that an individual having a neoplastic disease will have to an antibody therapy. The methods generally involve: a) genotyping an individual having a neoplastic disease, to determine an FcγRIIA polymorphism to obtain a first result; b) genotyping the individual to determine an FcγRIIIA polymorphism to obtain a second result; and c) employing the first and second results to determine the degree of responsiveness of the individual to the antibody therapy.

In other embodiments, methods are provided for determining the degree of responsiveness that a subject having an ADCC-treatable disease or disorder will have to an antibody therapy for the disease or disorder, the method comprising: (a) genotyping the subject for an FcγRIIA polymorphism and a FcγRIIIA polymorphism; and (b) identifying a genotype associated with a particular degree of responsiveness to the antibody therapy from a reference that is identical to the genotype from the test subject, wherein the test subject is determined to have a degree of responsiveness to the antibody therapy for the disease or disorder corresponding to the level of responsiveness associated with the reference having an identical FcγRIIA polymorphism and an identical FcγRIIIA polymorphism.

In a further embodiment, methods are provided for determining the degree of responsiveness that a test subject having an ADCC-treatable disease or disorder will have to an antibody therapy for the disease or disorder, the method comprising: (a) genotyping subjects for a FcγRIIA polymorphism and a FcγRIIIA polymorphism, wherein the subjects have or had the ADCC-treatable disease or disorder and are or were administered antibody therapy for the disease or disorder; (b) classifying each subject based on its FcγRIIA polymorphism and FcγRIIIA polymorphism to one of more than three categories of responsiveness to the antibody therapy; (c) genotyping the test subject for an FcγRIIA polymorphism and a FcγRIIIA polymorphism; and (d) identifying a genotype from (a) that is identical to the genotype from the test subject in step (c), wherein the test subject is determined to have a degree of responsiveness to the antibody therapy for the disease or disorder corresponding to the level of responsiveness associated with a subject having an identical FcγRIIA polymorphism and an identical FcγRIIIA polymorphism.

The predicted responsiveness of an individual to an antibody therapy may be categorized into a plurality of different categories based on first and second results, such as three or more different categories, e.g., a) "high degree of responsiveness": the individual has at least a 65% chance, at least a 70% chance, at least a 75% chance, or at least an 80% chance, or greater, of responding to the antibody therapy; b) "intermediate degree of responsiveness": the individual has from about a 35% chance to about a 65% chance, or from about a 50% chance to about a 70% chance, of responding to the antibody therapy; and c) "low degree of responsiveness": the individual has a less than 50% chance, less than 45% chance, or less than 40% chance, of responding to the antibody therapy.

Responsiveness may be determined at various times after treatment with a given antibody therapy, e.g., 1-3 months, 3-6 months, 6-9 months, or 9-12 months following treatment, e.g., following initiation of treatment. Thus, e.g., responsiveness can be expressed with a time component.

For example, in some embodiments, predicted responsiveness of an individual to an antibody therapy may be categorized into a plurality of different categories based on first and second results, such as three or more different categories, e.g., a) "high degree of responsiveness": the individual has at least a 65% chance, at least a 70% chance, at least a 75% chance, or at least an 80% chance, or greater, of responding to the antibody therapy at one month following initiation of treatment; b) "intermediate degree of responsiveness": the individual has from about a 35% chance to about a 65% chance, or from about a 50% chance to about a 70% chance, of responding to the antibody therapy at one month following initiation of treatment; and c) "low degree of responsiveness": the individual has a less than 50% chance, less than 45% chance, or less than 40% chance, of responding to the antibody therapy at one month following initiation of treatment.

In other embodiments, predicted responsiveness of an individual to an antibody therapy may be categorized into a plurality of different categories based on first and second results, such as three or more different categories, e.g., a) "high degree of responsiveness": the individual has at least a 65% chance, at least a 70% chance, at least a 75% chance, or at least an 80% chance, or greater, of responding to the antibody therapy at three months following initiation of treatment; b) "intermediate degree of responsiveness": the individual has from about a 35% chance to about a 65% chance, or from about a 50% chance to about a 70% chance of responding to the antibody therapy at three months following initiation of treatment; and c) "low degree of responsiveness": the individual has a less than 50% chance, less than 45% chance, or less than 40% chance, of responding to the antibody therapy at three months following initiation of treatment.

In other embodiments, predicted responsiveness of an individual to an antibody therapy may be categorized into a plurality of different categories based on first and second results, such as three or more different categories, e.g., a) "high degree of responsiveness": the individual has at least a 65% chance, at least a 70% chance, at least a 75% chance, or at least an 80% chance, or greater, of responding to the antibody therapy at six months following initiation of treatment; b) "intermediate degree of responsiveness": the individual has from about a 35% chance to about a 65% chance, or from about a 50% chance to about a 70% chance of responding to the antibody therapy at six months following initiation of treatment; and c) "low degree of responsiveness": the individual has a less than 50% chance, less than 45% chance, or less than 40% chance, of responding to the antibody therapy at six months following initiation of treatment.

In other embodiments, predicted responsiveness of an individual to an antibody therapy may be categorized into a plurality of different categories based on first and second results, such as three or more different categories, e.g., a) "high degree of responsiveness": the individual has at least a 65% chance, at least a 70% chance, at least a 75% chance, or at least an 80% chance, or greater, of responding to, the antibody therapy at 12 months following initiation of treatment; b) "intermediate degree of responsiveness": the individual has from about a 35% chance to about a 65% chance, or from about a 50% chance to about a 70% chance of responding to the antibody therapy at 12 months following initiation of treatment; and c) "low degree of responsiveness": the individual has a less than 50% chance, less than 45% chance, or less than 40% chance, of responding to the antibody therapy at 12 months following initiation of treatment.

Responsiveness to an antibody therapy for a neoplastic disease can include one or more of: antibody-dependent cell-mediated cytotoxicity (ADCC) response to tumor cells; reduction in tumor mass; reduction in number of tumor cells; etc. Responsiveness to an antibody therapy for an autoimmune disease can include one or more of: reduction in a symptom associated with the autoimmune disorder; reduction in the number and/or activity of an autoreactive B-cell; reduction in the number and/or activity of an autoreactive T-cell; etc. Responsiveness to an antibody therapy for allograft rejection can include one or more of: reduction in the amount of immunosuppressive drug that must be administered to an individual who is the recipient of an allograft and still maintain the allograft; duration of maintenance of the allograft; function of the allograft; reduction in the number and/or activity of alloreactive T-cells in the allograft recipient. Responsiveness to an antibody therapy for a viral infection can include one or more of: reduction in the number of viral genomes in a tissue, fluid, or other specimen from an individual; reduction in one or more symptoms of a viral infection; etc. Responsiveness can also be assessed using an in vitro ADCC assay, e.g., as described in the Examples.

For example, where an FcγRIIIA polymorphism can be one of A/A, A/a, and a/a, and where an FcγRIIA polymorphism can be one of B/B, B/b, and b/b, responsiveness to a given antibody therapy at a given time point after treatment may be categorized as shown in Tables A and B, below. A/A, a/a, B/B, and b/b represent homozygous alleles for the respective FcγR polymorphisms, while A/a and B/b represent heterozygous alleles for the respective FcγR polymorphisms.

TABLE A

|  | FcγRIIIA Genotype A/A | FcγRIIIA Genotype A/a | FcγRIIIA Genotype a/a |
| --- | --- | --- | --- |
| FcγRIIA Genotype B/B | 70%-100% | 50%-70% | 50%-70% |
| FcγRIIA Genotype B/b | 50%-70% | <50% | <50% |
| FcγRIIA Genotype b/b | 50%-70% | <50% | <50% |

TABLE B

Allelic expression patterns based on FcγRIIIA and FcγRIIA polymorphisms in various patient Groups

| | FcγRIIIA Genotype A/A | FcγRIIIA Genotype A/a | FcγRIIIA Genotype a/a |
|---|---|---|---|
| FcγRIIA Genotype B/B | Group I 70%-100% A, A; B, B | Group II 50%-70% A, a; B, B | Group III 50%-70% a, a; B, B |
| FcγRIIA Genotype B/b | Group IV 50%-70% A, A; B, b | Group V <50% A, a; B, b | Group VI <50% a, a; B, b |
| FcγRIIA Genotype b/b | Group VII 50%-70% A, A; b, b | Group VIII <50% A, a; b, b | Group IX <50% a, a; b, b |

For a given antibody (a "reference antibody") with responsiveness categories as set forth in Table A or Table B, Table A or Table B is an exemplary reference chart. A person with unknown responsiveness to therapy with the reference antibody is genotyped for FcγRIIA and FcγRIIIA polymorphisms; and the person's genotype is compared with the reference chart; and the degree of predicted responsiveness is determined from the reference chart. In some embodiments, where the predicted degree of responsiveness is high, the individual will be treated with an antibody that is the same as the reference antibody. In other embodiments, where the predicted degree of responsiveness is intermediate (e.g., 50%-70%) or low (e.g., <50%), a therapeutic antibody will be selected that has the same antigen binding specificity as the reference antibody, but has enhanced in vitro ADCC activity to an FcγRIIA and/or an FcγRIIIA, as described in more detail below. The nature of allelic expression for the above genotypes can be best described by codominance. For example, for the Patient Group-V (Table B) with genotypes FcγRIIIA (A/a) and FcγRIIA (B/b) will have equal phenotypic expression of both alleles A,a for FcγRIIIA and B,b for FcγRIIA. In some embodiments, individuals of category (a) will have an FcγRIIA H/H$^{131}$ genotype and an FcγRIIIA V/V$^{158}$ genotype. In some embodiments, individuals of category (b) will have an FcγRIIA H/H$^{131}$ genotype or an FcγRIIIA V/V$^{158}$ genotype, but not both. For example, individuals of category (b) will have one of: i) an FcγRIIA H/H$^{131}$ genotype and an FcγRIIIA V/F$^{158}$ genotype; ii) an FcγRIIA H/H$^{131}$ genotype and an FcγRIIIA 158 F/F genotype; iii) an FcγRIIA H/R$^{131}$ genotype and an FcγRIIIA V/V$^{158}$ genotype; or iv) an FcγRIIA R/R$^{131}$ genotype and an FcγRIIIA V/V$^{158}$ genotype. Individuals of category (c) will have neither an FcγRIIA H/H$^{131}$ genotype nor an FcγRIIIA V/V$^{158}$ genotype. Thus, e.g., in some embodiments, individuals of category (c) will have one of: i) an FcγRIIA H/R$^{131}$ genotype and an FcγRIIIA V/F$^{158}$ genotype; ii) an FcγRIIA R/R$^{131}$ genotype and an FcγRIIIA V/F$^{158}$ genotype; iii) an FcγRIIA H/R$^{131}$ genotype and an FcγRIIIA F/F$^{158}$ genotype; or iv) an FcγRIIA R/R$^{131}$ genotype and an FcγRIIIA F/F$^{158}$ genotype. The nature of allelic expression for the above genotypes can be best described by codominance. For example, for the Patient Group-V (Table B) with genotypes FcγRIIIA (V/F) and FcγRIIA (H/R) will have equal phenotypic expression of both alleles V,F for FcγRIIIa and H,R for FcγRIIA. Both FcγRIIIA and FcγRIIA are monomers under physiological conditions, and the number of these receptors can be ~15,000-35,000 per cell (Guyre et al., *J. Clin. Invest.* 72:393-397, 1983). Individuals with a FcγRIIIA V/F$^{158}$ genotype will express equal number of V$^{158}$ and F$^{158}$ alleles. Similarly, individuals with a FcγRIIA 131H/R genotype will express equal number of H$^{131}$ and R$^{131}$ alleles.

As an example, a reference chart with various combinations of FcγRIIA and FcγRIIIA polymorphisms, and corresponding categories of anticipated responsiveness to a monoclonal antibody therapy (e.g., Rituxan), are shown in Table C, below.

TABLE C

| | FcγRIIIA 158 V/V | FcγRIIIA V/F | FcγRIIIA F/F |
|---|---|---|---|
| FcγRIIA 131H/H | 70%-100% | 50%-70% | 50%-70% |
| FcγRIIA 131 H/R | 50%-70% | <50% | <50% |
| FcγRIIA 131 R/R | 50%-70% | <50% | <50% |

TABLE D

Allelic expression patterns based on FcγRIIIA and FcγRIIA polymorphisms in various patient Groups (n = 87)

| | FcγRIIIA V/V$^{158}$ | FcγRIIIA V/F$^{158}$ | FcγRIIIA F/F$^{158}$ | Total (%) |
|---|---|---|---|---|
| FcγRIIA H/H$^{131}$ | Group-I 70%-100% V, V; H, H 3 (3.4) | Group-II 50%-70% V, F; H, H 14 (16.1) | Group-III 50%-70% F, F; H, H 3 (3.4) | 20 (23) |
| FcγRIIA H/R$^{131}$ | Group-IV 50%-70% V, V; H, R 8 (9.2) | Group-V <50% V, F; H, R 16 (18.4) | Group-VI <50% F, F; H, R 19 (21.8) | 19 (21.8) |
| FcγRIIA R/R$^{131}$ | Group-VII 50%-70% V, V; R, R 2 (2.3) | Group-VIII <50% V, F; R, R 10 (11.5) | Group-IX <50% F, F; R, R 12 (13.8) | 12 (13.8) |
| Total (%) | 13 (14.9) | 40 (46) | 34 (39.1) | 87 (100) |

Table D is another example of a reference chart. The V$^{158}$ allele in FcγRIIIA is a high-affinity/high-responder receptor while the F$^{158}$ allele is a low-affinity/low-responder receptor. Similarly, the H$^{131}$ allele in FcγRIIA is a high-affinity/high-responder receptor while the R$^{131}$ allele is a low-affinity/low-responder receptor. The polymorphisms were determined in an expanded Group of 87 patients with follicular lymphoma (Table D; FIG. 13). The allelic frequencies are: pV=0.38, pF=0.62; pH=0.48; pR=0.52.

Further, FcγRIIIA and FcγRIIA were determined for populations of healthy U.S. Caucasians, healthy U.S. African Americans and healthy Norwegians. Interestingly, these groups exhibited a similar allelic expression pattern as the patient group with B-NHL (FIG. 14).

As an example, a reference chart with various combinations of FcγRIIA and FcγRIIIA polymorphisms, and corresponding categories of anticipated responsiveness to a monoclonal antibody therapy (e.g., Rituxan), are shown in Table D, above.

In some embodiments, an FcγRIIIA genotype and an FcγRIIA genotype are determined using a nucleic acid probe that hybridizes under stringent hybridization conditions to FcγRIIA-encoding and FcγRIIIA-encoding nucleic acids comprising polymorphisms associated with an altered response to treatment with a therapeutic antibody. FcγRIIA-encoding and FcγRIIIA-encoding nucleic acids (referred to collectively herein as "target nucleic acids") are in some embodiments genomic DNA that comprise nucleotide sequences encoding all or part of an FcγRIIA or an FcγRIIIA, and that include a polymorphism associated with a response to an antibody therapeutic. In other embodiments, an FcγRIIIA genotype and an FcvRIIA genotype are determined using nucleic acid primer pairs that, in the presence of an appropriate polymerase and other reagents (e.g., dNTPs, ions such as magnesium ions, etc.), prime the synthesis of an amplification product using the target nucleic acids as templates, using, e.g., a polymerase chain reaction. The target nucleic acids are chosen such that they include at least one polymorphic region. For example, a first primer pair primes amplification of an FcγRIIA target nucleic acid that comprises the polymorphism that gives rise to $H/H^{131}$, $H/R^{131}$, or $R/R^{131}$; and a second primer pair primes amplification of an FcγRIIIA target nucleic acid that comprises a polymorphism that gives rise to $V/V^{158}$, $V/F^{158}$, or $F/F^{158}$. A nucleic acid primer will in some embodiments include a detectable label, which detectable label is incorporated into the amplification product, giving rise to a detectably labeled amplification product. A nucleic acid primer will in some embodiments include a restriction endonuclease recognition site not found in the template or in other nucleic acid primers, such that an amplification product is generated which includes a restriction endonuclease recognition site that provides for its identification.

ADCC Mediated by NK-Cells and Macrophages

The presence of infiltrating NK cells and macrophages in surgically removed tumors from MAb-treated patients has been extensively documented (Adams et al. *Proc. Natl. Acad. Sic. USA* 81:3506, 1984; Shetye et al. *Cancer Immunol. Immunother.* 27:154, 1988). Although both ADCC and CDC may play a role in tumor cell destruction in vivo, as substantiated by several in vitro studies, the main anti-tumor mechanism of therapeutic antibodies in vivo is considered to be ADCC (See, e.g., Velders et al. *British J. Cancer* 78:478, 1998).

ADCC can be classified into two types: NK-cell mediated ADCC (NK-ADCC) and macrophage-mediated ADCC (M-ADCC). Both mechanisms either independently or together can be viewed to play significant roles in mediating cytotoxicities, and have direct relevance in determining the clinical efficacy of MAb therapies (Carton et al. *Blood* 99:754, 2002; Weng and Levy, *J. Clin. Oncol.* 21:3940, 2003; Cheung et al. *J. Clin. Oncol.* 24:2885, 2006).

Most tumor cells appear to secrete chemoattractants which actively recruit monocytes to tumor sites (Graves et al. *Science* 245:1490, 1989; Bottazzi et al. *Science* 220:210, 1983). The mechanism of ADCC by these MDM (monocyte-derived macrophages) appears to involve phagocytosis of intact tumor cells (Munn and Cheung, *J. Exp. Med.* 172:231, 1990; Munn et al. *Cancer Research* 51:1117, 1991). Thus, in one embodiment, macrophages are important in immunotherapeutic regimens involving anti-tumor ADCC.

Macrophages express three FcγRs for IgG: the high-affinity receptor, FcγRI, and the two low-affinity receptors, FcγRIIA and FcγRIIIA FcγRI avidly binds monomeric human IgG ($K_a \sim 2 \times 10^8 \, M^{-1}$), and therefore the binding of monoclonal antibody is competitively inhibited by serum immunoglobulin.

FcγRIIIA is present in NK cells (FcγRIIIA$_{NK}$) and macrophages (FcγRIIIA$_M$). FcγRIIA is preferentially expressed on macrophages and neutrophils, and not on lymphocytes. Although FcγRIIIA$_{NK}$ and FcγRIIIA$_M$ have identical protein cores, they each undergo differential cell type-specific glycosylation: FcγRIIIA$_{NK}$ is glycosylated with high mannose- and complex-type oligosaccharides, while FcγRIIIA$_M$ has no high mannose-type oligosaccharides. Because of this, FcγRIIIA$_{NK}$ exhibits higher affinity for IgG, and this feature is not influenced by VF$^{158}$ allelic polymorphism (Edberg and Kimberly, *J. Immunol.* 159:3849, 1997). In normal whole blood or plasma (containing 8-11 mg/ml IgG), FcγRIIIA$_{NK}$ was fully blocked, but FcγRIIIA$_M$ showed approximately 60% blockade of the binding of mAB 3G8, which binds in or near the ligand binding site. The ligand binding site of FcγRIIIA$_{NK}$ was blocked with as little as 2 mg/ml of human IgG, while FcγRIIIA$_M$ was only partially (30%) blocked at this concentration. In contrast, plasma containing approximately 26 mg/ml of IgG (obtained from Immune Thrombocytopenic Purpura patients receiving therapeutic g-globulin) showed complete saturation of FcγRIIIA$_M$ with blockade of 3G8 binding. Binding of mAB IV.3, an FcγRIIA-specific MAb, to the low affinity FcγRIIA on monocytes was unaltered by exposure of the cells to the same ITP patient plasmas. Thus, in one embodiment, the ligand binding properties of FcγRIIIA$_{NK}$ and FcγRIIIA$_M$ are distinctly different (Edberg and Kimberly, supra). In another embodiment, therefore, the ADCC levels mediated by the FcγRIIIA$_{NK}$ and FcγRIIIA$_M$ are expected to be significantly different.

The FcγRIIIA VF$^{158}$ polymorphism is a clinically relevant phenotype that has a direct impact on human biology (Wu et al. *J. Clin. Invest.* 100:1059, 1997). Compared with FF$^{158}$ homozygotes, FcγRIIIA expressed on NK cells and monocytes in VV$^{158}$ homozygotes bound more IgG$_1$ and IgG$_3$ despite identical levels of receptor expression. In response to a standard aggregated human IgG stimulus, FcγRIIIA engagement on NK cells from VV$^{158}$ (high binding) homozygotes led to a larger rise in [Ca$^{2+}$]$_i$, a greater level of NK cell activation, and a more rapid induction of activation-induced cell death (by apoptosis). Investigation of an independently phenotyped normal cohort revealed that all donors with a low binding phenotype are FF$^{158}$ homozygotes, while all phenotypic high binding donors have at least one V$^{158}$ allele (either VV or VF). Initial analyses of 200 patients with systemic lupus erythematosus (SLE) indicates a strong association of the low-binding phenotype (FF$^{158}$) with disease, especially in patients with nephritis who have an underrepresentation of the homozygous high binding (VV$^{158}$) phenotype (FF, 44%; VF, 46%; VV, 10%). This VF$^{158}$ polymorphism based variations in IgG binding was further correlated to the earlier observations that some patients have "high" NK-cell mediated ADCC (Vance et al. *J. Immunol.* 151:6429, 1993).

Some forms of macrophage ADCC have been reported to be inhibited by serum IgG, which competes with monoclonal antibodies for binding to FcγRI. Hybridoma cells bearing surface antibody directed against either of FcγRs (II and III) were efficiently phagocytosed by MDM (Munn et. al. *Cancer Research* 51:1117, 1991). Soluble anti-receptor antibodies against FcγRII and FcγRIII were able to inhibit ADCC but only when both antibodies were simultaneously present suggesting that either FcγR is capable of functioning independently to mediate phagocytosis of tumor cells. Consistent with the mechanism involving the low-affinity receptors rather than FcγRI, antibody-dependent phagocytosis occurred in the presence of human serum and purified human IgG. Greater than 75% of the MDM were able to ingest tumor cells when a suitable target cell was available (Munn et. al., supra). Optimal phagocytosis occurred at monoclonal antibody concentrations of 10-100 ng/ml. Because FcγRI is normally occupied in vivo by serum IgG, the participation of both low-affinity FcγRs in tumor cell phagocytosis is potentially important in establishing the in vivo applicability of this efficient form of toxicity (Munn et. al., supra).

C-reactive protein (CRP) is involved in host defense, regulation of inflammation, and modulation of autoimmune disease. CRP shares several functional activities with IgG including binding to FcγRs (Crowell et al. *J. Immunol.* 147: 3445, 1991; Marvell et al. *J. Immunol.* 155:2185, 1995). Direct genetic evidence for FcγRIIA as the functional, high affinity CRP receptor on monocytes/leukocytes has been provided, and this study emphasized the reciprocal relationship between IgG and CRP avidities (Stein et. al. *J. Clin. Invest.* 105: 369, 2000). FcγRIA binds CRP with low affinity, whereas FcγRIIA binds CRP with high affinity. CRP bound with high avidity to monocytes and neutrophils from FcγRIIA-RR$^{131}$ homozygotes. CRP showed decreased binding to cells from FcγRIIA-HH$^{131}$ homozygotes. That is, both IgG$_1$, for instance, an antibody therapy such as rituximab, and CRP will compete for the same binding site in FcγRIIA, and is further influenced by the HR$^{131}$ polymorphism. FcγRIIA-HR$^{131}$ heterozygotes showed intermediate binding. These findings provide direct genetic evidence for FcγRIIA as the functional, high affinity CRP receptor on leukocytes while emphasizing the reciprocal relationship between IgG and CRP binding avidities (Stein et al. supra). Thus, in one embodiment, the M-ADCC is the sum of ADCC mediated by the FcγRIIIA and FcγRIIA. In another embodiment, the M-ADCC is influenced by both VF$^{158}$ and HR131 polymorphisms.

The murine IgG$_3$ anti-GD2 MAb 3F8 is being used in the clinic for its antitumor activity in high-risk neuroblastoma patients. The MAb exhibits potent in vitro ADCC activity (Kushner et. al., *Blood* 73:1936, 1989), and its phagocyte-mediated ADCC is markedly increased in the presence of GM-CSF. ELISA studies showed 3F8 has preferential binding to FcγRIIA-R$^{131}$ over FcγRIIA-H$^{131}$. The role of FcγRIIA-HR$^{131}$ and FcγRIIIA-VF$^{158}$ polymorphisms with clinical outcome of high-risk neuroblastoma patients (N=136) treated with 3F8 and GM-CSF was investigated (Cheung et. al., *J. Clin. Oncol.* 24:2885, 2006). FcγRIIA-RR$^{131}$ genotype correlated with progression-free survival for the entire cohort (P=0.049), and also correlated with marrow remission 2.5 months after treatment initiation. This finding is in stark contrast to what was shown for rituximab in B-NHL patients (Weng and Levy, supra), and can only be attributed to the fact that 3F8 is a mouse IgG$_3$ (Yan and Davis, *Pharmacogenomics* 7:961, 2006), whose hinge region is about four times longer than that of IgG$_1$ (Michaelsen et. al., *J. Biol. Chem.* 252:883, 1977, FIG. 18). Thus, in one embodiment, based on the H/R$^{131}$ polymorphisms, Fc variant IgG$_3$ antibodies can be generated with enhanced ADCC activity.

Therefore, in some embodiments, the Fc engineering is focused on optimizing both NK-ADCC and M-ADCC. In other embodiments, the Fc engineering is focused on optimizing the ADCC mediated by FcγRIIIA$_{NK}$ and FcγRIIIA$_M$. In some other embodiments, the Fc engineering is attempted to optimize the ADCC based on HR$^{131}$ polymorphism in FcγRIIA. In other embodiments, the Fc engineering is attempted to optimize the ADCC based on VF$^{158}$ polymorphism in FcγRIIIA.

Structure of Fc Region, Fc Receptors (FcR), and Fc-FcR Complexes

All known Fc receptors are members of the Ig super family, except for FcεRII. The crystal structures of the extracellular domains of FcγRII (Maxwell et al., *Nature Struct. Biol.* 6:437-442, 1999; Sondermann et al., *Biochemistry* 29:8469-77, 1999) and FcγRIII (Zhang et al., *Immunity* 13:387-395, 2000) show remarkable similarities. The receptors consist of two extracellular Ig-like domains, D1 and D2, with acute interdomain hinge angles of 50-55°, unique to Fc receptors. The Fc-binding region is located in the D2 domain. Additional crystal structures (Sondermann et al., *Nature* 406:267-73, 2000; Radaev et al., *J. Biol. Chem.* 276:16469-77, 2001; Sondermann et al., *J. Mol. Biol.* 309:737-749, 2001) have revealed that the receptor-ligand interface consists of the BC, C'E, FG loops and the Cβ strand of the D2 domain, the hinge loop between the D1 and D2 domains of the receptor providing additional interactions with FcγR (FIG. 12-C).

In the complex structure, the receptor is asymmetrically bound between the two Cγ2 domains of the Fc fragment creating a 1:1 receptor ligand stoichiometry. Only D2 of the sFcγRIII and two residues from the linker connecting this domain with D1 interact in the complex with different regions of both Cγ2 domains (Cγ2-A and Cγ2-B) and the preceding hinge regions of hFc1 (Fc from human IgG1; Sondermann et al., *Nature* 406:267-73, 2000; Sondermann et al., *J. Mol. Biol.* 309:737-749, 2001). Both FcγRIII and Fc components undergo substantial domain rearrangements upon binding but are restricted to the loops involved in the complex formation.

Fc Region—sFcγRIII Contact Interface:

sFcγRIII binds hFc1 with the B/C loop ($W^{110}$-$A^{114}$), the F/G loop ($V^{155}$-$K^{158}$), the C strand ($H^{116}$-$T^{119}$) and C' strand ($D^{126}$-$H^{132}$) on its carboxyl-terminal D2 (FIG. 12-C). Additionally, $R^{152}$ and the connector between the N-terminal D1 and D2 ($I^{85}$-$W^{87}$) is involved in binding. These regions interact with loops on the hFc1 within Cγ2-B (B/C: $D^{265}$-$E^{269}$, C'/E: $N^{297}$-$T^{299}$), with the F/G loop of Cγ2A ($A^{327}$-$I^{332}$), with the carbohydrate residue N-acetyl-D-glucosamine (NAG)1 of Cγ2-B and with the hinge region of both heavy chains ($L^{234}$-$S^{239}$). $N^{297}$ is the glycosylation site in the Fc region.

Two main contact areas exist. First, $P^{329}$ of Cγ2-A is encaged tightly by $W^{87}$ and $W^{110}$ of the FcγRIII ('proline sandwich'). Second, residues $L^{234}$-$S^{239}$ of the lower hinge of both hFc1 chains are engaged in sFcγRIII binding. These residues were disordered in the hFc1 crystal structures but are defined in the complex.

The receptor and the Fc fragment are in very close contact at the hinge region. $G^{237}$ of Cγ2-A and $G^{236}$ of Cγ2-B adopt Phi/Psi angles in the complex not allowed for other residues. The hinge residues $L^{234}$-$S^{239}$ of Cγ2-A are in contact with residues $T^{113}$, $A^{114}$ and $V^{155}$-$K^{158}$ of FcγRIII. The main contact is mediated by $L^{235}$ which binds in a shallow hydrophobic groove with $V^{155}$ at its bottom and the $A^{114}$ of the B/C loop, and $T^{113}$ Cγ2 at its rim (FIG. 12-C).

The hinge residues of the Cγ2-B domain are bound in a narrow channel of sFcγRIII lined by $H^{116}$ and $H^{132}$ on one side and $K^{117}$ on the other. The residues $G^{236}$ and $G^{237}$ of the hinge peptide bind into this channel and $Y^{129}$ and $H^{131}$ form additional contacts to the hinge peptide. In this arrangement, the residues $H^{116}$, $H^{131}$, and $H^{132}$ are potential hydrogen bond partners to hinge residues. $L^{235}$ is in contact with $H^{116}$ and $H^{132}$; this region is considerably more hydrophobic in other receptors.

The FcγRIII contacts the interstrand loops of the Cγ2-B domain and the terminal residues of the β-strands. The side chains of the residues $D^{126}$-$H^{131}$ (C' strand) are bound to the residues $D^{265}$-$E^{269}$, and $N^{297}$-$T^{299}$ of Cγ2-B. $R^{152}$ of the F strand could potentially form a hydrogen bond to the carbohydrate residue NAG1 that is directly attached to $N^{297}$ of Cγ2-B. Some more distant contacts to this sugar residue are formed by $K^{117}$, $T^{119}$, $D^{126}$, and $Y^{129}$ (See, e.g., FIG. 12-C). Substitution of Asparagine at position $N^{297}$ should lead to aglycosylated Fc form, which lacks ADCC activity but other functions such as CDC and FcRn binding are retained (Dorai et al., *Hybridoma* 10:211-217, 1991; Vaccaro et al., *Nature Biotechnol.* 23:1283-1287, 2005).

A sequence comparison of sFcγRIII with other FcγRs and the FcεRIα shows a high degree of similarity (FIG. 12-C). Mutagenesis studies with FcγRI (Canfield and Morrison, *J. Exp. Med.* 173:1483-91, 1991), FcγRII (Lund et al., *J. Immunol.* 147:2657-2662, 1991; Hulett et al., *J. Biol. Chem.* 269:15287-93, 1994; Hulett et al., *J. Biol. Chem.* 270:21188, 1995; Maxwell et al., *Nature Struct. Biol.* 6:437, 1999) and Fc☐RI☐ (Hulett et al., *J. Biol. Chem.* 274:13345, 1999) indicate that the same regions are involved in complex formation as are defined here for sFcγRIII. Therefore, based on several crystallographic and mutagenic studies, a common model describing the principal interactions within the various complexes can be proposed.

The proline sandwich appears as the primary binding motif in all FcR-Ig complexes. The two tryptophan residues ($W^{87}$ and $W^{110}$) are conserved in the FcRs including FcεRIα and the proline occurs in all IgGs and IgE. Further conserved contacts are observed between $K^{117}$ and $D^{265}$, T119 and NAG1, and $K^{128}$ and $E^{269}$ (the numbers in all Igs and FcRs refer to the homologous position in IgG1 and sFc☐RIII, respectively; FIG. 12-C).

The hinge peptide is a second central recognition site. The sequence variation in this region is likely to be the main reason for the differing affinities in the FcR-Ig pairs. The interactions seem to be modulated in different receptor Ig pairings in a productive or destructive way by the non-conserved regions of the binding loops.

FcγRII and FcγRIII are 50% identical and the differences affect the loops in contact with the hinge, but not the contact regions to Cγ2-A and Cγ2-B. The residues $G^{236}$ and $G^{237}$ of the Cγ2-B domain hinge peptide are bound in the narrow channel between $V^{116}$, $L^{132}$, and $K^{117}$. These exchanges at positions $V^{116}$ and $L^{132}$ create a small hydrophobic patch to which $L^{235}$ may bind and allow a tighter contact of receptor and hinge peptide.

Therefore, in some embodiments, amino acid sequence changes (e.g., insertions, deletions, substitutions, etc.) in one or more of the following conserved regions of IgG1-Fc region are expected to alter its binding properties to FcγRIIIA and FcγRIIA: $L^{234}$LGGPS$^{239}$; $R^{255}$TPEVT$^{260}$; $D^{265}$VSHE$^{269}$; $N^{297}$ST$^{299}$; $A^{327}$LPAPI$^{332}$. In other embodiments, based on the V/F and H/R polymorphisms, Fc variant antibodies can be generated with enhanced binding, potency, efficacy, and ADCC function specific to the patient Groups as exemplified in this disclosure. In some other embodiments, modification of additional residues involved in Fc engineering is accomplished through Fc Walking.

Methods of Making Sets of Related Antibodies

Methods are provided for making a set of related antibodies. The method generally involves:

a) modifying at least one Fc region amino acid residue in a parent antibody, such that the modified Fc region exhibits enhanced binding affinity to at least one Fc receptor encoded by an Fc receptor gene of a first genotype, compared to the Fc binding affinity of the parent antibody, to generate a first Fc region modified antibody (also referred to as an "Fc variant antibody"); and b) modifying at least one Fc region amino acid residue in a parent antibody, such that the modified Fc region exhibits enhanced binding affinity to at least one Fc receptor encoded by an Fc receptor gene of a second genotype, compared to the Fc binding affinity of the parent antibody, to generate a second Fc region modified antibody.

In other embodiments, methods are provided to modify the Fc region of an antibody to reduce its binding affinity to at least one Fc receptor compared to the Fc binding affinity of the parent antibody.

The parent antibody is a reference antibody. The first and second Fc region modified antibodies each differ in Fc region amino acid sequence by at least one amino acid from the Fc region amino acid sequence of the parent antibody, e.g., the first and the second Fc variant antibodies each independently comprise an Fc region amino acid sequence that differs in amino acid sequence from the Fc region of the parent antibody by one, two, three, four, five, six, seven, eight, nine, ten, 11, 12, 13, 14, 15, or more, amino acids. In some embodiments, the first and the second Fc variant antibodies each independently comprise an Fc region amino acid sequence that differs in amino acid sequence from the Fc region of the parent antibody by from 1 amino acid to 5 amino acids, or from 5 amino acids to 10 amino acids. Changes in amino acid sequence are accomplished by one or more of amino acid substitution, deletion, insertion, etc.

In some embodiments, the parent antibody is a wild-type antibody, e.g., a naturally-occurring antibody. In other embodiments, the parent antibody is a synthetic antibody, a recombinant antibody, a chimeric antibody, etc. In some embodiments, an Fc region modified antibody ("Fc variant antibody") is a monoclonal antibody (e.g., an "Fc variant MAb").

In some embodiments, a subject method of making a set of related antibodies comprises one or more of:

a) substituting at least one amino acid residue in the Fc region of a parent antibody, generating an Fc variant antibody, such that the Fc variant antibody exhibits enhanced in vitro ADCC function to at least one Fcγ receptor encoded by an Fcγ receptor gene of a first genotype, compared to the FcγR in vitro ADCC function of the parent antibody, to generate a first Fc variant antibody;

b) substituting at least one amino acid residue in the Fc region of a parent antibody, generating an Fc variant antibody, such that the Fc variant antibody exhibits enhanced in vitro ADCC function to at least one Fcγ receptor encoded by an Fcγ receptor gene of a second genotype, compared to the FcγR in vitro ADCC function of the parent antibody, to generate a second Fc variant antibody;

c) substituting more than one amino acid residue in the Fc region of a parent antibody, generating an Fc variant antibody, such that the Fc variant antibody exhibits enhanced in vitro ADCC function to both Fcγ receptors encoded by the Fcγ receptor genes, compared to the FcγR in vitro ADCC function of the parent antibody;

d) combining the amino acid substitutions of the first and second Fc variant antibodies to generate a third Fc variant antibody such that the third Fc variant antibody exhibit enhanced in vitro ADCC function to both Fcγ receptors encoded by the Fcγ receptor genes, compared to the FcγR in vitro ADCC function of the parent antibody; and e) generating patient Group-specific Fc variant antibodies such that the degree of treatment response to antibody therapy in the patient Groups is increased.

In certain embodiments, first and second Fc variant antibodies have the same antigen specificity, and have the same antigen specificity as the parent antibody. Antibodies that are members of a set of related antibodies include monoclonal antibodies, chimeric antibodies, bi-specific antibodies, recombinant antibodies, synthetic antibodies, semi-synthetic antibodies, tetravalent (multivalent) antibodies, Fc:fusion proteins, and chemically modified intact antibodies.

The parent antibody, the first Fc variant antibody, and the second Fc variant antibody constitute a set of related antibodies. In certain embodiments, the set of related antibodies are therapeutic antibodies suitable for treating an ADCC-treatable disease, condition, or disorder. In some embodiments, a set of related therapeutic antibodies are antibodies that bind a tumor-associated antigen; such a set of related antibodies is useful for treating an individual having a neoplastic disease. In other embodiments, a set of related therapeutic antibodies are antibodies that bind an antigen on an autoreactive immune cell; such a set of related antibodies is useful for treating an individual having an autoimmune disorder. In other embodiments, a set of related therapeutic antibodies are antibodies that bind an antigen on an alloreactive T-cell; such a set of related antibodies is useful for treating allograft rejection. In other embodiments, a set of related therapeutic antibodies are antibodies that bind a viral antigen expressed on the surface of a virus-infected cell; such a set of related antibodies is useful for treating a virus infection. In other embodiments, a set of related therapeutic antibodies are antibodies that bind an antigen expressed on the surface of a parasite; such a set of related antibodies is useful for treating a parasite infection.

Any convenient method of modifying the amino acid sequence of the Fc region can be used. In some embodiments, residues that are proximal to residues that are known to bind or contact an Fc receptor are modified. For example, based on the crystal structure of an Fc portion of an antibody, an amino acid residue that, if substituted, enhances binding to an Fc receptor, is an amino acid residue that is within about 30 Å, within about 15 Å, within about 10 Å, or within about 5 Å, of an amino acid residue that is known to contact an Fc receptor. In other embodiments, residues of the Fc region that are proximal to other Fc residues on a three-dimensional space, if substituted, enhance binding to an Fc receptor. Such examples include interactions between $T^{256}$ and $K^{290}$, and $K^{338}$ and $E^{430}$ (e.g., Shields et al., supra). These residues may be involved in van der Waals contacts, hydrogen bonding, and salt bridge formation.

The Fc fragment including the hinge can be successfully produced as a dimer in E. coli (Kim et al., Eur. J. Immunol. 24:542, 1994). Soluble FcγRIII and FcγRII can also be expressed in E. coli (Sondermann and Jacob, Biol. Chem. 380:717-721, 1999; Sondermann et al., Nature 406:267-273, 2000), and through binding and crystallographic studies it is shown that the Fc fragment binds to FcR domain. Thus, in one embodiment, a) in vitro ADCC is a function of Fc-FcR binding, and b) ADCC-dependent therapeutic response is a function of in vitro ADCC. In another embodiment, in vitro Fc-FcR binding studies and in vitro ADCC assays can be employed to develop Fc variant MAbs specific for patient Groups I-IX as exemplified in this disclosure based on the differences in FcγR polymorphisms.

Fc variant antibodies of interest include antibodies that have at least about 10%, at least about 20%, at least about 30%, at least about 40%, at least about 50%, at least about 60%, at least about 70%, at least about 80%, at least about 90%, or at least about 100%, or 2-fold, increased binding affinity to an Fc receptor and/or enhanced in vitro ADCC activity, compared to the binding affinity of the parent antibody to the Fc receptor and/or in vitro ADCC activity. In some embodiments, Fc variant Abs of interest include antibodies that have at least about 10%, at least about 20%, at least about 30%, at least about 40%, at least about 50%, at least about 60%, at least about 70%, at least about 80%, at least about 90%, or at least about 100%, or 2-fold, increased binding affinity and/or enhanced in vitro ADCC activity to an FcγRIIA comprising $Arg^{131}$, compared to the binding affinity or ADCC activity of the parent antibody to the FcγRIIA comprising $Arg^{131}$. In some embodiments, Fc variant Abs of interest include antibodies that have at least about 10%, at least about 20%, at least about 30%, at least about 40%, at least about 50%, at least about 60%, at least about 70%, at least about 80%, at least about 90%, or at least about 100%, or 2-fold, increased binding affinity and/or enhanced in vitro ADCC activity to an FcγRIIIA comprising $Phe^{158}$, compared to the binding affinity or ADCC activity of the parent antibody to an FcγRIIIA comprising $Phe^{158}$.

Fc variant antibodies of interest will comprise one or more amino acid sequence modifications (substitutions, insertions, deletions, etc.) that provide for enhanced binding affinity and/or enhanced in vitro ADCC activity to an FcγRIIA and/or an FcγRIIIA; and will in some embodiments comprise one or more amino acid substitutions in a hinge region, and/or a CH2 region, and/or a CH3 region. See, e.g., Wines et al., (2000) J. Immunol. 164:5313; Lazar et al., Proc. Natl. Acad. Sci. USA 103:4005-4010, 2006. In some embodiments, Fc variant antibodies of interest will comprise one or more amino acid substitutions in the lower hinge region, e.g., amino acids $L^{234}$-$S^{239}$ (the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody. In some embodiments, Fc variant antibodies of interest will comprise one or more amino acid substitutions in one or more of the following regions: $R^{255}$-$T^{260}$; $D^{265}$-$E^{269}$; $N^{297}$-$T^{299}$; $A^{327}$-$I^{332}$ (See, e.g., FIG. 12-C). In some embodiments, Fc variant antibodies of interest will comprise one or more amino acid substitutions in the CH3 domain, which when substituted, make considerable improvements in FcR binding (e.g., $K^{338}$ and $E^{430}$).

Fc variant antibodies of interest will comprise one or more amino acid substitutions that provide for enhanced binding affinity and/or enhanced in vitro ADCC activity to an FcγRIIA and/or an FcγRIIIA For example, a human IgG1 constant region comprising a T256A or a K290A substitution has enhanced binding affinity to FcγRIIA and FcγRIIIA, compared to wild-type human IgG1. A human IgG1 constant region comprising a E333A, K334A, or A339T substitution has enhanced binding affinity to FcγRIIIA, compared to wild-type human IgG1. Similarly, a human IgG1 constant region comprising the following triple mutations has enhanced binding affinity to FcγRIIIA: S298A, E333A; K334A. See, e.g., Shields et al., *J. Biol. Chem.* 276:6591-6604, 2001 and Presta et al., *Biochem. Soc. Trans.* 30:487-490, 2002.

In some embodiments, an Fc variant antibody exhibits enhanced binding affinity and/or enhanced in vitro ADCC activity between the Fc region of the antibody and an Fcγ receptor, compared to the binding affinity and ADCC activity between the Fc region of a parent antibody and the Fcγ receptor. In some embodiments, a Fc variant antibody exhibits an at least 10%, at least 15%, at least 25%, at least 50%, at least 75%, at least 100% (or two-fold), at least 5-fold, at least 10-fold, at least 50-fold, at least 100-fold, or more, higher affinity and/or enhanced in vitro ADCC activity for an Fpγ receptor than the corresponding parent antibody.

In some embodiments, a method of generating a Fc variant antibody that exhibits enhanced binding affinity and/or enhanced in vitro ADCC activity to an Fc receptor involves modifying a codon in a nucleic acid that comprises a nucleotide sequence that encodes an antibody constant region (including, e.g., hinge region, CH2, and CH3 domains). In some embodiments, a nucleic acid comprising a nucleotide sequence encoding an Fc region is amplified by PCR, using a set of primers that encode all nineteen naturally-occurring amino acid variants at a single residue of the constant region, to generate a set of variant nucleic acids encoding nineteen amino acid substitution variants at the single residue of the constant region. Each of the variants is expressed in an in vitro transcription/translation system, to generate a set of Fc variant antibodies. Each of the Fc variant antibodies is then tested for binding affinity to an Fc receptor. The variants are generated using any known method, including, e.g., the method described in U.S. Pat. No. 6,180,341. Assessing binding to Fc receptors is carried out using any known method, including a method as described in Shields et al. (2001) *J. Biol. Chem.* 276:6591-6604.

In other embodiments, a method of generating a Fc variant antibody that exhibits enhanced binding affinity to an Fc receptor involves generating a set of variant nucleic acids encoding nineteen amino acid substitution variants at the single residue of the constant region, as described above; expressing each of the encoded Fc variant antibodies on the surface of a host cell; and selecting a host cell that expresses a Fc variant antibody that exhibits enhanced binding and/or enhanced in vitro ADCC activity to an Fc receptor. See, e.g., U.S. Patent Publication No. 2003/0036092.

The present disclosure further provides sets of related antibodies, as described above. In many embodiments, the antibodies are isolated.

Antigen-Binding Specificity

A set of related antibodies includes member antibodies that share antigen-binding specificity; and that differ in binding affinity to an FcγR. An antibody that is a member of a set of related antibodies will have an antigen-binding domain; and an Fc domain. Antigen-binding domains (ABD) include ABD specific for an epitope on the surface of a tumor cell; ABD specific for a virally-encoded epitope on the surface of a virus-infected cell; ABD specific for an epitope on the surface of an autoreactive cell; ABD specific for an epitope on the surface of an alloreactive cell; and ABD specific for an epitope expressed on the surface of a eukaryotic parasite, e.g., a helminth. An ABD from any known antibody can be linked to an Fc fragment, e.g., a native Fc fragment, or a variant Fc fragment that exhibits enhanced binding to one or more FcγRs, in generating a set of related antibodies.

Sequences of exemplary Fc fragments (e.g., RITUXAN® (rituximab), REMICADE® (infliximab), ERBITUX® (cetuximab), CAMPATH® (alemtuzumab), HERCEPTIN® (trastuzumab) are shown in FIG. 15.

In some embodiments, antigen binding domains may be obtained from any one of the following antibodies: RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), OKT3® (muromonab-CD3), BEXXAR® (tositumomab), ZEVALIN® (ibritumomab tiuxetan), ENBREL® (etanercept) or AMEVIVE® (alefacept).

Antigen-binding domains will in some embodiments comprise a $V_H$-$C_{H1}$ region and a $V_L$-$C_L$ region. Antigen-binding domains will in some embodiments be a $V_H$ or $V_L$ domains (domain antibodies), Fv, Fab, scFv, F(ab)$_2$ fragments, tetravalent (multivalent) antibodies, Fc:fusion proteins, or engineered Fc:fusion constructs (e.g., SMIPs; Trubion Pharmaceuticals). The antigen-binding domain will in some embodiments have the amino acid sequence of an antigen-binding domain of a naturally-occurring antibody. The antigen-binding domain will in some embodiments be recombinant, synthetic, or semi-synthetic. "Humanized" ABD are also suitable for use; see, e.g., U.S. Pat. No. 6,180,370.

Enhanced Antigen Affinity Improves ADCC

The impact of antigen density and antibody affinity on the efficacy of tumor cell elimination via has been studied extensively. The low-affinity Ep-CAM MAb 17-1A ($K_a$=5×10$^7$ M$^{-1}$) and the high affinity MAb 323/A3 ($K_a$=2×10$^9$ M$^{-1}$) were compared in ADCC experiments against murine and human tumor target cells (Velders et al. supra). The high-affinity MAb mediated ADCC killing of tumor cells with low antigen expression levels. Even at comparable MAb-binding levels, ADCC mediated by the high-affinity MAb was more effective. The kinetics of ADCC was also found to be determined by the level of antigen expression, and by the affinity and concentration of the MAb used (Velders et al. supra).

Additionally, the heterogeneity of a target antigen expression is a common feature of all tumors, and some tumor cells express very low levels of antigen. For example, the CD20 antigen density varies in various NHL types (antigens per cell): normal B-cells, 94,000; mantle cell leukemia, 123,000; pro-lymphocytic leukemia, 129,000; splenic lymphoma, 167,000; hairy cell lymphoma, 312,000; chronic lymphocytic leukemia, 65,000; B-cell (peripheral blood) CLL patients, 9,000; bone marrow and lymph nodes, 4,000 (Manshouri et al. *Blood* 101:2507, 2003).

Affinity improvements in antibodies are primarily accomplished through CDR engineering, and it is a function of association and dissociation rate constants, $k_{on}$, and $k_{off}$ (Schier et al. *J. Mol. Biol.* 263:551, 1996; Wu et al. *Proc. Natl. Acad. Sci. USA* 95:6037, 1998). Thus, improved ADCC in high-affinity antibodies can be due to a) retention of MAbs bound to the antigens for such long periods in a conformationally locked position that facilitates Fc binding to FcγRs, and b) reduced internalization of antibodies as has been shown for anti-Her2/neu antibody variants (for example, McCall et al. *J Immunol.* 166:6112, 2001; Tang et al. High affinity promotes more effective ADCC by anti-HER2/neu monocloncal antibodies, Abstract No: 2538, American Society of Clinical Oncology, 2006 ASCO Annual Meeting).

In one embodiment, affinity improvement through CDR engineering improves the affinity of the IgG Fc region to Fc☐RIIIA and Fc☐RIIA. In another embodiment, affinity improvement through CDR engineering improves the binding of the IgG Fc region to Fc☐RIIIA and Fc☐RIIA. In yet another embodiment, affinity improvement through CDR engineering improves the in vitro ADCC mediated by NK cells and/or macrophages. In another embodiment, affinity improvement through CDR engineering improves the clinical efficacy of an ADCC-mediated antibody therapy.

Cancer Cell Antigens

Examples of antigens that are expressed on the surface of cancer cells and to which an ABD binds include, but are not limited to, $p185^{HER2}$; CD20; CD19; CD21; CD22; CD23; epidermal growth factor (EGF) receptor; vascular endothelial growth factor (VEGF) receptor; CD33; CD52; epithelial cell adhesion molecule (Ep-CAM); carcinoembryonic antigen (CEA); B-cell idiotypes; CD40; CD80; MHC Class-II; CTLA-4; G250 antigen; GD2; and the like. Such antigens are suitable targets for an ADCC-based antibody therapy.

The $p185^{HER2}$ antigen has been described. See, e.g., Coussens, L. et al., *Science* 230:1132-1139 (1985); Yamamoto, T. et al., *Nature* 319:230-234 (1986); King, C. R. et al., *Science* 229:974-976 (1985)). HER2 is also known in the field as c-erbB-2, and sometimes by the name of the rat homolog, neu. Amplification and/or overexpression of HER2 is associated with multiple human malignancies and appears to be integrally involved in progression of 25-30% of human breast and ovarian cancers (Slamon et al., *Science* 235:177-182 (1987), Slamon et al., *Science* 244:707-712 (1989)). Furthermore, the extent of amplification is inversely correlated with the observed median patient survival time (Slamon, supra). Antibodies that bind HER2 are known in the art, and an ABD of any known anti-HER2 antibody can be used. The murine monoclonal antibody known as muMAb4D5 (Fendly et al., *Cancer Res.* 50:1550-1558 (1990)), directed against the extracellular domain (ECD) of $p185^{HER2}$, specifically inhibits the growth of tumor cell lines overexpressing $p185^{HER2}$ in monolayer culture or in soft agar (Hudziak et al., *Mol. Cell. Biol.* 9:1165-1172 (1989); Lupu et al., *Science* 249:1552-1555 (1990)). MuMAb4D5 also has the potential of enhancing tumor cell sensitivity to tumor necrosis factor, an important effector molecule in macrophage-mediated tumor cell cytotoxicity (Hudziak, supra, 1989; Shepard, H. M. and Lewis, G. D. *J. Clinical Immunology* 8:333-395 (1988)). The ABD of muMAb4D5 is useful in the treatment of cancer cells in which $p185^{HER2}$ is overexpressed. The muMAb4D5 antibody is described in PCT application WO 89/06692 published 27 Jul. 1989. This murine antibody was deposited with the ATCC and designated ATCC CRL 10463. A "humanized" version of MAb4D5 is discussed in U.S. Pat. No. 6,800,738.

Antibodies to CD20 are known in the art and include Rituximab (as discussed above). Antibodies to CD52 include, e.g., Alemtuzumab (Campath-1H) (see, e.g., U.S. Pat. No. 5,545,403). Antibodies to CD33 include, e.g., gemtuzumab (Myelotarg); humanized M195 (Caron et al., (1994) *Blood* 83:1760-1768; and Co et al., (1992) *J. Immunol.* 148:1149). Antibodies to EGF receptor include, e.g., cetuximab (Erbitux); and panitumumab (Abgenix/Immunex). Antibodies to GD2 (expressed on neuroblastoma cells) include, e.g., Ch14.18 (NCI). Antibodies to G250 antigen (expressed on renal cancer cells) include, e.g., Rencarex (WX-9250; Wilex). Antibodies to MHC class-II (expressed on non-Hodgkins lymphoma cells) include, e.g., Remitogen (Hu1D10; Protein Design Labs).

Autoreactive Immune Cell Antigens

Antigens expressed on the surface of autoreactive immune cells that are suitable as targets of an ADCC-based antibody therapy include, but are not limited to, CD3.

Antigens Expressed on Alloreactive T-Cells

Antigens on alloreactive T-cells that are suitable as targets of an ADCC-based antibody therapy include, but are not limited to, CD3, CD2, CD4, CD5, CD6, CD8, CD28, and CD44.

Microbial Antigens

Viral antigens that are suitable as targets of an ADCC-based antibody therapy include virus-encoded antigens expressed on the surface of a virus-infected cell. Viral antigens are from any of a variety of DNA and RNA viruses. Although HCV is primarily a hepatotropic virus, HCV infection is frequently associated with mixed cryoglobulinemia, non-Hodgkin's B-cell lymphoma, and Sjögren's syndrome, all of which involve B-cell proliferation (Selva-O'Callaghan et. al., *Arthritis Rheum.* 42:2489, 1999), suggesting that HCV may infect B-cells or affect B-cell functions in natural infection. Minus-strand HCV RNA has been detected by reverse transcriptase PCR in peripheral lymphocytes, bone marrow, lymph nodes, and central nervous system of some HCV patients (Radkowski et. al., *J. Virol.* 76: 600, 2002).

Parasitic antigens that are suitable targets for ADCC-based antibody therapy include antigens expressed on the surface of a parasite that is the etiologic agent of a parasitic disorder. Bacterial antigens that are suitable targets for ADCC-based antibody therapy include antigens expressed on the surface of a bacterium that is the etiologic agent of a bacterial infection.

Preparation of Antibodies

Variant antibodies are produced by modifying the nucleic acid of a parent antibody, inserting the modified nucleic acid into an appropriate cloning vector and expressing the modified nucleic acid to produce variant antibodies. Representative protocols are described below:

1. Making Variant Antibody Nucleic Acid

Variant antibodies will comprise one or more amino acid sequence modifications (substitutions, insertions, deletions, etc.) relative to a parent antibody sequence that provide for enhanced binding affinity and/or enhanced in vitro ADCC activity to an FcγRIIA and/or an FcγRIIIA.

In some embodiments, an Fc variant antibodies will comprise one or more amino acid substitutions in a hinge region, and/or a CH2 region, and/or a CH3 region (See, e.g., Wines et al., (2000) J. Immunol. 164:5313; Lazar et al. (2006) Proc. Natl. Acad. Sci. USA 103:4005-4010). In other embodiments, Fc variant antibodies of interest will comprise one or more amino acid substitutions in the lower hinge region, e.g., amino acids $L^{234}$-$S^{239}$ (the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody. In yet further embodiments, Fc variant antibodies of interest will comprise one or more amino acid substitutions in one or more of the following regions: $R^{255}$-$T^{260}$; $D^{265}$-$E^{269}$; $N^{297}$-$T^{299}$; $A^{327}$-$I^{332}$ (See, e.g., FIG. 12-C). In some embodiments, Fc variant antibodies of interest will comprise one or more amino acid substitutions in the CH3 domain, which when substituted, make considerable improvements in FcR binding (e.g., $K^{338}$ and $E^{430}$).

Fc variant antibodies of interest will comprise one or more amino acid substitutions that provide for enhanced binding affinity and/or enhanced in vitro ADCC activity to an FcγRIIA and/or an FcγRIIIA. For example, a human IgG1 constant region comprising a T256A or a K290A substitution has enhanced binding affinity to FcγRIIA and FcγRIIIA, compared to wild-type human IgG1. A human IgG1 constant region comprising a E333A, K334A, or A339T substitution has enhanced binding affinity to FcγRIIIA, compared to wild-type human IgG1. Similarly, a human IgG1 constant region comprising the following triple mutations has enhanced binding affinity to FcγRIIIA: S298A, E333A; K334A (See, e.g., Shields et al. (2001) J. Biol. Chem. 276:6591-6604; and Presta et al. (2002) Biochem. Soc. Trans. 30:487-490).

In some embodiments, an Fc variant antibody exhibits enhanced binding affinity and/or enhanced in vitro ADCC activity between the Fc region of the antibody and an Fcγ receptor, compared to the binding affinity and ADCC activity between the Fc region of a parent antibody and the Fcγ receptor. In some embodiments, a Fc variant antibody exhibits an at least 10%, at least 15%, at least 25%, at least 50%, at least 75%, at least 100% (or two-fold), at least 5-fold, at least 10-fold, at least 50-fold, at least 100-fold, or more, higher affinity and/or enhanced in vitro ADCC activity for an Fcγ receptor than the corresponding parent antibody.

In some embodiments, a method of generating a Fc variant antibody that exhibits enhanced binding affinity and/or enhanced in vitro ADCC activity to an Fc receptor involves modifying a codon in a nucleic acid that comprises a nucleotide sequence that encodes an antibody constant region (including, e.g., hinge region, CH2, and CH3 domains). In some embodiments, a nucleic acid comprising a nucleotide sequence encoding an Fc region is amplified by PCR, using a set of primers that encode all nineteen naturally-occurring amino acid variants at a single residue of the constant region, to generate a set of variant nucleic acids encoding nineteen amino acid substitution variants at the single residue of the constant region.

The antibody variants are generated using any known method, including, e.g., the method described in U.S. Pat. No. 6,180,341.

In other embodiments, a method of generating a Fc variant antibody that exhibits enhanced binding affinity to an Fc receptor involves generating a set of variant nucleic acids encoding nineteen amino acid substitution variants at the single residue of the constant region, as described above; expressing each of the encoded Fc variant antibodies on the surface of a host cell; and selecting a host cell that expresses a Fc variant antibody that exhibits enhanced binding and/or enhanced in vitro ADCC activity to an Fc receptor (See, e.g., U.S. Patent Publication No. 2003/0036092).

In other embodiments, antibody variants may comprise one or more amino acid substitutions in a complementarity determining region (CDR). Such modifications may be generated by any of the methods describe above concerning Fc variants.

In designing amino acid sequence antibody variants, the location of the mutation site and the nature of the mutation will depend on the target antibody characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1-3.

A useful method for identification of certain residues or regions of the antibody that are preferred locations for mutagenesis is called "alanine scanning mutagenesis" as described by Cunningham and Wells (Science, 244: 1081-1085 (1989)). Here, a residue or Group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed antibody variants are screened for the optimal combination of desired activity.

There are two principal variables in the construction of amino acid sequence variants: the location of the mutation site and the nature of the mutation. In general, the location and nature of the mutation chosen will depend upon the antibody characteristic to be modified.

Amino acid sequence deletions of antibodies are generally not preferred, as maintaining the generally configuration of an antibody is believed to be necessary for its activity. Any deletions will be selected so as to preserve the structure of the antibody.

Amino acid sequence insertions include amino- and/or carboxyl-terminal fusions ranging in length from one residue to polypeptides containing a hundred or more residues, as well as intra-sequence insertions of single or multiple amino acid residues. Intrasequence insertions (i.e., insertions within the antibody sequence) may range generally from about 1 to 10 residues, more preferably 1 to 5, most preferably 1 to 3. Examples of terminal insertions include the antibody with an N-terminal methionyl residue, an artifact of the direct expression of target polypeptide in bacterial recombinant cell culture, and fusion of a heterologous N-terminal signal sequence to the N-terminus of the target polypeptide molecule to facilitate the secretion of the mature target polypeptide from recombinant host cells. Such signal sequences generally will be obtained from, and thus homologous to, the intended host cell species. Suitable sequences include STII or Ipp for *E. coli*, alpha factor for yeast, and viral signals such as herpes gD for mammalian cells.

Another group of variants are amino acid substitution variants. These variants have at least one amino acid residue in the antibody molecule removed and a different residue inserted in its place. The sites of greatest interest for substitutional mutagenesis include sites identified as the active site(s) of the antibody, and sites where the amino acids found in the antibody from various species are substantially different in terms of side-chain bulk, charge, and/or hydrophobicity. Other sites for substitution are described infra, considering the effect of the substitution of the antigen binding, affinity and other characteristics of a particular target antibody.

Other sites of interest are those in which particular residues of the antibody obtained from various species are identical. These positions may be important for the biological activity of the antibody. These sites, especially those falling within a sequence of at least three other identically conserved sites, are substituted in a relatively conservative manner. If such substitutions result in a change in biological activity, then other changes are introduced and the products screened until the desired effect is obtained.

Substantial modifications in function or immunological identity of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into Groups based on common side chain properties:

hydrophobic: norleucine, met, ala, val, leu, ile;
neutral hydrophilic: cys, ser, thr;
acidic: asp, glu;
basic: asn, gin, his, lys, arg;
residues that influence chain orientation: gly, pro; and
aromatic: trp, tyr, phe.

Non-conservative substitutions will entail exchanging a member of one of these classes for another. Such substituted residues may be introduced into regions of the antibody that are homologous with other antibodies of the same class or subclass, or, more preferably, into the non-homologous regions of the molecule.

Any cysteine residues not involved in maintaining the proper conformation of the antibody also may be substituted, generally with serine, to improve the oxidative stability of the molecule and prevent aberrant crosslinking.

DNA encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the target polypeptide. A particularly preferred method of gene conversion mutagenesis is described below in Example 1. These techniques may utilized antibody nucleic acid (DNA or RNA), or nucleic acid complementary to the antibody nucleic acid. Oligonucleotide-mediated mutagenesis is a preferred method for preparing substitution, deletion, and insertion variants of antibody DNA. This technique is well known in the art as described by Adelman et al. (1983) DNA, 2: 183. Briefly, the antibody DNA is altered by hybridizing an oligonucleotide encoding the desired mutation to a DNA template, where the template is the single-stranded form of a plasmid or bacteriophage containing the unaltered or native DNA sequence of the target polypeptide. After hybridization, a DNA polymerase is used to synthesize an entire second complementary strand of the template that will thus incorporate the oligonucleotide primer, and will code for the selected alteration in the target polypeptide DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (Proc. Natl. Acad. Sci. USA, 75: 5765 (1978)).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the antibody, and the other strand (the original template) encodes the native, unaltered sequence of the antibody. This heteroduplex molecule is then transformed into a suitable host cell, usually a prokaryote such as E. coli JM 101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex.

Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101, as described above.

DNA encoding antibody variants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant antibody. The first round is as described for the single antibody mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid antibody variants. While the following discussion refers to DNA, it is understood that the technique also finds application with RNA. The PCR technique generally refers to the following procedure (See, e.g., Erlich, supra, the chapter by R. Higuchi, p. 61-70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide tri-phosphates and is included in the GeneAmp® kits (obtained from Perkin-Elmer Cetus, Norwalk, Conn. and Emeryville, Calif.), and 25 pmole of each oligonucleotide primer, to a final volume of 50 μl. The reaction mixture is overlayed with 35 μl mineral oil. The reaction is denatured for 5 minutes at 100° C., placed briefly on ice, and then 1 μl *Thermus aquaticus* (Taq) DNA polymerase (5 units/μl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows: 2 min. at 55° C., then 30 sec. at 72° C., then 19 cycles of the following: 30 sec. at 94° C., 30 sec. at 55° C., and 30 sec. at 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (Gene, 34: 315 (1985)). The starting material is the plasmid (or other vector) comprising the antibody DNA to be mutated. The codon(s) in the antibody DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the target polypeptide DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated antibody DNA sequence.

2. Insertion of DNA into a Cloning Vehicle

The cDNA or genomic DNA encoding the antibody is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(a) Signal Sequence Component

In general, the signal sequence may be a component of the vector, or it may be a part of antibody DNA that is inserted into the vector.

The therapeutic antibody may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the antibody DNA that is inserted into the vector. Included within the scope of this disclosure are antibody with any native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native target polypeptide signal sequence may be substituted by the yeast invertase, alpha factor, or acid phosphatase leaders. In mammalian cell expression the native signal sequence is satisfactory, although other mammalian signal sequences may be suitable.

(b) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is, transfected into yeast or mammalian cells for expression even though it is not capable of replicating independently of the host cell chromosome.

DNA may also be amplified by insertion into the host genome. This is readily accomplished using *Bacillus* as a host, for example, by including in the vector a DNA sequence that is complementary to a sequence found in *Bacillus* genomic DNA. Transfection of *Bacillus* with this vector results in homologous recombination with the genome and insertion of the antibody DNA. However, the recovery of genomic DNA encoding the antibody is more complex than that of an exogenously replicated vector because restriction enzyme digestion is required to excise the antibody DNA.

(c) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al. (1982) J. Molec. Appl. Genet., 1: 327), mycophenolic acid (Mulligan et al. (1980) Science, 209: 1422) or hygromycin (Sugden et al. (1985) Mol. Cell. Biol., 5: 410-413). The three examples given above employ bacterial genes under eukaryotic control to convey resistance to the appropriate drug G418 or neomycin (geneticin), xgpt (mycophenolic acid), or hygromycin, respectively. Another example of suitable selectable markers for mammalian cells are those that enable the identification of cells competent to take up the antibody nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes antibody. Amplification is the process by which genes in greater demand for the production of a protein critical for growth are reiterated in tandem within the chromosomes of successive generations of recombinant cells. Increased quantities of the antibody are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin (1980) Proc. Natl. Acad. Sci. USA, 77: 4216. The transformed cells are then exposed to increased levels of methotrexate. This leads to the synthesis of multiple copies of the DHFR gene, and, concomitantly, multiple copies of other DNA comprising the expression vectors, such as the DNA encoding the antibody.

This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the antibody, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418 (See, e.g., U.S. Pat. No. 4,965,199).

A suitable selection gene for use in yeast is the trp1 gene present in the yeast plasmid YRp7 (Stinchcomb et al. (1979) Nature, 282: 39; Kingsman et al. (1979) Gene, 7: 141; or Tschemper et al. (1980) Gene, 10: 157). The trp1 gene provides a selection marker for a mutant strain of yeast lacking the ability to grow in tryptophan, for example, ATCC No. 44076 or PEP4-1 (Jones (1977) Genetics, 85: 12). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(d) Promoter Component

Expression and cloning vectors usually contain a promoter that is recognized by the host organism and is operably linked to the antibody nucleic acid. Promoters are untranslated sequences located upstream (5') to the start codon of a structural gene (generally within about 100 to 1000 bp) that control the transcription and translation of a particular nucleic acid sequence, such as that encoding the antibody, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the target polypeptide by removing the promoter from the source DNA by restriction enzyme digestion and inserting the isolated promoter sequence into the vector. Both the native antibody promoter sequence and many heterologous promoters may be used to direct amplification and/or expression of the antibody DNA. However, heterologous promoters are preferred, as they generally permit greater transcription and higher yields of expressed antibody as compared to the native antibody promoter.

Promoters suitable for use with prokaryotic hosts include the β-lactamase and lactose promoter systems (Chang et al. (1978) Nature, 275: 615; and Goeddel et al. (1979) Nature, 281: 544), alkaline phosphatase, a tryptophan (trp) promoter system (Goeddel (1980) Nucleic Acids Res., 8: 4057 and EP 36,776) and hybrid promoters such as the tac promoter (deBoer et al. (1983) Proc. Natl. Acad. Sci. USA, 80: 21-25).

However, other known bacterial promoters are suitable. Their nucleotide sequences have been published, thereby enabling a skilled worker operably to ligate them to DNA encoding the target polypeptide (Siebenlist et al. (1980) Cell, 20: 269) using linkers or adaptors to supply any required restriction sites. Promoters for use in bacterial systems also generally will contain a Shine-Dalgarno (S.D.) sequence operably linked to the DNA encoding the target polypeptide.

Suitable promoting sequences for use with yeast hosts include the promoters for 3-phosphoglycerate kinase (Hitzeman et al. (1980) J. Biol. Chem., 255: 2073) or other glycolytic enzymes (Hess et al, (1968) J. Adv. Enzyme Reg., 7: 149; and Holland (1978) Biochemistry, 17:4900), such asenolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, met allothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Antibody transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the antibody sequence, provided such promoters are compatible with the host cell systems.

The early and late promoters of the SV40 virus are conveniently obtained as an SV40 restriction fragment that also contains the SV40 viral origin of replication. Fiers et al., Nature, 273:113 (1978); Mulligan and Berg, Science, 209: 1422-1427 (1980); Pavlakis et al., Proc. Natl. Acad. Sci. USA, 78: 7398-7402 (1981). The immediate early promoter of the human cytomegalovirus is conveniently obtained as a HindIII E restriction fragment. Greenaway et al., Gene, 18: 355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See, e.g., Gray et al., Nature, 295: 503-508 (1982) on expressing cDNA encoding immune interferon in monkey cells; Reyes et al., Nature, 297: 598-601 (1982) on expression of human β-interferon cDNA in mouse cells under the control of a thymidine kinase promoter from herpes simplex virus, Canaani and Berg, Proc. Natl. Acad. Sci. USA, 79: 5166-5170 (1982) on expression of the human interferon β1 gene in cultured mouse and rabbit cells, and Gorman et al., Proc. Natl. Acad. Sci. USA, 79: 6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(e) Enhancer Element Component

Transcription of DNA encoding the antibody of this disclosure by higher eukaryotes is often increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins et al., Proc. Natl. Acad. Sci. USA, 78: 993 [1981]) and 3' (Lusky et al., Mol. Cell. Bio., 3: 1108 [1983]) to the transcription unit, within an intron (Banerji et al., Cell, 33: 729 [1983]) as well as within the coding sequence itself (Osborne et al., Mol. Cell. Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See, e.g., Yaniv, Nature, 297: 17-18 (1982) on enhancing elements for activation of eukaryotic promoters. The enhancer may be spliced into the vector at a position 5' or 3' to the antibody DNA, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNA or cDNAs. These regions contain nucleotide segments transcribed as polyadenylated fragments in the untranslated portion of the mRNA encoding the target polypeptide. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform E. coli K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., Nucleic Acids Res., 9: 309 (1981) or by the method of Maxam et al., Methods in Enzymology. 65: 499 (1980).

Particularly useful in the practice of this disclosure are expression vectors that provide for the transient expression in mammalian cells of DNA encoding the antibody. In general, transient expression involves the use of an expression vector that is able to replicate efficiently in a host cell, such that the host cell accumulates many copies of the expression vector and, in turn, synthesizes high levels of a desired antibody encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the disclosure for purposes of identifying analogs and variants of the antibody that have antibody-like activity.

Other methods, vectors, and host cells suitable for adaptation to the synthesis of the target polypeptide in recombinant vertebrate cell culture are described in Gething et al., Nature, 293: 620-625 [1981]; Mantei et al., Nature, 281:40-46 [1979]; Levinson et al.; EP 117,060; and EP 117,058. A particularly useful plasmid for mammalian cell culture expression of the antibody is pRK5 (EP pub. no. 307,247) or pSVI6B. Selection and 3. Transformation of Host Cells Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis, Pseudomonas* species such as *P. aeruginosa, Salmonella typhimurium*, or *Serratia marcescens*. One preferred *E. coli* cloning host is *E. coli* 294 (ATCC 31,446), although other strains such as *E. coli* B, *E. coli* .chi.1776 (ATCC 31,537), and *E. coli* W3110 (ATCC 27,325) are suitable.

These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for target polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, Nature, 290: 140 (1981); EP 139,383 published May 2, 1985], *Kluyveromyces* hosts (U.S. Pat. No. 4,943,529) such as, e.g., *K. lactis* [Louvencourt et al., J. Bacteriol., 737 (1983)], *K. fragilis, K. bulgaricus, K. thermotolerans*, and *K. marxianus, yarrowia* [EP 402,226], *Pichia pastoris* [EP 183, 070; Sreekrishna et al., J. Basic Microbiol., 28: 265-278 (1988)], *Candida, Trichoderma reesei* [EP 244,234], *Neurospora crassa* [Case et al., Proc. Natl. Acad. Sci. USA, 76: 5259-5263 (1979)], and filamentous fungi such as, e.g., *Neurospora, Penicillium, Tolypocladium* [WO 91/00357 published Jan. 10, 1991], and *Aspergillus* hosts such as *A. nidulans* [Ballance et al., Biochem. Biophys. Res. Commun. 112: 284-289 (1983); Tilburn et al., Gene, 26: 205-221 (1983); Yelton et al., Proc. Natl. Acad. Sci. USA, 81: 1470-1474 (1984)] and *A. niger* [Kelly and Hynes, EMBO J., 4:475-479 (1985)].

Suitable host cells for the expression of glycosylated target polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., Bio/Technology, 6: 47-55 (1988); Miller et al., in Genetic Engineering, Setlow, J. K. et al., eds., Vol. 8 (Plenum Publishing, 1986), pp. 277-279; and Maeda et al., Nature, 315: 592-594 (1985). A variety of such viral strains are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the antibody DNA. During incubation of the plant cell culture with *A. tumefaciens*, the DNA encoding antibody is transferred to the plant cell host such that it is transfected, and will, under appropriate conditions, express the antibody DNA. In addition, regulatory and signal sequences compatible with plant cells are available, such as the nopaline synthase promoter and polyadenylation signal sequences. Depicker et al., J. Mol. Appl. Gen., 1: 561 (1982). In addition, DNA segments isolated from the upstream region of the T-DNA 780 gene are capable of activating or increasing transcription levels of plant-expressible genes in recombinant DNA-containing plant tissue. See, e.g., EP 321,196 published Jun. 21, 1989.

However, interest has been greatest in vertebrate cells, and propagation of vertebrate cells in culture (tissue culture) has become a routine procedure in recent years [Tissue Culture, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36: 59 [1977]); baby hamster kidney cells (BHK, ATCC CCL 10); Chinese hamster ovary cells/–DHFR (CHO, Urlaub and Chasin, Proc. Natl. Acad. Sci. USA, 77: 4216 [1980]); mouse sertoli cells (TM4, Mather, Biol. Reprod., 23: 243-251[1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44-68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this disclosure and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., Gene, 23: 315 (1983) and WO 89/05859 published Jun. 29, 1989. For mammalian cells without such cell walls, the calcium phosphate precipitation method described in sections 16.30-16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., J. Bact., 130: 946 (1977) and Hsiao et al., Proc. Natl. Acad. Sci. (USA), 76: 3829 (1979). However, other methods for introducing DNA into cells such as by nuclear injection, electroporation, or protoplast fusion may also be used. Culturing the Host Cells Prokaryotic cells used to produce the target polypeptide of this disclosure are cultured in suitable media as described generally in Sambrook et al., supra.

The mammalian host cells used to produce the target polypeptide of this disclosure may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, Meth. Enz., 58: 44 (1979), Barnes and Sato, Anal. Biochem., 102: 255 (1980), U.S. Pat. No. 4,767,704; 4,657,866; 4,927,762; or 4,560,655; WO 90/03430; WO 87/00195; U.S. Pat. Re. No. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the antibody of this disclosure may be produced by homologous recombination, or with recombinant production methods utilizing control elements introduced into cells already containing DNA encoding the antibody currently in use in the field. For example, a powerful promoter/enhancer element, a suppressor, or an exogenous transcription modulatory element is inserted in the genome of the intended host cell in proximity and orientation sufficient to influence the transcription of DNA encoding the desired antibody. The control element does not encode the antibody of this disclosure, but the DNA is present in the host cell genome. One next screens for cells making the antibody of this disclosure, or increased or decreased levels of expression, as desired.

Enhancement of Antibody Effector Functions

Methods are provided for using a subject's FcγRIIA and/or FcγRIIIA genotype to select a specific Fc nucleotide sequence associated with optimal effector function for an antibody therapy.

It is contemplated that the Fc nucleotide sequence from an antibody, including, for example, a variant antibody with one or more optimal effector functions for a particular FcγRIIA and FcγRIIIA genotype can be used to optimize one or more effector functions of other antibodies used to treat the same or other subjects with the FcγRIIA and FcγRIIIA genotype.

In a preferred embodiment, the effector function is ADCC. In other embodiments, the effector function is selected from the Group consisting of: phagocytosis, opsonization, opsonophagocytosis, Clq binding, and complement dependent cell mediated cytotoxicity (CDC).

Generally, methods are provided for enhancing one or more effector functions of an antibody used to treat a subject having an ADCC-treatable disease or disorder, comprising: a) genotyping the subject for an FcγRIIA polymorphism and a FcγRIIIA polymorphism; b) classifying the subject into one of more than three categories of ADCC activity for the antibody based on their FcγRIIA polymorphism and FcγRIIIA polymorphism; and c) selecting an Fc nucleotide sequence that has at least one optimized effector function for the FcγRIIA polymorphism and FcγRIIIA polymorphism, wherein at least one effector function of the antibody is enhanced by using the optimized Fc nucleotide sequence.

Fc cassettes are optimized for each of the nine distinct FcγRIIA and FcγRIIIA genotypes, including: $V/V^{158}$, $H/H^{131}$ (Group-I); $V/F^{158}$, $H/H^{131}$ (Group-II); $F/F^{158}$, $H/H^{131}$ (Group-III); $V/V^{158}$, $H/R^{131}$ (Group-IV); $V/F^{158}$, $H/R^{131}$ (Group-V); $F/F^{158}$, $H/R^{131}$ (Group-VI); $V/V^{158}$, $R/R^{131}$ (Group-VII); $V/F^{158}$, $R/R^{131}$ (Group-VIII); and $F/F^{158}$, $R/R^{131}$ (Group-IX) as previously described in the above methods.

Antibody effector functions, such as ADCC, may be optimized for a particular FcγRIIA and FcγRIIIA genotype by altering the nucleotide sequence of the Fc portion of the antibody, to a Fc nucleotide sequence associated with optimal effector functions for the genotype. The nucleotide sequence of the Fc region of an antibody is engineered by techniques commonly known in the art to derive the same nucleotide sequence of Fc that has optimized ADCC activity for a subject with a particular FcγRIIA and FcγRIIIA genotype.

In other embodiments, the ADCC activity of an antibody used to treat a subject with a particular FcγRIIA and FcγRIIIA genotype can be optimized by fusing a Fc nucleotide sequence from another antibody molecule which has optimized effector functions for the given genotype to the antibody.

Therapeutic antibodies used to treat a particular γRIIA ($H/R^{131}$) FcγRIIIA ($V/F^{158}$) genotype may be modified to exhibit optimal ADCC activity. For instance the therapeutic antibody RITUXAN™ has optimal ADCC activity for subjects exhibiting a $V/V^{158}$, $H/H^{131}$ genotype. Hence, the Fc nucleotide sequence of RITUXAN™ may be used to optimize ADCC activity of other antibodies used to treat subjects exhibiting a $V/V^{158}$, $H/H^{131}$ genotype. For instance, the Fc nucleotide sequence of RITUXAN™ may be used to in place of the Fc nucleotide sequence present in ZENAPAX® to optimize ADCC activity in subjects exhibiting a $V/V^{158}$, $H/H^{131}$ genotype.

Examples of other therapeutic antibodies, variable regions of an antibody, or Fc variant antibodies that can be engineered to have enhanced ADCC activity for a particular FcγRIIa and FcγRIIIa genotype, include but are not limited to: RITUXAN® (rituximab), CAMPATH® (alemtuzumab), ZENAPAX® (daclizumab), HERCEPTIN® (trastuzumab), XOLAIR® (omalizumab), RAPTIVA® (efalizumab), AVASTIN® (bevacizumab), REMICADE® (infliximab), HUMIRA® (adalimumab), ERBITUX® (cetuximab), SIMULECT® (basiliximab), SYNAGIS® (palivizumab), VECTIBIX® (panitumumab), TYSABRI® (natalizumab), MYLOTARG® (gemtuzumab ozogamicin), REOPRO® (abciximab), OKT3® (muromonab-CD3), BEXXAR® (tositumomab), or ZEVALIN® (ibritumomab tiuxetan).

Optimized fusion antibodies can be produced by standard recombinant DNA techniques or by protein synthetic techniques, e.g., by use of a peptide synthesizer. For example, a nucleic acid molecule encoding an optimized antibody fusion can be synthesized by conventional techniques including automated DNA synthesizers.

Alternatively, PCR amplification of gene fragments (i.e. the optimized Fc and antigen binding domain) can be carried out using anchor primers which give rise to complementary overhangs between two consecutive gene fragments which can subsequently be annealed and reamplified to generate a chimeric gene sequence (See, e.g., Current Protocols in Molecular Biology, Ausubel et al., eds., John Wiley & Sons, 1992).

Moreover, a nucleic acid encoding an antigen binding domain can be cloned into an expression vector containing an genotype optimized Fc region such that the antigen binding domain is linked in-frame to the optimized Fc region.

Methods for fusing or conjugating antigen binding domains to a genotype optimized Fc are known in the art (See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; International Publication Nos. WO 91/06570, WO 96/04388, WO 96/22024, WO 97/34631, and WO 99/04813; Ashkenazi et al., 1991, Proc. Natl. Acad. Sci. USA 88: 10535-10539; Traunecker et al., 1988, Nature, 331:84-86; Zheng et al., 1.995, J. Immunol. 154:5590-5600; and Vil et al., 1992, Proc. Natl. Acad. Sci. USA 89:11337-11341).

The nucleotide sequences encoding a antigen binding domain and an Fc domain may be obtained from any information available to those of skill in the art (i.e., from Genbank, the literature, or by routine cloning) (See, e.g., Xiong et al., Science, 12; 294(554 1): 339-45 (2001)). The nucleotide sequence coding for an antibody fusion protein can be inserted into an appropriate expression vector, i.e., a vector that contains the necessary elements for the transcription and translation of the inserted protein-coding sequence. A variety of host-vector systems may be utilized in the present disclosure to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Functional Assays for Antibodies

Antibodies, including, for example, variant antibodies may be characterized in a variety of ways. For example, antibody variants may be assayed for the ability to specifically bind to a ligand, (e.g., FcγRIIIA, FcγRIIB, Clq). Such an assay may be performed in solution (e.g., Houghten, Bio/Techniques, 13:412-421, 1992), on beads (Lam, Nature, 354:82-84, 1991, on chips (Fodor, Nature, 364:555-556, 1993), on bacteria (U.S. Pat. No. 5,223,409), 011 plasmids (Cull et al., Proc. Natl. Acad. Sd. USA, 89:1865-1869, 1992) or on phage (Scott and Smith, Science, 249:386-390, 1990; Devlin, Science, 249:404-406, 1990; Cwirla et al., Proc. Natl. Acad. Sci. USA, 87:6378-6382, 1990; and Felici, J. Mol. Biol., 222:301-310, 1991). Molecules that have been identified to specifically bind to a ligand, (e.g., FcγRIIIA, FcγRIIB, Clq or to an antigen) can then be assayed for their affinity for the ligand.

Antibody variants may be assayed for specific binding to a molecule such as an antigen (e.g., cancer antigen and cross-reactivity with other antigens) or a ligand (e.g., FcγR) by any method known in the art, Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (See, e.g., Ausubel et al., eds, 1994, Current Protocols in Molecular Biology, Vol. 1, John Wiley & Sons, Inc., New York).

The binding affinity of the antibody variants to a molecule such as an antigen or a ligand, (e.g., FcγR) and the off-rate of the interaction can be determined by competitive binding assays. One example of a competitive binding assay is a radioimmunoassay comprising the incubation of labeled ligand, such as FcγR (e.g., 3H or 1251) with a molecule of interest (e.g., antibody variants) in the presence of increasing amounts of unlabeled ligand, such as FcγR, and the detection of the molecule bound to the labeled ligand. The affinity of the molecule of the present disclosure for the ligand and the binding off-rates can be determined from the saturation data by scatchard analysis.

The kinetic parameters of an antibody variant may also be determined using any surface plasmon resonance (SPR) based assays known in the art (e.g., BIAcore kinetic analysis). For a review of SPR-based technology, See, e.g., Mullet et al., 2000, Methods 22: 77-9 1; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61.

Additionally, any of the SPR instruments and SPR based methods for measuring protein-protein interactions described in U.S. Pat. Nos. 6,373,577; 6,259,286 5,322,798; 5,341,215; 6,268,125 are contemplated in the methods of the disclosure.

Fluorescence activated cell sorting (FACS), using any of the techniques known to those skilled in the art, can be used for characterizing the binding of antibody variants to a molecule expressed on the cell surface (e.g., FcγRIIA, FcγRIIIA) Flow sorters are capable of rapidly examining a large number of individual cells that contain library inserts (e.g., 10-100 million cells per hour) (Shapiro et al, Practical Flow cytometry, 1995). Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477. Other known flow cytometers are the FACS Vantage™ system manufactured by Becton Dickinson and Company, and the COPAS™ system manufactured by Union Biometrica.

The antibody variants can be characterized by their ability to mediate FcγR-mediated effector cell function. Examples of effector cell functions that can be assayed include, but are not limited to, antibody-dependent cell mediated cytotoxicity (ADCC), phagocytosis, opsonization, opsonophagocytosis, Clq binding, and complement dependent cell mediated cytotoxicity (CDC).

Any cell-based or cell free assay known to those skilled in the art for determining effector cell function activity can be used (For effector cell assays, See, e.g., Perussia et al., 2000, Methods Mol. Biol. 121: 179-92; Baggiolini et al., 1998 Experientia, 44(10): 841-8; Lehmann et al., 2000 J. Immunol, Methods, 243(1-2): 229-42; Brown E J. 1994, Methods Cell Biol., 45: 147-64; Munn et al., 1990 J. Exp. Med., 172: 231-237, Abdul-Majid et al., 2002 Scand. J. Immunol. 55: 70-81; Ding et al., 1998, Immunity 8:403-411).

For example, the antibody variants can be assayed for FcγR-mediated ADCC activity in effector cells, (e.g., natural killer cells) using any of the standard methods known to those skilled in the art (See e.g., Perussia et al., 2000, Methods Mol. Biol.).

An exemplary assay for determining ADCC activity of the molecules of the disclosure is based on a $^{51}$Cr release assay comprising of: labeling target cells with $Na_2CrO_4$ (this cell-membrane permeable molecule is commonly used for labeling since it binds cytoplasmic proteins and although spontaneously released from the cells with slow kinetics, it is released massively following target cell necrosis); osponizing the target cells with the antibody variants of the disclosure; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the disclosure can then be determined, for example using the following formula: % lysis(experimental cpm-target leak cpm)/(detergent lysis cpm-target leak cpm)×100%. Alternatively, % lysis=(ADCC-AICC)/(maximum release-spontaneous release). Specific lysis can be calculated using the formula: specific lysis % lysis with the molecules of the disclosure –% lysis in the absence of the molecules of the disclosure. A graph can be generated by varying either the target: effector cell ratio or antibody concentration.

Methods to characterize the ability of the antibody variants to bind Clq and mediate complement dependent cytotoxicity (CDC) are well known in the art. For example, to determine Clq binding, a Clq binding ELISA may be performed. An exemplary assay may comprise the following: assay plates may be coated overnight at 4° C. with polypeptide variant or starting polypeptide (control) in coating buffer. The plates may be washed and blocked. Following washing, an aliquot of human Clq may be added to each well and incubated for 2 hrs at room temperature. Following a further wash, 100 μL of a sheep anti-complement Clq peroxidase conjugated antibody may be added to each well and incubated for 1 hour at room temperature. The plate may again be washed with wash buffer and 100 μl of substrate buffer containing OPD (0-phenylenediamine dihydrochloride (Sigma)) may be added to each well. The oxidation reaction, observed by the appearance of a yellow color, may be allowed to proceed for 30 minutes and stopped by the addition of 100 μl of 4.5 $NH_2SO_4$. The absorbance may then read at (492-405) nm. Specific methods are also disclosed in the section entitled "Examples," infra.

To assess complement activation, a complement dependent cytotoxicity (CDC) assay may be performed, (e.g. as described in Gazzano-Santoro et al., 1996, J. Immunol. Methods 202:163). Briefly, various concentrations of antibody variant and human complement may be diluted with buffer. Cells which express the antigen to which the Fc variant binds may be diluted to a density of about I > 1 O cells/ml. Mixtures of the Fc variant, diluted human complement and cells expressing the antigen may be added to a flat bottom tissue culture 96 well plate and allowed to incubate for 2 hrs at 37° C. and 5% $CO_2$ to facilitate complement mediated cell lysis. 50 μL of alamar blue (Accurned International) may then be added to each well and incubated overnight at 37° C. The absorbance is measured using a 96-well fluorometer with excitation at 530 nm and emission at 590 nm The results may be expressed in relative fluorescence units (RFU). The sample concentrations may be computed from a standard curve and the percent activity, relative to a comparable molecule.

Complement assays may be preformed with guinea pig, rabbit or human serum. Complement lysis of target cells maybe detected by monitoring the release of intracellular enzymes such as lactate dehydrogenase (LDH), as described in Korzeniewski et al., 1983. Immunol. Methods 64 (3): 313-20; and Decker et at., 1988, Immunol. Methods 115(1): 61-9; or the release of an intracellular label such as europium, chromium 51 or indium 111 in which target cells are labeled.

Treatment Methods

Methods are provided for treating a disease or disorder that is treatable with an ADCC-based antibody therapy in an individual. The methods generally involve: a) determining a category of responsiveness to an antibody therapy by genotyping the individual for an FcγRIIA polymorphism and an FcγRIIIA polymorphism; b) selecting an antibody from a set of related antibodies, where members of the set of related antibodies have the same antigen binding specificity, and differ in binding affinity to an FcγRIIA and/or an FcγRIIIA receptor; and c) administering an effective amount of the antibody to the individual.

Diseases and disorders that are treatable with an ADCC-based antibody therapy include, but are not limited to, neoplastic diseases; autoimmune diseases; allograft rejection; viral infections; bacterial infections; and parasitic infections.

Thus, in some embodiments, methods are provided for treating a neoplastic disease in an individual. The methods generally involve: a) determining a category of responsiveness to an antibody therapy for a neoplastic disease by genotyping the individual for an FcγRIIA polymorphism and an FcγRIIIA polymorphism; b) selecting an antibody from a set of related antibodies, where members of the set of related antibodies have the same antigen binding specificity, and differ in binding affinity and/or in vitro ADCC activity to an FcγRIIA and/or an FcγRIIIA receptor; and c) administering an effective amount of the antibody to the individual.

The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma; and the like.

In other embodiments, methods are provided for treating an autoimmune disease in an individual. The methods generally involve: a) determining a category of responsiveness to an antibody therapy for an autoimmune disease by genotyping the individual for an FcγRIIA polymorphism and an FcγRIIIA polymorphism; b) selecting an antibody from a set of related antibodies, where members of the set of related antibodies have the same antigen binding specificity, and differ in binding affinity and/or in vitro ADCC activity to an FcγRIIA and/or an FcγRIIIA receptor; and c) administering an effective amount of the antibody to the individual.

Autoimmune disorders include autoimmune hemolytic anemia, antiphospholipid syndrome, dermatitis, allergic encephalomyelitis, glomerulonephritis, Crohn's Disease, Goodpasture's Syndrome, Graves' Disease, multiple sclerosis, myasthenia gravis, neuritis, ophthalmia, bullous pemphigoid, pemphigus, acute disseminated encephalomyelitis, polyendocrinopathies, purpura, Reiter's Disease, stiff-Man syndrome, inflammation, Guillain-Barre Syndrome, insulin dependent diabetes mellitus (also referred to as Type 1 diabetes), rheumatoid arthritis, autoimmune inflammatory eye disease, adult respiratory distress syndrome, inflammatory bowel disease, dermatitis, immune thrombocytopenic purpura (ITP), Sjögren's syndrome, Waldenstrom's macroglobulinemia, encephalitis, uveitis, leukocyte adhesion deficiency, psoriatic arthritis, progressive systemic sclerosis, primary biliary cirrhosis, pemphigus, pemphigoid, necrotizing vasculitis, systemic lupus erythematosus, polymyositis, sarcoidosis, granulomatosis, Wegener's Granulomatosis (vasculitis), Type-II mixed cryoglobulinemia, pernicious anemia, CNS inflammatory disorder, antigen-antibody complex mediated diseases, Hashimoto's thyroiditis, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of acquired immunodeficiency syndrome (AIDS), atrophic gastritis, ankylosing spondylitis and Addison's disease.

In other embodiments, methods are provided for treating allograft rejection in an individual. The methods generally involve: a) determining a category of responsiveness to an antibody therapy for allograft rejection by genotyping the individual for an FcγRIIA polymorphism and an FcγRIIIA polymorphism; b) selecting an antibody from a set of related antibodies, where members of the set of related antibodies have the same antigen binding specificity, and differ in binding affinity and/or in vitro ADCC activity to an FcγRIIA and/or an FcγRIIIA receptor; and c) administering an effective amount of the antibody to the individual.

In other embodiments, methods are provided for treating a viral infection in an individual. The methods generally involve: a) determining a category of responsiveness to an antibody therapy for a viral infection by genotyping the individual for an FcγRIIA polymorphism and an FcγRIIIA polymorphism; b) selecting an antibody from a set of related antibodies, where members of the set of related antibodies have the same antigen binding specificity, and differ in binding affinity and/or in vitro ADCC activity to an FcγRIIA and/or an FcγRIIIA receptor; and c) administering an effective amount of the antibody to the individual.

As discussed above, the presence of a particular Fcγ receptor polymorphism predicts an individual's degree of responsiveness to an antibody therapy. Based on the individual's Fcγ receptor genotype, an antibody is chosen from a set of related antibodies. The set of related antibodies comprises members that have the same antigen binding specificity, and differ in binding affinity and/or in vitro ADCC activity to Fcγ receptors. Where the degree of responsiveness is predicted to be intermediate or low, an antibody is selected for enhanced binding to a given Fcγ receptor.

In some embodiments, the genotyping step identifies an FcγRIIA H/H$^{131}$ genotype and an FcγRIIIA V/V$^{158}$ genotype, and the Fc variant antibody is selected for enhanced binding and/or in vitro ADCC function to at least one of an FcγRIIA comprising His/His$^{131}$ allele and an FcγRIIIA comprising Val/Val$^{158}$ allele. In other embodiments, the genotyping step identifies: a) a H/H$^{131}$ genotype and a V/F$^{158}$ genotype, and wherein the Fc variant antibody is selected for enhanced binding and/or in vitro ADCC function to at least one of an FcγRIIA comprising H/H$^{131}$ allele and an FcγRIIIA comprising V/F$^{158}$ allele, and b) a H/H$^{131}$ genotype and a F/F$^{158}$ genotype, and wherein the Fc variant antibody is selected for enhanced binding and/or in vitro ADCC function to at least one of an FcγRIIA comprising H/H$^{131}$ allele and an FcγRIIIA comprising F/F$^{158}$ allele.

In other embodiments, the genotyping step identifies one of:

a) a V/F$^{158}$ genotype and a H/R$^{131}$ genotype, and wherein the Fc variant antibody is selected for enhanced binding and/or in vitro ADCC function to at least one of an FcγRIIA comprising H/R$^{131}$ allele and an FcγRIIIA comprising V/F$^{158}$ allele;

b) a V/F$^{158}$ genotype and a R/R$^{131}$ genotype, and wherein the Fc variant antibody is selected for enhanced binding and/or in vitro ADCC function to at least one of an FcγRIIA comprising R/R$^{131}$ allele and an FcγRIIIA comprising V/F$^{158}$ allele;

c) a F/F$^{158}$ genotype and a H/R$^{131}$ genotype, and wherein the Fc variant antibody is selected for enhanced binding and/or in vitro ADCC function to at least one of an FcγRIIA comprising H/R$^{131}$ allele and an FcγRIIIA comprising F/F$^{158}$ allele;

d) a F/F$^{158}$ genotype and a R/R$^{131}$ genotype, and wherein the Fc variant antibody is selected for enhanced binding and/ or in vitro ADCC function to at least one of an FcγRIIA comprising R/R$^{131}$ and an FcγRIIIA comprising F/F$^{158}$ allele;

e) a V/V$^{158}$ genotype and a H/R$^{131}$ genotype, and wherein the Fc variant antibody is selected for enhanced binding and/or in vitro ADCC function to at least one of an FcγRIIA comprising H/R$^{131}$ allele and an FcγRIIIA comprising V/V$^{158}$ allele; or f) a V/V$^{158}$ genotype and a R/R$^{131}$ genotype, and wherein the Fc variant antibody is selected for enhanced binding and/or in vitro ADCC function to at least one of an FcγRIIA comprising R/R$^{131}$ allele and an FcγRIIIA comprising V/V$^{158}$ allele.

Routes of administration, formulations, as well as dosages, of therapeutic antibodies are well known to those skilled in the art.

A therapeutic antibody is in some embodiments formulated into a preparation suitable for injection (e.g., subcutaneous, intravenous, intramuscular, intradermal, transdermal, intratumoral, peritumoral, intrathecal, or other injection routes) by dissolving, suspending or emulsifying the antibody in an aqueous solvent (e.g., saline, and the like) or a nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A therapeutic antibody is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{r1}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A therapeutic antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a therapeutic antibody is delivered by bolus injection. In other embodiments, a therapeutic antibody is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art. In other embodiments, a therapeutic antibody is administered by intravenous infusion.

In some embodiments, a therapeutic antibody is administered in an amount of from about 10 mg to about 1000 mg per dose, e.g., from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

In some embodiments, the dose of a therapeutic antibody is a weight-based dose, e.g., from about 50 mg/m$^2$ to about 100 mg/m$^2$, from about 100 mg/m$^2$ to about 150 mg/m$^2$, from about 150 mg/m$^2$ to about 200 mg/m$^2$, from about 200 mg/m$^2$ to about 250 mg/m$^2$, from about 250 mg/m$^2$ to about 300 mg/m$^2$, from about 300 mg/m$^2$ to about 350 mg/m$^2$, from about 350 mg/m$^2$ to about 400 mg/m$^2$, or from about 400 mg/m$^2$ to about 500 mg/m$^2$.

In some embodiments, multiple doses are administered. For example, in some embodiments, a therapeutic antibody is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

In some embodiments, a therapeutic antibody is administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Therapeutic formulations of an antibody may be prepared for storage as lyophilized formulations or aqueous solutions by mixing an antibody having the desired degree of purity with optional "pharmaceutically-acceptable" carriers, excipients or stabilizers typically employed in the art (all of which are termed "excipients"), i.e., buffering agents, stabilizing agents, preservatives, isotonifiers, non-ionic detergents, antioxidants, and other miscellaneous additives. See, e.g., Remington's Pharmaceutical Sciences, 16th edition, Osol, Ed. (1980). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives include phenol, benzyl alcohol, metacresol, methyl paraben, propyl paraben, octadecyldimethylbenzyl ammonium chloride, benzalconium halides (e.g., chloride, bromide, iodide), hexamethonium chloride, and alkyl parabens such as methyl or propyl paraben, catechol, resorcinol, cyclohexanol, and 3-pentanol.

"Stabilizers" may be added to ensure isotonicity of liquid compositions of antibodies and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect a therapeutic antibody against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic™ polyols, and polyoxyethylene sorbitan monoethers (TWEEN-20®, TWEEN-80®, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g., starch), chelating agents (e.g., EDTA), antioxidants (e.g., ascorbic acid, methionine, vitamin E), and cosolvents. The formulation may also contain more than one active compound as necessary for the particular indication being treated, preferably those with complementary activities that do not adversely affect each other. Such molecules are suitably present in combination in amounts that are effective for the purpose intended. The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, Osal, Ed. (1980).

Formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing an antibody, which matrices are in the form of shaped articles, e.g., films, or microcapsules. Examples of sustained-release matrices include polyesters, hydrogels (for example, poly(2-hydroxyethyl-methacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of identifying the presence of the target polymorphisms, where such reagents may include nucleic acid primers, arrays of nucleic acid probes, antibodies to polymorphic polypeptides (e.g., immobilized on a substrate), signal producing system reagents, etc., depending on the particular detection protocol to be performed.

In some embodiments, a subject kit comprises: i) an element for genotyping a sample to identify a FcγRIIA polymorphism; ii) an element for genotyping a sample to identify a FcγRIIIA polymorphism; and iii) a reference that correlates a genotype with predicted response to a therapeutic antibody. In some embodiments, the reference is a chart or table that correlates predicted degrees of responsiveness to a given therapeutic antibody to Fcγ receptor polymorphisms. Elements for genotyping include, e.g., nucleic acid probes, and nucleic acid primer sets. A sample will in some embodiments be a biological sample obtained from an individual, e.g., a blood sample or other sample that includes nucleic acid (e.g., genomic DNA) from the individual.

In some embodiments, the reference indicates a high degree of responsiveness to a given therapeutic antibody. In these embodiments, therapeutic antibody may be selected for administration to the individual. In other embodiments, the reference indicates an intermediate or low responsiveness; and choosing an Fc variant antibody that exhibits enhanced binding and/or in vitro ADCC function to an FcγRIIA and/or an FcγRIIIA is indicated. In some embodiments, a subject kit includes a set of related antibodies.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Example 1

Polymorphisms in FcγRIIA and FcγRIIIA; and Response to Rituximab

I. Materials and Methods
A. Patient Population

This study included 87 patients with follicular lymphoma, who were treated with rituximab at Stanford Medical Center between 1993 and 2003. They were selected because of the availability of their lymphoma tumor cells, peripheral blood or serum samples, and their known clinical response to rituximab. The pathology of all patient cases was reviewed. There were 47 patients with follicular small cleaved, 35 patients with follicular mixed, and five patients with follicular large-cell lymphoma. Fifteen patients had received rituximab as their first-line therapy. Seventy-two patients had received chemotherapy before rituximab, including 10 patients who had prior bone marrow transplantation. No patients received chemotherapy within the 2 months before rituximab treatment. Eighty-one patients had four weekly infusions of rituximab at 375 mg/m$^2$, five patients had eight weekly infusions of 375 mg/m$^2$, and one patient had four weekly infusions of 250 mg/m$^2$. Clinical responses were determined by physical examination and computed tomography scans between 1 and 3 months after last rituximab infusion and every 3 months thereafter. These responses were scored according to the Cheson criteria (Cheson B D, Horning S J, Coiffier B, et al.: Report of an international workshop to standardize response criteria for non-Hodgkin's lymphoma. *J. Clin. Oncol.* 17:1244-1253, 1999). Maximal clinical responses were observed at 1 to 3 months in all but three patients, who had partial responses at 1 to 3 months and showed additional tumor shrinkage at later time points. Pretreatment tumor cells were available in 43 patients and were used for in vitro ADCC assay. FcγR polymorphisms were analyzed in all 87 patients. This study was conducted according to a protocol approved by the institutional review board of our institution, and informed consent was obtained from all patients for the use of tissue samples and the analysis of clinical information.

B. Tumor Cells

Suspensions of pretreatment tumor cells isolated from lymph nodes were cryopreserved in liquid nitrogen. For ADCC assay, the tumor cells were thawed and subjected to Ficoll-Paque PLUS (Amersham Pharmacia Biotech, Piscataway, N.J.) gradient centrifugation to remove dead cells. The viability of tumor cells, determined by trypan blue dye exclusion at the time of assay, always exceeded 90%. The percentage of tumor cells in each sample was estimated by staining with antibodies specific for kappa or lambda light chains.

C. ADCC Assay

Lymphoma cells were labeled with chromium-51 ($^{51}$Cr) by incubating 3×10$^6$ cells with 450 μCi of $^{51}$Cr (Amersham Pharmacia Biotech) for 2 hours at 37° C. Cells were washed with RPMI-1640, and then incubated for 30 minutes at 37° C. with antibodies (at 10 μg/mL) Excess antibodies were removed by washing with medium. Mononuclear cells were obtained by Ficoll-Hypaque centrifugation of peripheral blood of a healthy donor (with FcγRIIIa V/V$^{158}$ genotype) and used as effector cells. One ×10$^4$ $^{51}$Cr-labeled target cells were incubated for 4 hours at 37° C. with the indicated number of effector cells in 200 μL of RPMI-5 medium (RPMI-1640, 10 mmol/L HEPES, 5% heat-inactivated human AB serum, 1% L-glutamine). Fifty microliters of medium was collected after 4 hours of incubation and counted in a Micro-Beta 1450 scintillation counter (Wallac, Turku, Finland). Spontaneous $^{51}$Cr release was determined in the absence of effector cells. Maximal $^{51}$Cr release was determined by lysis with 0.5% Triton X-100. All samples were assayed in triplicate. The specific $^{51}$Cr release was determined by subtracting the spontaneous $^{51}$Cr release from that of the treatment wells, then dividing the result by the maximal $^{51}$Cr release minus spontaneous $^{51}$Cr release. All the tumor samples had coexistent T-cells of variable degree (Table-1). To compare different tumor samples, the specific ADCC is calculated by dividing the specific $^{51}$Cr release in rituximab-treated samples minus $^{51}$Cr release in control IgG1-treated samples by the percentage of CD20-positive cells in individual samples.

D. Analysis of FcγRIIIA and FcγRIIA Polymorphisms

Genomic DNA was prepared from tumor cells or from peripheral-blood mononuclear cells using a DNA extraction kit (Qiagen, Valencia, Calif.). In six patients, DNA was prepared from the serum using a described method (Kopreski M S, Benko F A, Kwee C, et al.: Detection of mutant K-ras DNA in plasma or serum of patients with colorectal cancer. *Br. J. Cancer* 76:1293-1299, 1997). Genotyping of FcγRIIIA V/F$^{158}$ and FcγRIIA H/R$^{131}$ polymorphisms was performed by a polymerase chain reaction followed by allele-specific restriction enzyme digestion (Koene H R, Kleijer M, Algra J, et al.: Fc-gamma-RIIIA-158 V/F polymorphism influences the binding of IgG by natural killer cell Fc-gamma-RIIIa, independently of the Fc-gamma-RIIIA-48 L/R/H phenotype. *Blood* 90:1109-1114, 1997; Jiang X-M, Arepally G, Poncz M, et al.: Rapid detection of the Fc-gamma-RIIA-H/R131 ligand-binding polymorphism using an allele-specific restriction enzyme digestion (ASRED). *J. Immunol. Methods* 199: 55-59, 1996). All genotyping of FcγRIIIA polymorphism was confirmed by direct sequencing of the region of interest.

E. Statistical Analysis

Differences in the means of ADCC killing were tested by single-factor analysis of variance test and checked by the Kruskal-Wallis (nonparametric) test. The clinical responses of the patients were compared using a two-tailed Fisher's exact test (PRISM for Macintosh; GraphPad Software, San Diego, Calif.). A logistic regression analysis including age (≥ or <60 years), stage (III v IV), presence of bulky disease, number of extranodal sites (≥two or <two), prior bone marrow transplantation, and FcγRIIA and FcγRIIIA genotype was used to identify independent prognostic variables influencing the clinical responses (StatView 5.0.1; SAS Inc, Cary, N.C.).

II. Results

A. Rituximab-Mediated ADCC in Follicular Lymphoma Cells

The ability of rituximab to mediate ADCC in follicular lymphoma cells was determined. Pretreatment lymphoma cells from 43 patients were tested using effector cells isolated from one healthy donor. Rituximab-mediated ADCC was detected in all 43 patient samples (range, 13.5% to 100%). As expected, the murine antibody of rituximab, 2B8, which contains a mouse γ1 Fc portion and binds lymphoma cells identically to rituximab, did not mediate ADCC (data not shown).

The relation of the observed ADCC susceptibility of lymphoma cells from individual patients to their clinical response to rituximab therapy was then evaluated. Patients were subdivided into nonresponders (NR), partial responders (PR), and complete responders (CR) according to their response to rituximab at the first evaluation at 1 to 3 months (Table 1, FIG. 5). The range of ADCC varied widely in all three Groups (NR, 16.9% to 80.6%; PR, 13.5% to 57.0%; CR, 20.9% to 100.0%; FIG. 1). However, there was no difference of rituximab-mediated ADCC between the three Groups (means±standard deviations: NR, 44.6%±18%; PR, 40.0%±12%; CR, 53.6%±23%). Additional analysis showed no relationship between rituximab-mediated ADCC and response when clinical response was scored at 6, 9, or 12 months after treatment, nor did the susceptibility to ADCC correlate with the duration of remission (data not shown). In a subGroup of 29 patients whose tumors were studied in a report on complement-mediated cytotoxicity, (Weng W-K, Levy R: Expression of complement inhibitors CD46, CD55, and CD59 on tumor cells does not predict clinical outcome after rituximab treatment in follicular non-Hodgkin lymphoma. *Blood* 98:1352-1357, 2001) the expression of CD20 on their lymphoma cells had previously been determined by flow cytometric staining. Within this subGroup, there was no correlation between the expression of CD20 and rituximab-mediated ADCC (r=−0.03; P=0.88).

B. Clinical Response to Rituximab Therapy and FcγRIIIA V/F$^{158}$ Polymorphism The FcγRIIIA (CD16) of V allele demonstrates higher affinity to IgG1 than the F allele and mediates ADCC more effectively. Recently, Cartron et al., (Cartron G, Dacheux L, Salles G, et al.: Therapeutic activity of humanized anti-CD20 monoclonal antibody and polymorphism in IgG Fc receptor Fc-gamma-R IIIA gene. *Blood* 99:754-758, 2002) have shown an association between FcγRIIIA V/V$^{158}$ genotype and higher response rate in patients treated with first-line rituximab. This association was assayed in the subject patient Group, the majority of whom were treated for relapsed disease. The study Group was expanded to 87 by acquiring peripheral blood or serum samples from additional rituximab-treated patients.

Figure 2:
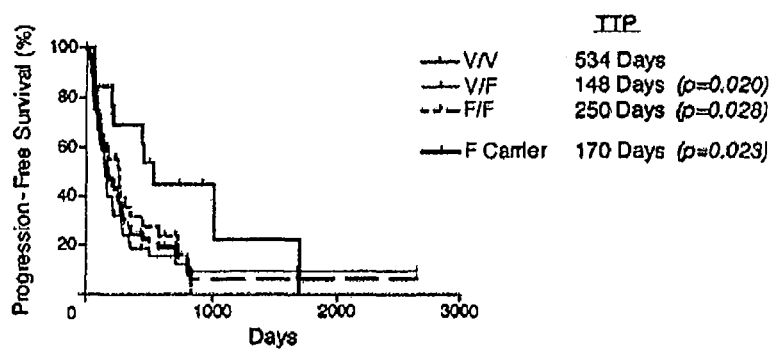
FIG. 2: Kaplan-Meier estimates of progression free survival by IgG Fc receptor IIIA (FcγRIIIA) 158 valine (V)/ phenylalanine (F) polymorphism. Progression-free survival (PFS) curves were plotted by FcγRIIIA $V/F^{158}$ genotype on all 87 patients. F carriers represent patients with either V/F$^{158}$ or F/F$^{158}$ genotype. TTP, median time to progression.

In this sample set, 13 patients (15%) had homozygous V/V (V/V$^{158}$), 40 (46%) had heterozygous V/F (V/F$^{158}$), and 34 (39%) had homozygous F/F (F/F$^{158}$). The three groups were not different in terms of average age at the time of treatment, number of prior chemotherapy courses, or time between diagnosis and treatment (Table 2, FIG. 6). The response rate in patients with V/F$^{158}$ and in patients with F/F$^{158}$ was similar at all four time points (Table 3, FIG. 7). For that reason, the groups V/F$^{158}$ and F/F$^{158}$ were combined together as the F carrier for statistical analysis. A significant difference was detected between the response rates of V/V$^{158}$ and F carriers (Table 3, FIG. 7). The progression-free survival (PFS) at 2 years was 45% for patients with 158 V/V, 12% for 158 V/F, 16% for 158 F/F, and 14% for F carriers, using the Kaplan-Meier estimation, with median time to progression (TTP) of 534, 148, 250, and 170 days for each Group, respectively. The PFS estimate of patients with V/V$^{158}$ was significantly longer than that for patients with V/F$^{158}$, F/F$^{158}$, or F carriers (FIG. 2).

Figure 3:
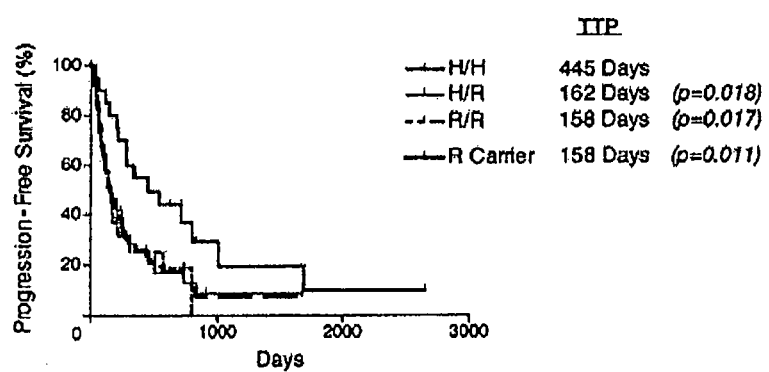
FIG. 3: Kaplan-Meier estimates of progression-free survival (PFS) by IgG Fc receptor IIA (FcγRIIA) 131 histidine (H)/arginine (R) polymorphism. PFS curves were plotted by FcγRIIA H/R$^{131}$ genotype on all 87 patients. R carriers represent patients with either H/R$^{131}$ or R/R$^{131}$ genotype. TTP, median time to progression.

C. Clinical Response to Rituximab Therapy and FcγRIIA H/R$^{131}$ Polymorphism The FcγRIIA (CD32) is another activating FcγR that is expressed only on macrophages but not on natural killer (NK) cells. An H/R polymorphism at position 131 of FcγRIIA has been found to affect its affinity to human IgG (Jiang X-M, Arepally G, Poncz M, et al.: Rapid detection of the Fc-gamma-RIIA-H/R131 ligand-binding polymorphism using an allele-specific restriction enzyme digestion (ASRED). *J. Immunol. Methods* 199:55-59, 1996). Of the 87 patients in the Group, 20 (23%) had homozygous H/H (H/H$^{131}$), 43 (49%) had heterozygous H/R (H/R$^{131}$), and 24 (28%) had homozygous R/R (R/R$^{131}$). Once again, the three Groups were not different in terms of average age at the time of treatment, number of prior chemotherapy treatments, or time between diagnosis and treatment (Table 2, FIG. 6). Although there was no difference in the response rate at 1 to 3 months between the three Groups, patients with H/H$^{131}$ showed a significantly higher response rate than the other two Groups combined (H/R and R/R [R carrier]) at 6, 9, and 12 months (Table 4, FIG. 8). This higher response rate also translated to longer remission: the PFS at 2 years was 37% for patients with H/H$^{131}$, 13% for H/R$^{131}$, 19% for R/R$^{131}$, and 14% for R carrier using the Kaplan-Meier estimation with TTP of 445, 162, 158, and 158 days for each Group, respectively. The PFS estimate for patients with H/H$^{131}$ was significantly longer than for patients with other genotypes (FIG. 3).

Figure 4:
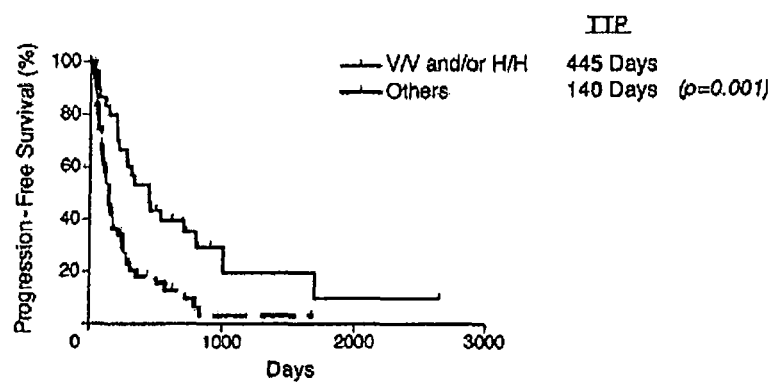
FIG. 4: Progression free survival (PFS) by IgG Fc receptor IIIa (FcγRIIIA) V/F$^{158}$ and FcγRIIA H/R$^{131}$ polymorphisms. PFS curves were plotted by FcγRIIIA V/F$^{158}$ and FcγRIIA H/R$^{131}$ genotype. Others represent patients without either FcγRIIIA V/V$^{158}$ or FcγRIIA H/H$^{131}$ genotype. TTP, median time to progression.
Figure 17:
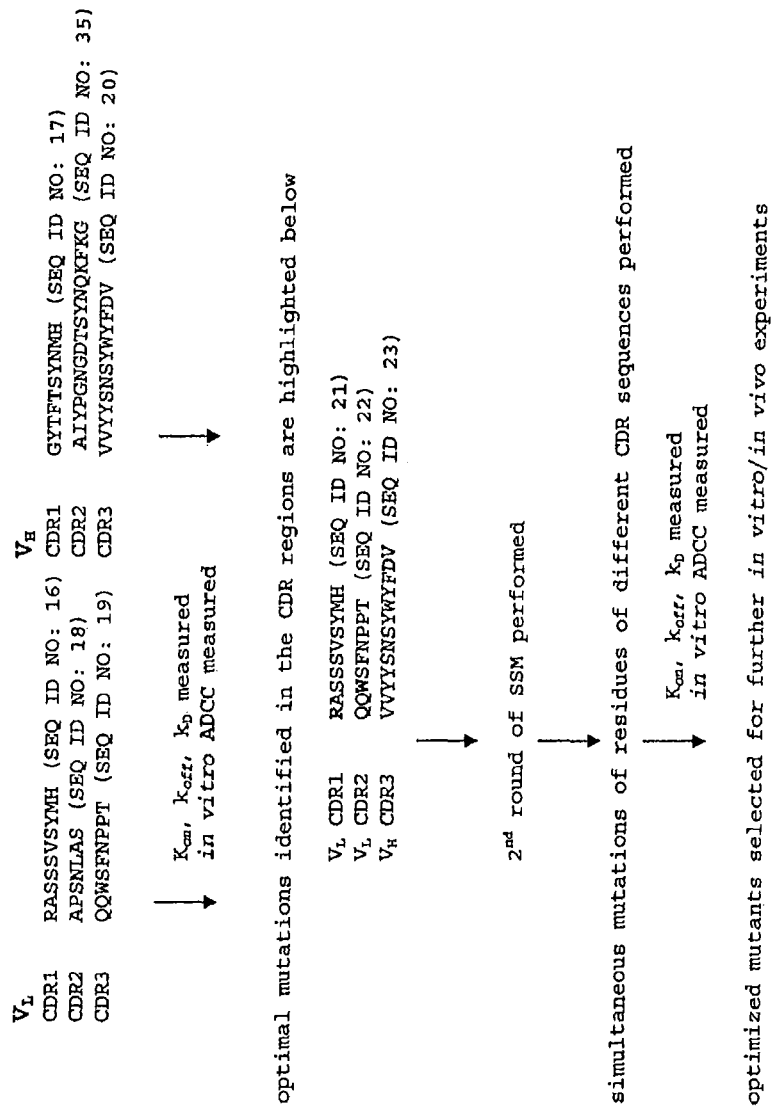
FIG. 17: Simultaneous SSM of the CDR regions of V$_L$ (SEQ ID NO: 16, SEQ ID NO: 18, SEQ ID NO: 19) and V$_H$ (SEQ ID NO: 17, SEQ ID NO: 35, SEQ ID NO: 20) sequences of Rituximab. Optimal mutations identified in the CDR regions are highlighted (V$_L$ CDR1—SEQ ID NO:21; V$_L$ CDR2—SEQ ID NO:22; V$_H$ CDR3—SEQ ID NO:23).

The possibility of an association between FcγRIIIA and FcγRIIA genotypes that might explain the correlation of the two with response rate was examined. As shown in Table 5, FIG. 9, there was no significant difference in the fraction of V/V$^{158}$ or F carrier in three H/R$^{131}$ genotypes. The combination of FcγRIIIA V/V$^{158}$ and/or FcγRIIa H/H$^{131}$ was then analyzed, and their relationship to rituximab response. As shown in Table 6, FIG. 10, patients with V/V$^{158}$ and/or H/H$^{131}$ (total of 30 patients) had a significantly higher response rate than patients without either genotype at all four time points (83% v 54%, P=0.009 at 1 to 3 months; 80% v 34%, P=0.0001 at 6 months; 69% v 26%, P=0.0003 at 9 months; 59% v 18%, P=0.0004 at 12 months). The PFS estimate of patients with V/V$^{158}$ and/or H/H$^{131}$ was also significantly longer (P=0.001), with TTP of 445 and 140 days for the two Groups, respectively (FIG. 4). By logistic regression analysis, FcγRIIIA V/V$^{158}$ genotype emerged as the only predictive factor for response at 1 to 3 months, whereas both the FcγRIIIA V/V$^{158}$ genotype and FcγRIIA H/H$^{131}$ genotype were identified as independent predictive factors for response at 6, 9, and 12 months (Table 7, FIG. 11).

III. Discussion

In this study, the observation of Cartron et al., supra, that V/V$^{158}$ genotype is associated with higher response rate to rituximab treatment was confirmed. However, there were significant differences between the present and prior studies. First, the response rate in the patient Group of the present study was lower than that in the previous report, especially at 12 months after treatment. This observation is consistent with previous observations of a lower response rate when rituximab is used as second-line treatment. In addition, the patients of the present study probably had higher tumor burden because 53% of them had bulky (5 cm) disease compared with the previous study in patients with nonbulky disease. Second, although F carriers (V/F and F/F) showed a significantly lower response rate, the response rate in patients with F/F$^{158}$ was slightly higher than that in patients with V/F$^{158}$. The biologic explanation of this phenomenon is unclear, given that patients with V/F$^{158}$ would be expected to have an intermediate response rate. Third, consistent with the previous report, we detected a difference between V/V$^{158}$ and F carrier. However, one interesting observation in this study is that the difference became more pronounced after longer times from the treatment. The antibody is known to persist for up to 6 months, and its effect may be cumulative.

The most unexpected result came from the analysis of FcγRIIA polymorphism. The allele of H/H$^{131}$ binds to human IgG2 better than that of R/R$^{131}$. However, no significant difference in the affinity of these two allelic forms for human IgG1 has been noted. (Parren P W, Warmerdam P A, Boeije L C, et al.: On the interaction of IgG subclasses with the low affinity Fc-gamma-RIIa (CD32) on human monocytes, neutrophils, and platelets: Analysis of a functional polymorphism to human IgG2. *J. Clin. Invest.* 90:1537-1546, 1992). Therefore, it was unexpected to find a higher rituximab response rate associated with H/H$^{131}$ genotype (Table 4, FIG. 8). Similar to the FcγRIIIA V/F$^{158}$ polymorphism, a gene dosage effect of the 131H allele was not observed. Instead, the response rate in patients with H/R$^{131}$ was similar to that of R/R$^{131}$ at 6, 9, and 12 months. The biologic explanation of this observation is not clear. The association between FcγRIIA H/H$^{131}$ and higher response rate was not a result of a linkage disequilibrium of FcγRIIIA V/F$^{158}$ polymorphism (Table 5, FIG. 9). There is a random distribution of combinations of variant genotypes of FcγRIIA and FcγRIIIA in the normal population. (Lehrnbecher T, Foster C B, Zhu S, et al.: Variant genotypes of the low-affinity Fc-gamma receptor in two control populations and a review of low-affinity Fc-gamma receptor polymorphisms in control and disease populations. *Blood* 94:4220-4232, 1999).

The FcγRIIA H/R$^{131}$ polymorphism is an independent predictive factor for clinical response: In the subGroup of patients with 158 F carrier, FcγRIIA H/H$^{131}$ genotype was associated with higher response rate at 6, 9, and 12 months (H/H=76% v R carrier=34%, P=0.004 at 6 months; H/H=65% v R carrier=26%, P=0.007 at 9 months; H/H=47% v R carrier=18%, P=0.026 at 12 months). Furthermore, all three patients with both V/V$^{158}$ and H/H$^{131}$ genotypes had long-lasting remissions (Table 6, FIG. 10). Patients with V/V$^{158}$ and/or H/H$^{131}$ genotypes showed a higher response rate and a longer remission than did patients without either of these two genotypes (Table 6, FIG. 10). Lastly, the logistic regression analysis showed that the V/V$^{158}$ and H/H$^{131}$ were independent predictive factors for response at 6, 9, and 12 months. The report of Cartron et al., supra, also analyzed the FcγRIIA H/R$^{131}$ polymorphism and concluded that the FcγRIIA polymorphism did not influence the clinical response. However, it is important to point out that Cartron et al., analyzed a smaller Group of patients (N=45) and scored the clinical responses only at 1 and 12 months. In this study, the most prominent differences were observed at 6 and 9 months (Table 4, FIG. 8).

To reiterate, this study established a) for the first time a clear role for ADCC in the clinical effects (treatment response and freedom of progression) of rituximab at the level of the effector cell was established through in vitro ADCC assays and by correlating this to specific FcγRIIIA polymorphism, b) through a rigorous time-course analysis, an unequivocal proof that FcγRIIA H/R$^{131}$ polymorphism is independently associated with the therapeutic response rate, and c) both the FcγRIIIA V/F$^{158}$ and the FcγRIIA H/R$^{131}$ polymorphisms are independently and collectively associated with the therapeutic response rate and freedom from progression, which is to say that details of both polymorphisms are absolutely essential to make a meaningful prediction of the therapeutic response rate. This work has provided a sequential correlation between FcγRIIIA V/F$^{158}$ polymorphism, in vitro ADCC, and the clinical effect of rituximab. Although similar in vitro ADCC experiments were not conducted to test such a relationship for FcγRIIA H/R$^{131}$ polymorphism in these patients, the direct correlation between the H/R$^{131}$ polymorphism and the clinical effect of rituximab is unequivocally established in this study. Thus, given the central role for these two receptors in ADCC, a) patients can be classified into nine Groups based on these polymorphisms, b) it is possible to generate Fc variant antibodies specific for FcγRIIIA and FcγRIIA alleles by selecting for enhanced binding and/or in vitro ADCC function, c) it is comprehended that, like rituximab, many other antibodies exert their therapeutic efficacy through ADCC as the major mechanism of action, and therefore, d) the patient Group specific Fc variants contemplated in this disclosure can be used to enhance the therapeutic response of these antibodies to treat ADCC-treatable diseases or disorders.

Example 2

Construction of Patient Group Specific Fc Variant Antibodies

Throughout this example, methods are described to generate Fc variants optimized for FcγRIIIA F/F$^{158}$ and FcγRIIA R/R$^{131}$ genotypes (Patient Group-IX; See, e.g., Table D). While Rituximab is shown as an example, any other ADCC-dependent antibody can be used in these experiments with appropriate modifications in the procedures. For preliminary binding studies which involve SSM and Fc Walking, aglycosylated Fc fragment including the hinge as well as the soluble domains of FcγRIIIA and FcγRIIA are expressed in vitro or through bacterial expression by established procedures (Kim et al., *Eur. J. Immunol.* 24:542, 1994; Sondermann and Jacob, *Biol. Chem.* 380:717-721, 1999).

FC ENGINEERING AND BINDING STUDIES:

For each chosen residue, in vitro scanning saturation mutagenesis (SSM) is carried out (U.S. Pat. No. 6,180,341). Briefly, at each site, twenty-one genes encoding all possible amino acid substitutions as well as a double stop codon (control) are constructed by overlap extension PCR. The following conserved stretches of the Fc region will be subjected to both SSM and Fc Walking, one residue at a time, in order to generate single mutants: L$^{234}$-S$^{239}$ (6×20=120 variants), R$^{255}$-T$^{260}$ (6×20=120 variants); D$^{265}$-E$^{269}$ (5×20=100 variants); N$^{297}$-T$^{299}$ (3×20=60 variants); A$^{327}$-I$^{332}$ (6×20=120 variants) (See, e.g., FIG. 12-C). In addition, approximately 5-10 residues upstream and downstream of the conservative stretches will also be subjected to Fc Walking (FIG. 12-D). Taken together, this generates <2000 Fc variants. Similarly, double and triple mutants are generated by combining the single mutants and additionally selecting for the binding properties (Yang et al., *J. Mol. Biol.* 254:392, 1995; Wu et al., *Proc Natl. Acad. Sci. USA* 95:6037, 1998). This is accomplished by simultaneous SSM at 3-5 different positions. The final products of the overlap extension PCR reaction contain a T7 promoter and ribosome binding site in front of the Fc fragment gene. An HSV sequence is also present at the C-terminal end of the Fc fragment gene, so that the MAb fragment protein can be detected by ELISA using an anti-HSV monoclonal antibody. The PCR overlap extension products are used as templates for coupled in vitro transcription-translation reactions to produce Fc variants. An *E. coli* S30 ribosomal extract is used for in vitro translation.

The protein products from the coupled in vitro transcription-translation step are analyzed by ELISA. In ELISA, 96-well microtiter plates are coated with the BSA conjugate of soluble FcγRIIIA $F^{158}$ or FcγRIIA $R^{131}$. The plates are then incubated with equal amounts from each of the in vitro synthesis reactions. In order to provide accurate calibration, the construct prepared with the Fc wild-type sequence is used on each ELISA plate. The Fc wild-type construct is produced by the overlapping PCR method alongside the mutants, thereby providing an accurate calibration for all stages of the procedure. Heterogeneity of the transcribed/translated products is verified by DNA/protein sequencing protocols, or matrix-assisted laser desorption/ionization time-of-flight mass spectrometry (MALDI-TOF-MS). The ELISA results for the different mutants are recorded and the promising Fc variants in terms of binding and affinity are subjected to in vitro ADCC assays (See, e.g., below).

Construction, Expression, and Purification of Fc Variant Antibodies and FcγRs:

The wild-type Fc region of rituximab is substituted with Fc variants generated through Fc engineering, cloned and expressed in 293T cells, and purified by using protein-A chromatography. FcγRs are constructed as C-terminal 6×His-GST fusions, expressed in 293T (human FcγRs) or NIH 3T3 (mouse FcγRIII) cells, and purified by using nickel affinity chromatography. Heterogeneity of the translated products is tested by any one of the following analytical procedures: SDS-PAGE, gel filtration, MALDI-TOF-MS.

Binding Assays:

AlphaScreen assays use untagged Ab to compete the interaction between biotinylated IgG bound to streptavidin donor beads and FcγR-His-GST bound to anti-GST acceptor beads. Competition SPR (Harvey et al., *Proc. Natl. Acad. Sci. USA* 101:9193, 2004) experiments measured capture of free Ab from a preequilibrated Ab:receptor analyte mixture to FcγRIIIa $V^{158}$-His-GST bound to an immobilized anti-GST surface. Equilibrium dissociation constants ($K_D$ values) are calculated by using the proportionality of initial binding rate on free Ab concentration in the Ab:receptor equilibrium (Schier et al., *J. Mol. Biol.* 255:28, 1996; Daugherty et al., *Protein Engg.* 11:825-832, 1998).

in vitro ADCC is measured by $^{51}$Cr release assay (Weng and Levy, *J. Clin. Oncol.* 21:3940, 2003). Human PBMCs are purified from leukopacks by using a Ficoll gradient and allotyped for FcγRIIIa $F/F^{158}$ and FcγRIIa $R/R^{131}$ by PCR. NK cells are isolated from human PBMCs by negative selection using a magnetic bead NK cell isolation kit (Miltenyi Biotech, Auburn, Calif.). All the necessary target cell lines are obtained from American Type Culture Collection. As a second format, ADCC assay using PBMC as effector cells is measured based on lactate dehydrogenase activity released from the dead or plasma membrane damaged cells (Shields et al., *J. Biol. Chem.* 276:6591, 2001).

For phagocytosis experiments, monocytes are isolated from PBMCs of individuals belonging to the Patient Group-IX (FcγRIIIa $F/F^{158}$ and FcγRIIa $R/R^{131}$) by using a Percoll gradient and differentiated into macrophages by culturing in a medium supplemented with 0.1 ng/ml granulocyte macrophage colony-stimulating factor for 1 week. For imaging, WIL2-S target cells are labeled with PKH67 (Sigma) and cocultured for 24 h with macrophages at an effector:target cell ratio of 3:1 in the presence of 100 ng/ml Fc variant rituximab optimized for the Patient Group-IX. Cells are then treated with secondary antibodies anti-CD11-RPE and anti-CD14-RPE (DAKO) for 15 minutes before live cell imaging using a fluorescence microscope. For quantitative ADCP (antibody-dependent cell-mediated phagocytosis), WIL2-S target cells are labeled with PKH67, seeded in a 96-well plate at $20 \times 10^3$ cells per well, and treated with WT or the Fc variant rituximab at the designated final concentrations. Macrophages are labeled with PKH26 (Sigma) and added to the opsonized labeled target cells at $20 \times 10^3$ cells per well, and the cells are cocultured for 18 h. Fluorescence is measured by using dual-label flow cytometry. Fc variant antibodies with increased potency and efficacy are selected. CDC assays are performed according to published procedures (Gazzano-Santoro et al., *J. Immunol. Meth.* 202:163, 1997; Uchida et al., *J. Exp. Med.* 199:1659, 2004).

In Vivo B-Cell Depletion:

Cynomolgus monkeys (*Macaca fascicularis*) will be injected intravenous once daily for 4 consecutive days with wild-type or the Fc variant rituximab optimized for the Patient Group-IX (Reff et al., *Blood* 83:435-445, 1994). The test animals will be allotyped for the FcγR polymorphisms, and if required, the animals corresponding to $F/F^{158}$ and $R/R^{131}$ genotypes will be used for the experiment. The experiment is comprised of six treatment Groups of ~0.1, 0.2, 2, 7, or 30 µg/kg (Group-IX specific variant rituximab) or ~2 or 30 µg/kg (wild-type control), with three monkeys per treatment Group. Blood samples are acquired on two separate days before dosing (baseline) and at days 1, 2, 5, 15, and 28 after initiation of dosing. For each sample, cell populations are quantified by flow cytometry by using specific antibodies against the representative marker antigens. Percent B-cell depletion is calculated by comparing B-cell counts on the given day with the average of the two baseline measures for each animal.

Example 3

ADCC Improvement Through CDR Engineering

Antibodies or antibody fragments are specifically optimized to a patient Group according to their FcγRIIA and FcγRIIIA polymorphism as described in Example 2. However, instead of introducing amino acid modifications (i.e., insertions, substitutions, deletions, etc.) into the Fc portion of the antibody, as described in Example 2, modifications are introduced in the complementarity determining regions (CDRs) of the antibody.

CDR engineering of Rituxan is shown here as an example. FIG. 16 shows the codon-based mutagenesis of the light chain CDR2 region (APSNLAS). Scanning saturation mutagenesis (Burks et al. *Proc. Natl. Acad. Sci. USA* 94:412, 1997; Chen et al. *Protein Engg.* 12:349, 1999) is used in a stepwise fashion to rapidly improve the affinity of the CD20-binding fragment by greater than 50-100 fold. The focused library of $V_L$ CDR2 region will have 140 variants. In the absence of structural information about the Rituxan-CD20 interactions, in vitro translated antibody libraries for all six light and heavy chain CDRs will be screened by a quantitative assay ($k_{on}$, $k_{off}$, $K_d$, in vitro ADCC assay) to identify variants with improved binding to CD20. The Rituxan variants in these libraries each contains a single mutation, and all 20 amino acids are introduced at each CDR residue, resulting in a library consisting of 1,320 unique variants. Multiple clones displaying 2- to >10 fold improved affinity are identified. The CDR residues identified as "critical" (optimal) residues for engineering (FIG. 16) will be subjected to second round of scanning saturation mutagenesis. Where necessary, simultaneous mutations of 3-4 changes in multiple CDR sequences are made. Promising scFv variants were converted into IgG1 format, cloned, and expressed in 293T cells, and purified by standard procedures. Binding assays and in vitro ADCC assays are carried out essentially as described in Example II.

Example 4

Engineering, Screening and Selection of Optimized Patient Group Variant Rituximab Antibodies Antibodies or antibody fragments are specifically optimized for a patient Group based on their FcγRIIA and FcγRIIIA polymorphism. For example, patients are categorized into Groups according to their FcγRIIA (H/R$^{131}$) polymorphism and their FcγRIIIA (V/F$^{158}$) polymorphism. Consequently, patients can be divided into nine genotypic Groups, including: V/V$^{158}$, H/H$^{131}$ (Group-I); V/F$^{158}$, H/H$^{131}$ (Group-II); F/F$^{158}$, H/H$^{131}$ (Group-III); V/V$^{158}$, H/R$^{131}$ (Group-IV); V/F$^{158}$, H/R$^{131}$ (Group-V); F/F$^{158}$, H/R$^{131}$ (Group-VI); V/V$^{158}$, R/R$^{131}$ (Group-VII); V/F$^{158}$, R/R$^{131}$ (Group-VIII); and F/F$^{158}$, R/R$^{131}$ (Group-IX) (See, e.g., Table D). Notably, an antibody can be optimized for each patient Group except for the Group or Groups that exhibit the highest degree of responsiveness to the antibody therapy.

A variant antibody specific for a particular patient Group (genotype) is engineered such that the variant antibody exhibits responsiveness optimized to the patient Groups (genotypes) which exhibit a higher degree of responsiveness to the parent antibody. In some embodiments, a variant antibody specific for a particular patient Group (genotype) is engineered such that the variant antibody exhibits responsiveness optimized to the patient Group which exhibits the highest degree of responsiveness to the parent antibody.

Responsiveness to an antibody therapy for a neoplastic disease can include one or more of: antibody-dependent cell-mediated cytotoxicity (ADCC) response to tumor cells; reduction in tumor mass; reduction in number of tumor cells.

Responsiveness to an antibody therapy for an autoimmune disease can include one or more of: reduction in a symptom associated with the autoimmune disorder; reduction in the number and/or activity of an autoreactive B-cell; reduction in the number and/or activity of an autoreactive T-cell; etc.

Responsiveness to an antibody therapy for allograft rejection can include one or more of: reduction in the amount of immunosuppressive drug that must be administered to an individual who is the recipient of an allograft and still maintain the allograft; duration of maintenance of the allograft; function of the allograft; reduction in the number and/or activity of alloreactive T-cells in the allograft recipient.

Responsiveness to an antibody therapy for a viral infection can include one or more of: reduction in the number of viral genomes in a tissue, fluid, or other specimen from an individual; reduction in one or more symptoms of a viral infection; etc.

Responsiveness may be determined at various times after treatment with a given antibody therapy, e.g., 1, 2, 3, 4, 5, 6, 7, 8, 9, 10, 11 and 12 months following treatment, e.g., following initiation of treatment. Thus, e.g., responsiveness can be expressed with a time component.

For example, when Rituximab is the antibody of interest, a variant Rituximab antibody is engineered for each patient Group, except the Group associated with the highest degree of responsiveness to Rituximab (Group-I). Variant Rituximab antibodies are then optimized for each patient Group such that each Group exhibits an increased degree of responsiveness to the variant antibody. In some embodiments, the variant Rituximab antibodies are optimized for each patient Group exhibit a similar degree of responsiveness as exhibited by the patients of Group-I to Rituxamab. Given that Group-I genotype is associated with the highest degree of responsiveness to Rituxamab, variant Rituximab antibodies are only engineered and optimized for patient Groups II-IX.

While the example described below are directed toward the V/F$^{158}$, H/H$^{131}$ genotype, it will be understood that the same protocols may be employed to engineer optimized antibodies for the F/F$^{158}$, H/R$^{131}$ genotype (Group-III); the V/V$^{158}$, H/R$^{131}$ genotype (Group-IV); the V/F$^{158}$, H/R$^{131}$ genotype (Group-V); the F/F$^{158}$, H/R$^{131}$ genotype (Group-VI); the V/V$^{158}$, R/R$^{131}$ genotype (Group-VII); the V/F$^{158}$, R/R$^{131}$ genotype (Group-VIII); and the F/F$^{158}$, R/R$^{131}$ genotype (Group-IX) (See, e.g., Table D).

A. Patient Group-II (V/F$^{158}$, H/H$^{131}$ Genotype)

Variant Rituximab antibodies engineered for Group-II (V/F$^{158}$, H/H$^{131}$ genotype) are optimized to exhibit an increased degree of responsiveness comparable to any other Group with a higher responsiveness to the antibody. In some embodiments, variant Rituximab antibodies engineered for Group-II (V/F$^{158}$, H/H$^{131}$) are optimized to exhibit a degree of responsiveness comparable to the level of H/H$^{131}$) to Rituxamab.

1. Engineering Variant Rituximab Antibodies for Patient Group-II (V/F$^{158}$, H/H$^{131}$ Genotype)

The Fc region and CDRs of Rituximab may be engineered to create variant Rituximab antibodies. Antibody variants can be obtained by substitution, deletion, inversion, and/or insertion of any of the amino acids present in the antibody. For example, Fc variant antibodies can be obtained by substitution of any of the amino acids present in the Fc fragment. Likewise, CDR variant antibodies can be obtained by deletion of any of the amino acids present in the CDRs. As can be appreciated, there are positions in the sequence that are more tolerant to substitutions, deletions, inversions, and/or insertions than others, and with some amino acid modifications improving the binding activity of the parent antibody. The amino acids that are essential should either be identical to the amino acids present in the parent antibody, or substituted by conservative substitutions. The amino acids that are non-essential can be identical to those in the parent antibody, or can be substituted by conservative or non-conservative substitutions, and/or can be deleted.

The substitutions, deletions, inversions, and/or insertions of amino acids in an Fc variant antibody will occur in regions not essential to antigen binding. The identification of essential and non-essential amino acids in the antibody can be achieved by methods known in the art, such as by site-directed mutagenesis (for example, SSM) and AlaScan analysis (Moffison et. al., *Chem. Biol.* 5:302-307, 2001). Essential amino acids have to be maintained or replaced by conservative substitutions in the variants. Non-essential amino acids can be deleted, or replaced by a spacer or by conservative or non-conservative substitutions.

The following conserved stretches (bolded and underlined) in the Fc region of Rituximab (SEQ ID NO: 1) may be subjected to both SSM (See, e.g., U.S. Pat. No. 6,180,341) and Fc Walking, one residue at a time, in order to generate single mutants: L$^{234}$-S$^{239}$ (6×20=120 variants), R$^{255}$-T$^{260}$ (6×20=120 variants); D$^{265}$-E$^{269}$ (5×20=100 variants); N$^{297}$-T$^{299}$ (3×20=60 variants); A$^{327}$-I$^{332}$ (6×20=120 variants) (See, e.g., FIG. 12-C). Briefly, at each site, twenty-one genes encoding all possible amino acid substitutions as well as a double stop codon (control) are constructed by overlap extension PCR. In addition, approximately 5-10 residues upstream and downstream of the lower hinge, B/C loop, C'/E loop and F/G loop are also subjected to Fc Walking (FIG. 12-D). Taken together, this generates <2000 Fc variants.

Similarly, the Fc region in REMICADE® (SEQ ID NO: 5), ERBITUX® (SEQ ID NO: 7), HERCEPTIN® (SEQ ID NO: 9) and CAMPATH® (SEQ ID NO: 11) may be subjected to Fc walking.

For example, the first conserved stretch (from the N-terminus) in the Fc region of Rituxin begins with an lysine (as shown below). This arginine residue may be altered with any of the other known 21 amino acid residues, for instance, tyrosine. Additionally, an antibody molecule may comprise two or more modifications in one or more conserved regions of the Fc.

Rituximab Heavy Chain (Fc-amino acid
residues 232-448)
(SEQ ID NO: 1)
PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK

Similarly, double and triple mutants are generated by combining the single mutants and additionally selecting for binding properties (Yang et al., *J. Mol. Biol.* 254:392, 1995; Wu et al., *Proc Natl. Acad. Sci. USA* 95:6037, 1998). This is accomplished by simultaneous SSM at 3-5 different positions.

The final products of the overlap extension PCR reaction contain a T7 promoter and ribosome binding site in front of the antibody fragment gene. An HSV sequence is also present at the C-terminal end of the antibody fragment gene so that the MAb fragment protein can be detected by ELISA using an anti-HSV monoclonal antibody. The PCR overlap extension products are used as templates for coupled in vitro transcription-translation reactions to produce antibody variants. An *E. coli* S30 ribosomal extract is used for in vitro translation.

Alternatively or in addition to the modification(s) made to the Fc region of rituximab, the antibody may be modified in one or more of its complementarity determining regions (CDRs) by the methods described above for the Fc region. Specifically, one or more modifications are made to one or more of the heavy or light chain CDRs in rituximab (SEQ ID NO: 2 and 3, respectively). Any one or more of the CDR sequences presented below (bolded and underlined) from the Rituximab heavy or light chain may be modified by the SSM procedure.

Similarly, one or more of the above-described modifications may be made to the CDRs regions of REMICADE® (SEQ ID NO: 4 and 5), ERBITUX® (SEQ ID NO: 6 and 7), HERCEPTIN® (SEQ ID NO: 8 and 9) and CAMPATH® (SEQ ID NO: 10 and 11).

Rituximab Light Chain
(SEQ ID NO: 2)
QIVLSQSPAILSASPGEKVTMTCRASSSVSYMHWYQQKPGSSPKPWIYAP

SNLASGVPARFSGSGSGTSYSLTISRVEAEDAATYYCQQWSFNPPTFGAG

TKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNR

Rituximab Heavy Chain (SEQ ID NO: 3)

QAYLQQSGAELVRPGASVKMSCKASGYTFTSYNMHWVKQTPRQGLEWIGA

IYPGNGDTSYNQKFKGKATLTVDKSSSTAYMQLSSLTSEDSAVYFCARVV

-continued

YYSNSYWYFDVWGTGTTVTVSGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKAEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

For example, the first CDR (from the N-terminus) in the light chain molecule begins with an arginine (as shown below). This arginine residue may be altered with any of the other known 21 amino acid residues, for instance, tyrosine. Additionally, an antibody molecule may comprise two or more modifications in its CDR. When two or more amino acid modifications are present, all may be located in the CDR of a light chain molecule. Alternatively, all the modification may be located in the CDR of a heavy chain molecule. Moreover, the two or more modifications may be present in both the heavy chain molecule and the light chain molecule.

2. Screening Variant Rituximab Antibodies Specific for Group-II (V/F$^{158}$, H/H$^{131}$ Genotype)

Variant Rituximab antibodies or antibody fragments engineered for Group-II are screened using any of the functional assays described supra. Exemplary screening methods are described below.

For example, variant antibodies or antibody fragments may be analyzed by ELISA. In ELISA, 96-well microtiter plates are coated with the BSA conjugate of soluble FcγRIIIA V/F$^{158}$ or FcγRIIA H/H$^{131}$. The plates are then incubated with equal amounts of variant Rituximab antibodies or antibody fragments from each of the in vitro synthesis reactions. Heterogeneity of the transcribed/translated products is verified by DNA/protein sequencing protocols, or matrix-assisted laser desorption/ionization time-of-flight mass spectrometry (MALDI-TOF-MS). The ELISA results for the different mutants are recorded and the promising variant Rituximab antibodies or antibody fragments in terms of binding and affinity are subjected to in vitro ADCC assays (See, e.g., below).

Additionally, variant Rituximab antibodies or antibody fragments engineered for Group-II are screened for binding affinity to FcγRIIA and FcγRIIIA. One such affinity assay, AlphaScreen, uses untagged antibody to compete the interaction between biotinylated IgG bound to streptavidin donor beads and FcγR-His-GST bound to anti-GST acceptor beads. Competition SPR (Harvey et al., *Proc. Natl. Acad. Sci. USA* 101:9193, 2004) experiments measured capture of free antibody from a pre-equilibrated Ab:receptor analyte mixture to FcγRIIIA V$^{158}$-His-GST bound to an immobilized anti-GST surface. Equilibrium dissociation constants ($K_D$ values) are then calculated by using the proportionality of initial binding rate on free antibody concentration in the Ab:receptor equilibrium (Schier et al., *J. Mol. Biol.* 255:28, 1996; Daugherty et al., *Protein Eng.* 11:825-832, 1998).

Further, variant Rituximab antibodies or antibody fragments may be screened for ADCC activity. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277; Bruggemann et al., 1987, J Exp Med 166:135 1; Wilkinson et al., 2001, J Immunol Methods 258:183; Patel et al., 1995 J Inzinunoi Methods 184:29 and herein (see e.g., section entitled "Characterization and Functional Assays" infra). Alternatively, or additionally, ADCC activity of the antibody may be assessed in vivo, e.g., in an animal model such as that disclosed in Clynes et al., 1998, PNAS USA 95:652.

Additionally, variant Rituximab antibodies or antibody fragments may be screened for ADCP activity. For the phagocytosis experiments involved in this assay, monocytes are isolated from PBMCs of individuals belonging to patient Group-II (FcγRIIIA V/F$^{158}$ and FcγRIIA H/H$^{131}$) by using a Percoll gradient and differentiated into macrophages by culturing in a medium supplemented with 0.1 ng/ml granulocyte macrophage colony-stimulating factor for 1 week. For imaging, WIL2-S target cells are labeled with PKH67 (Sigma) and co-cultured for 24 hours with macrophages at an effector: target cell ratio of 3:1 in the presence of 100 ng/ml variant Rituximab. Cells are then treated with secondary antibodies anti-CD11-RPE and anti-CD14-RPE (DAKO) for 15 minutes before live cell imaging using a fluorescence microscope. For quantitative ADCP (i.e., antibody-dependent cell-mediated phagocytosis; macrophage mediated ADCC), WIL2-S target cells are labeled with PKH67, seeded in a 96-well plate at 20×10$^3$ cells per well, and treated with WT or the variant Rituximab at the designated final concentrations. Macrophages are labeled with PKH26 (Sigma) and added to the opsonized labeled target cells at 20×10$^3$ cells per well, and the cells are co-cultured for 18 h. Fluorescence is measured by using dual-label flow cytometry. Variant antibodies or antibody fragments with increased potency and efficacy are selected. CDC assays are performed according to published procedures (Gazzano-Santoro et al., *J. Immunol. Meth.* 202: 163, 1997; Uchida et al., *J. Exp. Med.* 199:1659, 2004).

Also, variant Rituximab antibodies or antibody fragments may be screened for those variant antibodies or antibody fragments that are capable of depleting B-cells in a subject. For instance, in vivo B-cell depletion assays may be employed. In such assays, Cynomolgus monkeys (*Macaca fascicularis*) are injected intravenous once daily for 4 consecutive days with wild-type or the variant rituximab antibody (Reff et al., *Blood* 83:435-445, 1994). The test animals will be allotyped for the FcγR polymorphisms, and if required, the animals corresponding to V/F$^{158}$ and H/H$^{131}$ genotypes will be used for the experiment. The experiment is comprised of six treatment Groups of ~0.1, 0.2, 2, 7, or 30 µg/kg (variant Rituximab antibody) or ~2 or 30 µg/kg (wild-type control), with three monkeys per treatment Group. Blood samples are acquired on two separate days before dosing (baseline) and at days 1, 2, 5, 15, and 28 after initiation of dosing. For each sample, cell populations are quantified by flow cytometry by using specific antibodies against the representative marker antigens. Percent B-cell depletion is calculated by comparing B-cell counts on the given day with the average of the two baseline measures for each animal.

3. Selection of Variant Rituximab Antibodies Optimized for Group-II (V/F$^{158}$, H/H$^{131}$ Genotype)

Variant Rituximab antibodies or antibody fragments are considered optimized for Group-II when they exhibit properties (e.g. binding affinity, ADCC activity, etc.) similar to those properties exhibited by Groups (genotypes) associated with a higher degree of responsiveness to Rituxamab. In other embodiments, variant Rituximab antibodies or antibody fragments are considered optimized for Group-II when they exhibit properties (i.e. binding affinity, ADCC activity, etc.) similar to those properties exhibited by the Group associated with the highest degree of responsiveness to Rituximab (i.e. Group-1).

In some embodiments, variant antibodies or antibody fragments are considered optimized for Group-II when they exhibit a binding affinity to FcγRIIA and FcγRIIIA that is increased to a level exhibited by Groups with a higher degree of responsiveness to Rituximab. In other embodiments, variant antibodies or antibody fragments are considered optimized for Group-II when they exhibit a binding affinity to FcγRIIA and FcγRIIIA that is increased to the level exhibited by the Group with the highest degree of responsiveness to Rituximab (Group-I).

In some embodiments, variant antibodies or antibody fragments are considered optimized for Group-II when they have ADCC activity similar to the ADCC activity exhibited by Groups with a higher degree of responsiveness to Rituximab. In other embodiments, variant antibodies or antibody fragments are considered optimized for Group-II when they exhibit ADCC activity similar to the ADCC activity exhibited by the Group with the highest degree of responsiveness to Rituximab (Group-I).

Variant Rituximab antibodies or antibody fragments that exhibit a similar degree of responsiveness in the patients of Group-II as compared to the responsiveness of Rituximab in the patients of Group-I are considered patient Group optimized. Variant antibodies optimized for a Group-II are selected for use in the treatment of patients of Group-II.

Example 5

Enhancement of an Antibody's Effector Functions with a Genotype Optimized Fc The Fc nucleotide sequence (Fc cassette) from an antibody optimized for responsiveness for a particular FcγRIIA and FcγRIIIA genotype (e.g. by the methods described in the above examples) can be used to optimize the responsiveness of other antibodies used to treat the same or other subjects with the particular FcγRIIA and FcγRIIIA genotype.

Fc cassettes with optimized responsiveness for each FcγRIIA (H/$R^{131}$) polymorphism and FcγRIIIA (V/$F^{158}$) polymorphism are used to optimize the responsiveness exhibited by other antibodies. As such, an Fc cassette that is optimized for the V/$F^{158}$, H/$H^{131}$ (Group-II) genotype can be used to optimize the responsiveness of patients of the same genotype to another antibody. For example, the optimized Fc cassette for the V/$F^{158}$, H/$H^{131}$ (Group-II) genotype, engineered to optimize responsiveness to Rituximab, is used to optimize the responsiveness in patients of the same genotype to any other therapeutic antibody, such as HERCEPTIN®.

While the example described in detail below is directed toward optimizing HERCEPTIN® for the V/$F^{158}$, H/$H^{131}$ genotype, it will be understood that the same protocol may be employed to engineer optimized antibodies for any other FcγRIIA and FcγRIIIA genotype.

Optimizing HERCEPTIN® for Group-II (V/$F^{158}$, H/$H^{131}$)

HERCEPTIN® may be optimized for a patient with a Group-II genotype (V/$F^{158}$, H/$H^{131}$) by fusion of the antigen binding domain of HERCEPTIN® to a Group-II optimized Fc cassette. Specifically, an Fc cassette engineered to optimize responsiveness to an antibody (other than S HERCEPTIN®) for Group-II patients is used to optimize responsiveness to HERCEPTIN®.

As previously described, a variant Rituximab antibody is engineered for optimized responsiveness in a patient with a Group-II genotype (V/$F^{158}$, H/$H^{131}$). The optimized Fc portion of Rituximab is fused to the antigen binding domain of HERCEPTIN® by recombinant techniques. Specifically, the Group-II optimized Rituximab Fc cassette is fused in frame with the antigen binding domain of HERCEPTIN® and inserted into an vector. The vector may be transfected into an appropriate host cell and expressed to produce the optimized Fc-HERCEPTIN®fusion. Any methods for generating an antibody fusion, such as, for example, those previously discussed, may be employed.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A method for generating a reference index which correlates treatment response to nine FcγRIIIa and FcγRIIa genotype groups, said method comprising:
   (a) genotyping multiple human subjects, each subject has or had an ADCC-treatable disease or disorder, and is or was administered antibody therapy for said disease or disorder resulting in a treatment response; said genotyping classifies said subject into one of nine genotype groups corresponding to
   $V/V^{158}$ and $H/H^{131}$, designated group I;
   $V/F^{158}$ and $H/H^{131}$, designated group II;
   $F/F^{158}$ and $H/H^{131}$, designated group III;
   $V/V^{158}$ and $H/R^{131}$, designated group IV;
   $V/F^{158}$ and $H/R^{131}$, designated group V;
   $F/F^{158}$ and $H/R^{131}$, designated group VI;
   $V/V^{158}$ and $R/R^{131}$, designated group VII;
   $V/F^{158}$ and $R/R^{131}$, designated group VIII; and
   $F/F^{158}$ and $R/R^{131}$, designated group IX; and
   (b) further classifying said treatment response of each subject based on its FcγRIIIa $V/F^{158}$ and FcγRIIa $H/R^{131}$ genotype groups to generate a reference index which correlates said nine categories of treatment response with said nine genotype groups.

2. A method for classifying a human test subject having said ADCC-treatable disease or disorder into a category of treatment response to said antibody therapy, said method comprising:
   a) genotyping said test subject to classify into one of nine genotype groups corresponding to
   $V/V^{158}$ and $H/H^{131}$, designated group I;
   $V/F^{158}$ and $H/H^{131}$, designated group II;
   $F/F^{158}$ and $H/H^{131}$, designated group III;
   $V/V^{158}$ and $H/R^{131}$, designated group IV;
   $V/F^{158}$ and $H/R^{131}$, designated group V;
   $F/F^{158}$ and $H/R^{131}$, designated group VI;
   $V/V^{158}$ and $R/R^{131}$, designated group VII;
   $V/F^{158}$ and $R/R^{131}$, designated group VIII; and
   $F/F^{158}$ and $R/R^{131}$, designated group IX; and
   b) classifying said test subject using said genotype group into a category of treatment response which is indicated from said reference index of claim 1.

3. The method of claim 2, wherein:
   a) said category of treatment response is a component of a treatment decision; or
   b) said category of treatment response is a component of a decision not to treat with said antibody therapy; or
   c) said test subject is treated with said antibody therapy.

4. The method of claim 1, wherein said subject was administered antibody therapy in the past.

5. The method of claim 1, wherein said ADCC-treatable disease or disorder is a neoplastic disease or disorder.

6. The method of claim 1, wherein said ADCC-treatable disease or disorder is an autoimmune disease or disorder.

7. The method of claim 1, wherein said antibody therapy comprised administration of an anti-CD20 antibody.

8. The method of claim 1, wherein said antibody therapy comprised treatment with an antibody selected from the group consisting of rituximab, alemtuzumab, daclizumab, trastuzumab, omalizumab, efalizumab, bevacizumab, infliximab, adalimumab, cetuximab, basiliximab, palivizumab, panitumumab, natalizumab, gemtuzumab ozogamicin, abciximab, ranibizumab, eculizumab, muromonab-CD3, tositumomab and ibritumomab tiuxetan.

9. A method for predicting treatment response to an antibody therapy for a human test subject having an ADCC-treatable disease or disorder, said method comprising:
   a) classifying said test subject into one of nine genotype groups corresponding to
   $V/V^{158}$ and $H/H^{131}$, designated group I;
   $V/F^{158}$ and $H/H^{131}$, designated group II;
   $F/F^{158}$ and $H/H^{131}$, designated group III;
   $V/V^{158}$ and $H/R^{131}$, designated group IV;
   $V/F^{158}$ and $H/R^{131}$, designated group V;
   $F/F^{158}$ and $H/R^{131}$, designated group VI;
   $V/V^{158}$ and $R/R^{131}$, designated group VII;
   $V/F^{158}$ and $R/R^{131}$, designated group VIII; and
   $F/F^{158}$ and $R/R^{131}$, designated group IX; and
   b) using a reference index that correlates nine categories of treatment response upon treatment with an antibody therapy with said genotype groups, thereby providing a prediction of treatment response for said test subject.

10. The method of claim 9, further including a step of genotyping said test subject by evaluating a biological sample by hybridization for classifying said subject into one of said nine genotype groups.

11. The method of claim 9 wherein
   a) said predicting of treatment response is a component of a treatment decision; or
   b) said predicting of treatment response is a component of a decision not to treat with said antibody therapy; or
   c) said test subject is treated with said antibody therapy.

12. A method for selecting a genotype group for a particular treatment with an antibody therapy for human test subjects having an ADCC-treatable disease or condition, said method comprising:
   a) using a reference index which correlates categories of treatment responses, said categories numbering more than three, and said categories corresponding to a single or combination of genotype groups, with said genotype group corresponding to
   $V/V^{158}$ and $H/H^{131}$, designated group I;
   $V/F^{158}$ and $H/H^{131}$, designated group II;
   $F/F^{158}$ and $H/H^{131}$, designated group III;
   $V/V^{158}$ and $H/R^{131}$, designated group IV;
   $V/F^{158}$ and $H/R^{131}$, designated group V;
   $F/F^{158}$ and $H/R^{131}$, designated group VI;
   $V/V^{158}$ and $R/R^{131}$, designated group VII;
   $V/F^{158}$ and $R/R^{131}$, designated group VIII; and
   $F/F^{158}$ and $R/R^{131}$, designated group IX; and
   b) selecting said genotype group(s) corresponding to a particular category of treatment response.

13. The method of claim 12, wherein said method identifies a particular test subject for said treatment, where said subject is in said genotype group corresponding to said category of treatment response.

14. The method of claim 12, wherein said method identifies a particular test subject for said treatment who is treated with said antibody therapy.

15. The method of claim 12, wherein said category of treatment response is a component of a decision not to treat with said antibody therapy.

16. The method of claim 12, wherein said genotype group corresponds to group IX.

17. A method for generating a reference index which correlates treatment response to FcγRIIIa and FcγRIIa genotype groups, said method comprising:
  (a) genotyping multiple human subjects, each subject has or had an ADCC-treatable disease or disorder, and is or was administered antibody therapy for said disease or disorder resulting in a treatment response; said genotyping classifies said subject into one of nine genotype groups corresponding to
    $V/V^{158}$ and $H/H^{131}$, designated group I;
    $V/F^{158}$ and $H/H^{131}$, designated group II;
    $F/F^{158}$ and $H/H^{131}$, designated group III;
    $V/V^{158}$ and $H/R^{131}$, designated group IV;
    $V/F^{158}$ and $H/R^{131}$, designated group V;
    $F/F^{158}$ and $H/R^{131}$, designated group VI;
    $V/V^{158}$ and $R/R^{131}$, designated group VII;
    $V/F^{158}$ and $R/R^{131}$, designated group VIII; and
    $F/F^{158}$ and $R/R^{131}$, designated group IX; and
  (b) further classifying said treatment response of each subject based on its FcγRIIIa $V/F^{158}$ and FcγRIIa $H/R^{131}$ genotype groups,
  wherein two or more genotype groups are combined to one category of treatment response to generate a reference index which contains more than three categories of treatment response.

18. A method for classifying a human test subject having said ADCC-treatable disease or disorder into a category of treatment response to said antibody therapy, said method comprising:
  a) genotyping said test subject into one of nine genotype groups corresponding to
    $V/V^{158}$ and $H/H^{131}$, designated group I;
    $V/F^{158}$ and $H/H^{131}$, designated group II;
    $F/F^{158}$ and $H/H^{131}$, designated group III;
    $V/V^{158}$ and $H/R^{131}$, designated group IV;
    $V/F^{158}$ and $H/R^{131}$, designated group V;
    $F/F^{158}$ and $H/R^{131}$, designated group VI;
    $V/V^{158}$ and $R/R^{131}$, designated group VII;
    $V/F^{158}$ and $R/R^{131}$, designated group VIII; and
    $F/F^{158}$ and $R/R^{131}$, designated group IX; and
  b) classifying said test subject using said genotype group into a category of treatment response which is indicated from said reference index of claim 17.

19. The method of claim 18, wherein said categories of treatment response number more than three, and one category corresponds to genotype: group I alone; group V alone; group IX alone; groups I, II, Ill, IV, and VII together; groups II and III together; groups IV and VII together; groups V, VI, VIII, and IX together; groups I, II, and III together; groups IV, V, and VI together; groups VII, VIII, and IX together; groups I, IV, and VII together; groups II, V, and VIII together; or groups III, VI, and IX together.

20. The method of claim 18, wherein
  a) said category of treatment response is a component of a treatment decision;
  b) said category of treatment response is a component of a decision not to treat with said antibody therapy; or
  c) said test subject is treated with said antibody therapy.

21. A method for selecting a genotype group for a particular treatment with an antibody therapy for human test subjects having an ADCC-treatable disease or condition, said method comprising:
  a) using a reference index which correlates categories of treatment responses, each category corresponding to treatment response to a single genotype group, with said genotype groups corresponding to
    $V/V^{158}$ and $H/H^{131}$, designated group I;
    $V/F^{158}$ and $H/H^{131}$, designated group II;
    $F/F^{158}$ and $H/H^{131}$, designated group III;
    $V/V^{158}$ and $H/R^{131}$, designated group IV;
    $V/F^{158}$ and $H/R^{131}$, designated group V;
    $F/F^{158}$ and $H/R^{131}$, designated group VI;
    $V/V^{158}$ and $R/R^{131}$, designated group VII;
    $V/F^{158}$ and $R/R^{131}$, designated group VIII; and
    $F/F^{158}$ and $R/R^{131}$, designated group IX; and
  b) selecting said genotype group corresponding to a particular category of treatment response.

22. The method of claim 21, wherein said method identifies a particular test subject for said treatment, where said subject is in said genotype group corresponding to said category of treatment response.

23. The method of claim 21, wherein said method identifies a particular test subject for said treatment who is treated with said antibody therapy.

24. The method of claim 21, wherein said category of treatment response is a component of a decision not to treat with said antibody therapy.

25. The method of claim 21, wherein said genotype group corresponds to group IX.

26. A method for predicting treatment response to an antibody therapy for a human test subject having an ADCC-treatable disease or disorder, said method comprising:
  a) classifying said test subject into one of nine genotype groups corresponding to
    $V/V^{158}$ and $H/H^{131}$, designated group I;
    $V/F^{158}$ and $H/H^{131}$, designated group II;
    $F/F^{158}$ and $H/H^{131}$, designated group III;
    $V/V^{158}$ and $H/R^{131}$, designated group IV;
    $V/F^{158}$ and $H/R^{131}$, designated group V;
    $F/F^{158}$ and $H/R^{131}$, designated group VI;
    $V/V^{158}$ and $R/R^{131}$, designated group VII;
    $V/F^{158}$ and $R/R^{131}$, designated group VIII; and
    $F/F^{158}$ and $R/R^{131}$, designated group IX; and
  b) using a reference index, said reference index containing more than three categories of treatment response, each corresponding to one or more genotype groups, which correlates category of treatment response to said genotype groups.

27. The method of claim 26, wherein:
  a) said category of treatment response is a component of a treatment decision; or
  b) said category of treatment response is a component of a decision not to treat with said antibody therapy; or
  c) said test subject is treated with said antibody therapy.

28. The method of claim 26, further including a step of genotyping said test subject by evaluating a biological sample by hybridization for classifying said subject into one of said nine genotype groups.

29. The method of claim 26, wherein said reference index has nine categories of treatment response, each category corresponding to a single genotype group.

30. The method of claim 26, wherein said categories of responsiveness include at least one category which corresponds to: group I alone; group V alone; group IX alone; groups I, II, Ill, IV, and VII together; groups II and III together; groups IV and VII together; groups V, VI, VIII, and IX together; groups I, II, and III together; groups IV, V, and VI together; groups VII, VIII, and IX together; groups I, IV, and VII together; groups II, V, and VIII together; or groups III, VI, and IX together.

31. The method of claim 26, wherein said ADCC-treatable disease or disorder is a neoplastic disease or disorder.

32. The method of claim 26, wherein said ADCC-treatable disease or disorder is an autoimmune disease or disorder.

33. The method of claim 26, wherein said antibody therapy is administration of an anti-CD20 antibody.

34. The method of claim 26, wherein said antibody therapy is treatment with an antibody selected from the group consisting of rituximab, alemtuzumab, daclizumab, trastuzumab, omalizumab, efalizumab, bevacizumab, infliximab, adalimumab, cetuximab, basiliximab, palivizumab, panitumumab, natalizumab, gemtuzumab ozogamicin, abciximab, ranibizumab, eculizumab, muromonab-CD3, tositumomab and ibritumomab tiuxetan.

35. A method of selecting an antibody therapy for human subjects having an ADCC-treatable disease, said antibodies in a set of two or more antibody therapies, said method comprising:
   a) classifying said subjects into nine genotype groups corresponding to
      $V/V^{158}$ and $H/H^{131}$, designated group I;
      $V/F^{158}$ and $H/H^{131}$, designated group II;
      $F/F^{158}$ and $H/H^{131}$, designated group III;
      $V/V^{158}$ and $H/R^{131}$, designated group IV;
      $V/F^{158}$ and $H/R^{131}$, designated group V;
      $F/F^{158}$ and $H/R^{131}$, designated group VI;
      $V/V^{158}$ and $R/R^{131}$, designated group VII;
      $V/F^{158}$ and $R/R^{131}$, designated group VIII; and
      $F/F^{158}$ and $R/R^{131}$, designated group IX; and
   b) comparing said genotypes to reference indices which correlate said genotype groups with corresponding categories of treatment response upon antibody therapy, each of said categories of treatment response corresponding to one or more genotype groups; and
   c) selecting a preferred antibody therapy for a particular genotype group where the degree of treatment response is improved compared to those other antibody therapies.

36. The method of claim 35, wherein a test subject has said particular genotype group, and that preferred antibody therapy is selected for that test subject.

37. The method of claim 35, wherein a test subject has said particular genotype group, and that preferred antibody therapy is selected for that test subject, and said test subject is treated with said preferred antibody therapy.

38. The method of claim 35, wherein said antibodies share antigen binding specificity.

39. The method of claim 35, wherein said antibodies differ in ability to mediate ADCC, phagocytosis or opsonization effector cell function.

40. The method of claim 35, wherein at least one of said reference indices has nine categories of treatment response.

* * * * *